(12) United States Patent
South et al.

(10) Patent No.: US 6,906,068 B1
(45) Date of Patent: Jun. 14, 2005

(54) SUBSTITUTED POLYCYCLIC ARYL AND HETEROARYL 1,2,4 - TRIAZINONES USEFUL AS ANTICOAGULANTS

(75) Inventors: Michael S. South, St. Louis, MO (US); Ashton T. Hamme, II, St. Louis, MO (US); William L. Neumann, St. Louis, MO (US); Darin E. Jones, Ballwin, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/009,447

(22) PCT Filed: May 17, 2000

(86) PCT No.: PCT/US00/09806

§ 371 (c)(1),
(2), (4) Date: Apr. 3, 2002

(87) PCT Pub. No.: WO00/69832

PCT Pub. Date: Nov. 23, 2000

Related U.S. Application Data

(60) Provisional application No. 60/134,794, filed on May 19, 1999.

(51) Int. Cl.[7] .................. C07D 253/065; C07D 239/02; A61K 31/53; A61K 31/513; A61P 7/02
(52) U.S. Cl. ................... 514/242; 514/269; 514/231.5; 544/182; 544/317; 544/111
(58) Field of Search ........................... 544/182; 514/242

(56) References Cited

U.S. PATENT DOCUMENTS

| | | |
|---|---|---|
| 4,489,096 A | 12/1984 | Terao et al. |
| 4,851,413 A | 7/1989 | Terao et al. |
| 4,992,469 A | 2/1991 | Ozawa et al. |
| 5,008,267 A | 4/1991 | Katakami et al. |
| 5,304,658 A | 4/1994 | Terao et al. |
| 5,441,960 A | 8/1995 | Bernstein et al. |
| 5,656,645 A | 8/1997 | Tamura et al. |
| 5,658,930 A | 8/1997 | Tamura et al. |
| 5,668,289 A | 9/1997 | Sanderson et al. |
| 5,741,819 A | 4/1998 | Illig et al. |
| 5,792,779 A | 8/1998 | Sanderson et al. |
| 5,861,380 A | 1/1999 | Gyorkos et al. |
| 5,866,573 A | 2/1999 | Sanderson et al. |
| 5,869,487 A | 2/1999 | Coburn et al. |
| 5,872,138 A | 2/1999 | Naylor-Olsen et al. |
| 6,011,158 A | 1/2000 | Tamura et al. |
| 6,037,356 A | 3/2000 | Lu et al. |
| 6,180,627 B1 | 1/2001 | Blagg et al. |

FOREIGN PATENT DOCUMENTS

| | | |
|---|---|---|
| DE | 198 51 421 A1 | 5/2000 |
| EP | 0 354 495 A1 | 2/1990 |
| WO | WO 98/09987 A1 | 3/1998 |
| WO | WO 99/48892 A1 | 9/1998 |
| WO | WO 99/43660 A1 | 9/1999 |

OTHER PUBLICATIONS

Rauch et al., Ann. Intern. Med. 134(3): 224–238, 2001.*
Van Aken et al., clin. Appl. Thromb. Hemost., 7(3): 195–204, 2001.*
Coburn, C.A., "Small–molecule direct thrombin inhibitors 1997–2000." Expert Opinions on Therapeutic Patents, 2001, 721–738, vol. 11, No. 5.
XP–002182132—Darvas, et al., "Investigation of the Common Mechanism of Action of Antibacterial Compounds Containing .gamma.–pyridone–.beta.–carboxylic acid Structure by Principal Component." Arzneim.–Forsch., 1979, pp. 1334–1339, vol. 29, 9.
XP–002172033—Kohama, et al., "Preparation of Piperidinyloxyacetylaminobenzoylalanine Derivatives and Analogs as Atithrombotics." JP 07,233,148.
XP–002187583—Moerner, Hoppe–Seyler's Z. Physiol. Chem., 69, 1910; 357.
Patel, et al., "Directed Aminomethylation of 3–Hydroxy–3(1H)–pyridinones and 3–hycroxy–4(1H)–pryidinones: Synthesis of iso–Deferiprone." Tetrahedron, 1996, pp. 1835–1840, vol. 52, No. 5.
XP–002182410—Trecourt, et al., "First Synthesis of (+–)–harzianopyridone by Metalation of Polysubstituted O–pyridylcarbamates." J. Heterocycl. Chem., 1995, pp. 1117–1114, vol. 32, No. 4.
Tulinsky, et al., "Novel Asymmetric Synthesis of Atropisomeric 6–Aryl Pyrazinones via an Unusual Chirality Transfer Process." J. Org. Chem., 1999, pp. 93–100, vol. 64, No. 1.

* cited by examiner

*Primary Examiner*—Venkataraman Balasubramanian

(57) ABSTRACT

The invention relates to substituted polycyclic aryl and heteroaryl pyrimidinone compounds useful as inhibitors of serine proteases of the coagulation cascade and compounds, compositions and methods for anticoagulant therapy for the treatment and prevention of a variety of thrombotic conditions including coronary artery and cerebrovascular diseases.

15 Claims, No Drawings

SUBSTITUTED POLYCYCLIC ARYL AND HETEROARYL 1,2,4 - TRIAZINONES USEFUL AS ANTICOAGULANTS

FIELD OF THE INVENTION

This invention is in the field of anticoagulant therapy, and specifically relates to compounds, compositions and methods for preventing and treating thrombotic conditions such as coronary artery and cerebrovascular disease. More particularly, the invention relates to substituted polycyclic aryl and heteroaryl pyrimidinone compounds that inhibit serine proteases of the coagulation cascade.

BACKGROUND OF THE INVENTION

Physiological systems control the fluidity of blood in mammals [Majerus, P. W. et al: Anticoagulant, Thrombolytic, and Antipiplatelet Drugs. In Hardman, J. G. and Limbird, L. E., editors: Goodman & Gilman's The Pharmacological Basis of Therapeutics. 9th edition. New York, McGraw-Hill Book Co., 1996, pp. 1341–1343]. Blood must remain fluid within the vascular systems and yet be able to undergo hemostasis, cessation of blood loss from a damaged vessel, quickly. Hemostasis or clotting begins when platelets first adhere to macromolecules in subendothelian regions of an injured and/or damaged vessels. These platelets aggregate to form the primary hemostatic plug and stimulate local activation of plasma coagulation factors leading to generation of a fibrin clot that reinforces the aggregated platelets.

Plasma coagulation factors include factors II, V, VII, VIII, IX, X, XI, and XII; these are also called protease zymogens. These coagulation factors or protease zymogens are activated by serine proteases leading to coagulation in a so called "coagulation cascade" or chain reaction [Handin, R. I.: Bleeding and Thrombosis. In Wilson, J. et al. editors: Harrison's Principles of Internal Medicine. 12th Edition, New York, McGraw-Hill Book Co., 1991,p350]. Coagulation or clotting occurs in two ways through different pathways. An intrinsic or contact pathway leads from XII to XIIa to XIa to IXa and to the conversion of X to Xa. Xa with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by Xa. The presence of Tissue Factor and VIIa accelerates formation of Xa in the presence of calcium ion and phospholipids. Formation of Xa leads to thrombin, fibrin, and a fibrin clot as described above. The presence of one or more of these many different coagulation factors and two distinct pathways of dotting could enable the efficacious, selective control and better understanding of parts of the coagulation or clotting process.

While clotting as a result of an injury to a blood vessel is a critical physiological process for mammals such as man, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

There have been several reports of non-peptidic and peptidic pyrimidinone compounds that act as an inhibitor of a coagulation factor present in the coagulation cascade or clotting process. In PCT Patent Application WO 98/47876, Van Boeckel et al. describe peptidic 6-alkylpyridones and 2-alkylpyrimidinones as anti-thrombotic compounds. In PCT Patent Application WO 98/16547, Zhu and Scarborough describe 3-(N-heterocyclylamino)-4,5,6-substituted-pyridonylacetamides and 2,4-substituted-5-(N-heterocyclylamino)-pyrimidinonyl-acetamides containing amide substituents and having activity against mammalian factor Xa. In U.S. Pat. No. 5,656,645, Tamura et al. describe 4,5,6-substituted-3-aminopyridonyl-acetamides, 1,6-substituted-5-aminouracinylacetamides, and 2,4-substituted-5-aminopyrimidinonyl-acetamides containing amide substituents having a formyl function and having activity against thrombin. In U.S. Pat. No. 5,658,930, Tamura et al. again describe 4,5,6-substituted-3-aminopyridonyl-acetamides, 1,6-substituted-5-aminouracinylacetamides, and 2,4-substituted-5-aminopyrimidinonyl-acetamides containing amide substituents having a formyl function and having activity against thrombin. In PCT Patent Applications 96/18644 and 97/46207, Tamura et al. further describe 4,5,6-substituted-3-aminopyridonylacetamides, 1,6-substituted-5-aminouracinyl-acetamides, and 2,4-substituted-5-amino-pyrimidinonylacetamides containing amide substituents having a formyl function and having activity against thrombin. In PCT Patent Application WO 98/09949, Suzuki et al. describe 2-heterocyclylacetamido derivatives of 1,2-diketones and report that they inhibit proteases, especially chymase inhibitors.

SUMMARY OF THE INVENTION

It is an object of the present invention to provide compounds that are beneficial in anticoagulant therapy and that have a general structure:

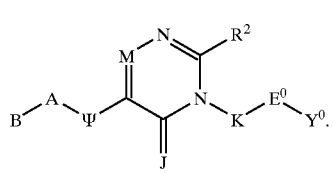

Formula (I)

It is another object of the present invention to provide methods for preventing and treating thrombotic conditions, such as coronary artery disease, cerebrovascular disease, and other coagulation related disorders. Such thrombotic conditions are prevented and treated by administering to a patient in need thereof an effective amount of compounds of Formula (I).

Various other objects and advantages of the present invention will become apparent from the following description of the invention.

DESCRIPTION OF THE INVENTION

The present invention relates to a class of compounds comprising Substituted Polycyclic Aryl and Heteroaryl pyrimidinones, which are beneficial in anticoagulant therapy for the treatment and prevention of a variety of thrombotic conditions including coronary artery and cerebrovascular disease, as given in Formula (I):

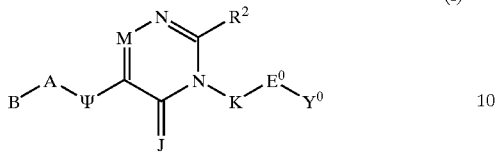

(I)

or a pharmaceutically acceptable salt thereof, wherein;
J is selected from the group consisting of O and S;
J is optionally selected from the group consisting of CH—$R^6$ and N—$R^6$ wherein $R^6$ is a linear spacer moiety having a chain length of 1 to 4 atoms linked to the point of bonding of a substituent selected from the group consisting of $R^{4a}$, $R^{4b}$, $R^{39}$, $R^{40}$, $R^5$, $R^{14}$, and $R^{15}$ to form a heterocyclyl ring having 5 through 8 contiguous members;
J is optionally selected from the group consisting of CH—$R^6$ and N—$R^6$ wherein $R^6$ is a linear spacer moiety having a chain length of 1 to 4 atoms linked to the points of bonding of both $R^{4a}$ and $R^{4b}$ to form a heterocyclyl ring having 5 through 8 contiguous members;
J is optionally selected from the group consisting of CH—$R^6$ and N—$R^6$ wherein $R^6$ is a linear spacer moiety having a chain length of 1 to 4 atoms linked to the points of bonding of both $R^{39}$ and $R^{40}$ to form a heterocyclyl ring having 5 through 8 contiguous members;
B is formula (V):

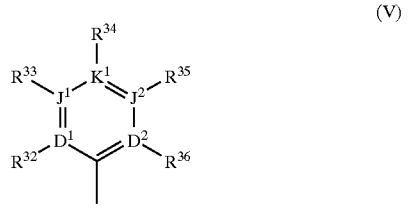

(V)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N with the proviso that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;
$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, acetamido, haloacetamido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycoalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxylalkyl, heteroaralkoxy, cycoalkoxy, cycloalkenyloxy, cycoalkoxyalkyl, cycloalkylalkoxy, cycloalkenyloxyalkyl, cycloalkylenedioxy, halocycloalkoxy, halocycloalkoxyalkyl, halocycloatkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alklylnosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroalkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroalalkenyl, carboxyalkyl, carboalkoxy, alkoxycarboxamido, alkylamidocarbonylamido, arylamidocarbonylamido, carboalkoxyalkyl, carboalkoxyalkenyl, carboxy. carboaralkoxy, carboxamido, carboxamidoalkyl, cyano, carbohaloalkoxy, phosphono, phosphonoalkyl, diaralkoxyphosphono, and diaralkoxyphosphonoalkyl;
$R^{16}$, $R^{19}$, $R^{32}$, $R^{33}$, $R^{34}$, $R^{35}$, and $R^{36}$ and independently optionally $Q^b$ with the proviso that no more than one of $R^{16}$ and $R^{19}$ is $Q^b$ at the same time and that $Q^b$ is $Q^{be}$;
$R^{32}$ and $R^{33}$, $R^{33}$ and $R^{34}$, $R^{34}$ and $R^{35}$, and $R^{35}$ and $R^{36}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous member a heteroaryl ring having 5 through 6 contiguous members, and an aryl with the proviso that no more than one of the group consisting of spacer pairs $R^{32}$ and $R^{33}$, $R^{33}$ and $R^{34}$, $R^{34}$ and $R^{35}$, and $R^{35}$ and $R^{36}$ are used at the same time;
$R^9$ and $R^{10}$, $R^{10}$ and $R^{11}$, $R^{11}$ and $R^{12}$, and $R^{12}$ and $R^{13}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pain $R^9$ and $R^{10}$, $R^{10}$ and $R^{11}$, $R^{11}$ and $R^{12}$, and $R^{12}$ and $R^{13}$ are used at the same time;

B is optionally formula (VI):

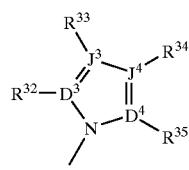

(VI)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N with the proviso that $R^{32}$, $R^{33}$, $R^{34}$, and $R^{35}$ are each independently selected to maintain the tetravalent nature of carbon, trivalent nature of nitrogen, the divalent nature of sulfur, and the divalent nature of oxygen;

B is optionally selected from the group consisting of hydrido, trialkylsilyl, C2–C8 alkyl, C3–C8 alkynyl, C3–C8 alkylenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R_{32}$, $R_{33}$, $R_{34}$, $R_{35}$, and $R_{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 though 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, Se(O), Se(O)$_2$, Se(O)$_2$N($R^7$), ($R^7$)NSe(O)$_2$, P(O)($R^8$), N($R^7$)P(O)($R^8$), P(OR)($R^8$)N($R^7$), C(N$R^7$)N($R^7$), ($R^7$)NC(N$R^7$), ($R^7$)NC(N$R^7$)N$R^7$, and N($R^7$) with the proviso that no more than one of the group consisting of rr and pa is 0 at the same time;

$R^7$ and $R^8$ an independently selected from the group consisting of hydrido, hydroxy, alkyl, alkenyl, aryl, aralkyl, aryloxy, alkoxy, alkenyloxy, alkylthio, alkylamino, arylthio, arylamino, acyl, aroyl, heteroaroyl, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, heteroaryl, heteroaryloxy, heteroarylamino, heteroaralkyl, heteroaralkyloxy, heteroaralkylamino, and heteroaryloxyalkyl;

$R^{14}$, $R^{15}$, $R^{37}$, $R^{38}$, $R^{39}$, $R^{40}$, $R^{41}$ and $R^{42}$ are independently selected from the group consisting of amidino, hydroxyamino, hydrido, hydroxy, halo, cyano, aryloxy, amino, alkylamino, dialkylamino, hydroxyalkyl, aminoalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, trialkylsilyl dialkoxyphosphono, diaralkoxyphosphono, dialkoxyphosphonoalkyl, and diaralkoxyphosphonoalkyl with the proviso that $R^{37}$ and $R^{38}$ are independently selected from other than formyl and 2-oxoacyl;

$R^{14}$ and $R^{14}$, when bonded to different carbons, are optionally taken together to form a group selected from the group consisting of covalent bond, alkylene, haloalkylene, and a linear moiety spacer selected to form a ring selected from the group consisting of cycloalkyl ring having from 5 through 8 contiguous members, cycloalkenyl ring having from 5 through 8 contiguous members, and a heterocyclyl having from 5 through 8 contiguous members;

$R^{14}$ and $R^{15}$, when bonded to different carbons, are optionally taken together to form a group selected from the group consisting of covalent bond, alkylene, haloalkylene, and a linear moiety spacer selected to form a ring selected from the group consisting of a cycloalkyl ring having from 5 through 8 contiguous members, a cycloalkenyl ring having from 5 through 8 contiguous members, and a heterocyclyl having from 5 through 8 contiguous members;

$R^{15}$ and $R^{15}$, when bonded to different carbons, are optionally taken together to form a group selected from the group consisting of covalent bond, alkylene, haloalkylene, and a linear moiety spacer selected to form a ring selected from the group consisting of cycloalkyl ring having from 5 through 8 contiguous members, cycloalkenyl ring having from 5 through 8 contiguous members, and a heterocyclyl having from 5 through 8 contiguous members;

$\Psi$ is selected from the group consisting of $NR^5$, O, C(O), C(S), S, S(O), S(O)$_2$, ON($R^5$), P(O)($R^8$), and $CR^{39}R^{40}$;

$R^5$ is selected from the group consisting of hydrido, hydroxy, amino, alkyl, alkenyl, alkynyl, aryl, aralkyl, aryloxy, aralkoxy, alkoxy, alkenyloxy, alkylthio, arylthio, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalklenyloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, and dialkoxyphosphonoalkyl;

$R^{39}$ and $R^{40}$, when bonded to the same carbon, are optionally taken together to form a group selected from 8 group consisting of oxo, thiono, $R^5$—N, alkylene, haloalkylene, and a linear moiety spacer having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

M is selected from the group consisting of N and $R^1$—C;

$R^2$ and $R^1$ are independently selected from the group consisting of $Z^0$—Q, hydrido, alkyl, alkenyl, and halo;

$R^1$ is optionally selected from the group consisting of amino, aminoalkyl, alkylamino, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$R^2$ is optionally selected from the group consisting of amidino, guanidino, dialkylsulfonium, trialkylphosphonium, dialkylsulfoniumalkyl, heteroarylamino, amino, nitro, alkylamino, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$R^2$ and $R^{4a}$, $R^2$ and $R^{4b}$, $R^2$ and $R^{14}$, and $R^2$ and $R^{15}$ are optionally independently selected to form spacer pairs wherein a spacer pair is taken together to form a linear moiety having from 2 through 5 contiguous atoms connecting the points of bonding of said spacer pair members to form a heterocyclyl ring having from 5 through 8 contiguous members with the proviso that no more than one of the group of spacer pairs consisting of $R^2$ and $R^{4a}$, $R^2$ and $R^{4b}$, $R^2$ and, $R^{14}$, and $R^2$ and $R^{15}$ is used at the same time;

$R^2$ is optionally independently selected to form a linear moiety having from 2 through 5 contiguous atoms linked to the points of bonding of both $R^{4a}$ and $R^{4b}$ to form a heterocyclyl ring having from 5 through 8 contiguous members;

$Z^0$ is selected from the group consisting of covalent single bond, $(CR^{41}R^{42}))_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), S(O)$_2$, S(O)$_2$N($R^{41}$), N($R^{41}$)S(O)$_2$, Se, Se(O), Se(O)$_2$, Se(O)$_2$N($R^{41}$), N($R^{41}$)Se(O)$_2$, P(O)($R^8$), N($R^7$)P(O)($R^8$), P(O)($R^8$)N($R^7$), N($R^{41}$), ON($R^{41}$), and $SiR^{28}R^{29}$, and $(CH(R^{41}))_e$—$W^{22}$—$(CH(R^{42}))_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C=C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{41}$ and $R^{42}$ are selected from other than halo and cyano when directly bonded to N and $Z^0$ is directly bonded to the pyrimidinone ring;

$R^{28}$ and $R^{29}$ are independently selected from the group consisting of hydrido, hydroxyalkyl, alkyl, alkenyl, alkynyl, aryl, aralkyl, aryloxyalkyl, acyl, aroyl, aralkanoyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroarlkylthioalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycoalkl, carboalkoxycycloalkyl, dicarboalkoxycycloalkyl, formylalkyl, acylalkyl, arylsulfinylalkyl, arylsulfonylalkyl, aralkylsulfinyl, cycloalkylsulfinylalkyl, cycloalcylsufonylalkyl, heteroarylsulfonylalkyl, heteroarylsulfinylalkyl, aralkylsulfinylalkyl, aralkylsulfonylalkyl, carboxy, dialkoxyphosphono, diaralkoxyphosphono, dialkoxyphosphonoalkyl and diaralkoxyphosphonoalkyl;

$R^{28}$ and $R^{29}$ are optionally taken together to form a linear moiety spacer having from 2 through 7 contiguous atoms and forming a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

Q is formula (II):

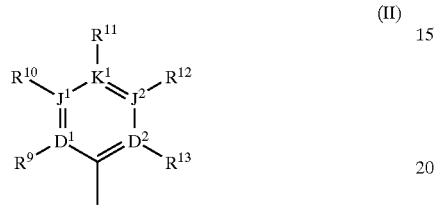

(II)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S and no more than four of $D^1$, $D^2$, $J^1$, $J^2$ and $K^1$ can be N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

Q is optionally selected from formula (III):

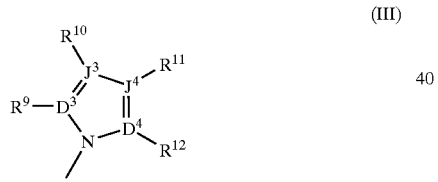

(III)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N with the proviso that $R^9$, $R^{10}$, $R^{11}$, and $R^{12}$ are each independently selected to maintain the tetravalent nature of carbon, trivalent nature of nitrogen, the divalent nature of sulfur, and the divalent nature of Q is optionally selected from the group consisting of hydrido, alkyl, alkoxy, alkylamino, alkylthio, haloalkylthio, alkenyl, alkynyl, saturated hetetrocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that $Z^0$ is selected from other than a single covalent bond when Q is hydrido;

K is $(CR^{4a}R^{4b})_n$ wherein n is an integer selected from 1 through 4;

$R^{4a}$ and $R^{4b}$ are independently selected from the group consisting of halo, hydrido, hydroxy, cyano, hydroxyalkyl, alkyl, alkenyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, haloalkyl, haloalkenyl, heteroaryl, heteroarylalkyl, heteroarylthioalkyl, heteroaralkylthioalkyl, cyanoalkyl, alkylsulfinylalkyl, alkylsulfonylalkyl, haloalkylsulfinyl, arylsulfinylalkyl, arylsulfonylalkyl, heteroarylsulfonylalkyl, heteroarylsulfinylalkyl, aralkylsulfinylalkyl, and aralkylsulfonylalkyl with the provisos that halo, hydroxy, and cyano are bonded to different carbons when simultaneously present and that $R^{4a}$ and $R^{4b}$ are other than hydroxy or cyano when bonded to the carbon directly bonded to the pyrimidinone nitrogen;

$R^{4a}$ and $R^{4b}$, when bonded to the same carbon, are optionally taken together to form a group selected from the group consisting of oxo, thiono, and a linear spacer moiety having from 2 through 7 contiguous atoms connected to form a ring selected from the group consisting of a cycloalkyl ring having 3 through 8 contiguous members, a cycloalkenyl ring having 5 through 8 contiguous members, and a heterocyclyl ring having 5 through 8 contiguous members with the proviso that $R^{4a}$ and $R^{4b}$ taken together is other than oxo or thiono when the common carbon is directly bonded to the pyrimidinone nitrogen;

$E^0$ is $E^1$, when K is $(CR^{4a}R^{4b})$ wherein $E^1$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N($R^7$)C(O), C(O)N($R^7$)S(O)$_2$, Se, Se(O), Se(O)$_2$, Se(O)$_2$N($R^7$), N($R^7$)Se(O)$_2$, P(O)($R^8$), N($R^7$)P(O)($R^8$), P(O)($R^8$)N($R^7$), N($R^7$), ON($R^7$), SiR$^{28}$R$^{29}$, $CR^{4a}=CR^{4b}$, ethynylidene (C≡C; 1,2-ethynyl), and $C=CR^{4a}R^{4b}$;

K is optionally selected to be $(CH(R^{14}))_j$—T wherein j is selected from a integer from 0 through 3 and T is selected from the group consisting of single covalent bond, O, S, and N($R^7$) with the provisos that $R^{14}$ is other than hydroxy, cyano, halo, amino, alkylamino, dialkylamino, and sulfhydryl when j is 1 and that $(CH(R^{14}))_j$ is bonded to the pyrimidinone ring;

$E^0$ is optionally $E^2$, when K is $(CH(R^{14}))_j$—T, wherein $E^2$ is selected from the group consisting of a covalent single bond C(O), C(S), C(O)O, C(S)O, C(O)S, C(S)S, C(O)N($R^7$), ($R^7$)NC(O), C(S)N($R^7$), ($R^7$)NC(S), ($R^7$)NC(O)O, ($R^7$)NC(S)S, ($R^7$)NC(O)S, ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N(H)C(O), C(O)N(H)S(O)$_2$, Se(O), Se(O)$_2$, Se(O)$_2$N($R^7$), N($R^7$)Se(O)$_2$, P(O)($R^8$), N($R^7$)P(O)($R^8$), P(O)($R^8$)N($R^7$), and N($R^7$);

K is optionally selected to be G—$(CH(R^{15}))_k$ wherein k is selected from an integer from 1 through 3 and G is selected from the group consisting of O, S, and N($R^7$) with the proviso that $R^{15}$ is other than hydroxy, cyano, halo, amino, alkylamino, dialkylamino, and sulfhydryl when k is 1;

$E^0$ is optionally $E^3$ when K is G—$(CH(R^{15}))_k$ wherein $E^3$ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC (S), OC(O)N(R$^7$), (R$^7$)NC(O)O, SC(S)N(R$^7$), (R$^7$)NC (S)S, SC(O)N(R$^7$), (R$^7$)NC(O)S, OC(S)N(R$^7$), (R$^7$)NC (S)O, N(R$^8$)C(O)N(R$^7$), (R$^7$)NC(O)N(R$^8$), N(R$^8$)(S)N (R$^7$), (R$^7$)NC(S)N(R$^8$), S(O), S(O)$_2$, S(O)$_2$N(R$^7$), N(R$^7$)S(O)$_2$, Se, Se(O), Se(O)$_2$, Se(O)$_2$N(R$^7$), N(R$^7$) Se(O)$_2$, P(O)(R$^8$), N(R$^7$)P(O)(R$^8$), P(O)(R$^8$)N(R$^7$), N(R$^7$), ON(R$^7$), SiR$^{28}$R$^{29}$, CR$^{4a}$=R$^{4b}$, ethynylidene (C=C; 1,2-ethynyl), and C=CR$^{4a}$R$^{4b}$;

Y$^0$ is formula (IV):

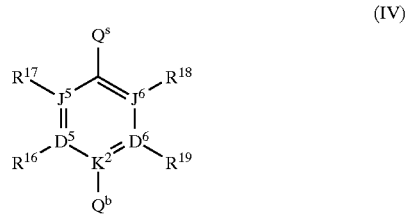

(IV)

wherein D$^5$, D$^6$, J$^5$, and J$^6$ are independently selected from the group consisting of C, N, O, S and a covalent bond with the provisos that no more than one is a covalent bond, K$^2$ is independently selected from the group consisting of C and N$^+$, no more than one of D$^5$, D$^6$, J$^5$, and J$^6$ is O, no more than one of D$^5$, D$^6$, J$^5$, and J$^6$ is S, one of D$^5$, D$^6$, J$^5$, and J$^6$ must be a covalent bond when two of D$^5$, D$^6$, J$^5$, and J$^6$ are O and S, no more than three of D$^5$, D$^6$, J$^5$, and J$^6$ are N when K$^2$ is N$^+$, and no more than four of D$^5$, D$^6$, J$^5$, and J$^6$ are N when K$^2$ is carbon with the provisos that R$^{16}$, R$^{17}$, R$^{18}$, and R$^{19}$ are each independently selected to maintain the tetravalent nature of carbon, trivalent nature of nitrogen, the divalent nature of sulfur, and the divalent nature of oxygen;

R$^{16}$ and R$^{17}$ are independently optionally taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

R$^{18}$ and R$^{19}$ are independently optionally taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl:

Q$^b$ is selected from the group consisting of NR$^{20}$R$^{21}$, $^+$NR$^{20}$R$^{21}$R$^{22}$, oxy, alkyl, aminoalkylenyl, alkylamino, dialkylamino, dialkylsulfoniumalkyl, acylamino and Q$^{be}$ wherein Q$^{be}$ is hydrido and R$^{20}$, R$^{21}$, and R$^{22}$ are independently selected from the group consisting of hydrido, amino, alkyl, hydroxy, alkoxy, aminoalkylenyl, alkylamino, dialkylamino, and hydroxyalkyl with the provisos that no more than one of R$^{20}$, R$^{21}$, and R$^{22}$ is hydroxy, alkoxy, alkylamino, amino, and dialkylamino at the same time and that R$^{20}$, R$^{21}$, and R$^{22}$ must be other than be hydroxy, alkoxy, alkylamino, amino, and dialkylamino when K$^2$ is N$^+$;

R$^{20}$ and R$^{21}$, R$^{20}$ and R$^{22}$, and R$^{21}$ and R$^{22}$ an independently optionally selected to form a spacer pair wherein a spacer pair is taken together to form a linear moiety having from 4 through 7 contiguous atoms connecting the points of bonding of said spacer pair members to form a heterocyclyl ring having 5 through 8 contiguous members with the proviso that no more than one of the group consisting of spacer pairs R$^{20}$ and R$^{21}$, R$^{20}$ and R$^{22}$, and R$^{21}$ and R$^{22}$ is used at the same time;

Q$^b$ is optionally selected from the group consisting of N(R$^{26}$)SO$_2$N(R$^{23}$)(R$^{24}$), N(R$^{26}$)C(O)OR$^5$, N(R$^{26}$)C(O) SR$^5$, N(R$^{26}$)C(S)OR$^5$ and N(R$^{26}$)C(S)SR$^5$ with the proviso that no more than one of R$^{23}$, R$^{24}$, and R$^{26}$ can be hydroxy, alkoxy, alkyleneamino, alkylamino, amino, or dialkylamino when two of the group consisting of R$^{23}$, R$^{24}$, and R$^{26}$ are bonded to the same atom;

Q$^b$ is optionally selected from the group consisting of dialkylsulfonium, trialkylphosphonium, C(NR$^{25}$) NR$^{23}$R$^{24}$, N(R$^{26}$)C(NR$^{25}$)N(R$^{23}$)(R$^{24}$), N(R$^{26}$)C(O)N (R$^{23}$)(R$^{24}$), N(R$^{26}$)C(S)N(R$^{23}$)(R$^{24}$), C(NR$^{25}$)OR$^5$, C(O)N(R$^{26}$)C(NR$^{25}$)N(R$^{23}$)(R$^{24}$), C(S)N(R$^{26}$)C(NR$^{25}$) N(R$^{23}$)(R$^{24}$), N(R$^{26}$)N(R$^{26}$)C(NR$^{25}$)N(R$^{23}$)(R$^{24}$), ON(R$^{26}$)C(NR$^{25}$)N(R$^{23}$)(R$^{24}$), N(R$^{26}$)N(R$^{26}$)SO$_2$N (R$^{23}$)(R$^{24}$), C(NR$^{25}$)SR$^5$, C(O)NR$^{23}$R$^{24}$, and C(O) NR$^{23}$R$^{24}$ with the provisos that no more than one of R$^{23}$, R$^{24}$, and R$^{26}$ can be hydroxy, alkoxy, alkylamino, amino, or dialkylamino when any two of the group consisting of R$^{23}$, R$^{24}$, and R$^{26}$ are banded to the same atom and that said Q$^b$ group is bonded directly to a carbon atom;

R$^{23}$, R$^{24}$, R$^{25}$, and R$^{26}$ are independently selected from the group consisting of hydrido, alkyl, hydroxy, alkoxy, alkylenylamino, amino, alkylamino, dialkylamino, and hydroxyalkyl;

R$^{23}$ and R$^{24}$ are optionally taken together to form a linear spacer moiety having from 4 through 7 contiguous atoms connecting the points of bonding to form a heterocyclyl ring having 5 through 8 contiguous members;

R$^{23}$ and R$^{25}$, R$^{24}$ and R$^{25}$, R$^{25}$ and R$^{26}$, R$^{24}$ and R$^{26}$, and R$^{23}$ and R$^{26}$ are independently optionally selected to form a spacer pair wherein a spacer pair is taken together from the points of bonding of selected spacer pair members to form the group L—U—V wherein L, U, and V are independently selected from the group consisting of O, S, C(O), C(S), C(J$_H$)$_2$S(O), SO$_2$, OP(OR$^{31}$)R$^{30}$, P(O)R$^{30}$, P(S)R$^{30}$, C(R$^{30}$)R$^{31}$, C=C (R$^{30}$)R$^{31}$, (O)$_2$POP(O)$_2$, R$^{30}$(O)POP(O)R$^{30}$, Si(R$^{29}$) R$^{28}$, Si(R$^{29}$)R$^{28}$Si(R$^{29}$)R$^{28}$, Si(R$^{29}$)R$^{28}$OSi(R$^{29}$)R$^{28}$, (R$^{28}$)R$^{29}$COC(R$^{28}$)R$^{29}$, (R$^{28}$)R$^{29}$CSC(R$^{28}$R$^{29}$, C(O)C (R$^{30}$)=C(R$^{31}$), C(S)C(R$^{30}$)=C(R$^{31}$), S(O)C(R$^{30}$)=C (R$^{31}$), SO$_2$C(R$^{30}$)=C(R$^{31}$), PR$^{30}$C(R$^{30}$)=C(R$^{31}$), P(O)R$^{30}$C(R$^{30}$)=C(R$^{31}$), P(S)R$^{30}$C(R$^{30}$)=C(R$^{31}$), DC(R$^{30}$)(R$^{31}$)D, OP(OR$^{31}$)R$^{30}$, P(O)R$^{30}$, P(S)R$^{30}$, Si(R$^{28}$)R$^{29}$ and N(R$^{30}$), and a covalent bond with the proviso that no more than any two of L, U and V are simultaneously covalent bonds and the heterocyclyl comprised of by L, U, and V has from 5 through 10 contiguous member, D is selected from the group consisting of oxygen, C=O, C=S, S(O)$_m$ wherein m is an integer selected from 0 through 2;

J$_H$ is independently selected from the group consisting of OR$^{27}$, SR$^{27}$ and N(R$^{20}$)R$^{21}$;

R$^{27}$ is selected from the group consisting of hydrido, alkyl, alkenyl, alkynyl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryloxyalkyl, heteroaryl, heteroarylalkyl, heteroarylthioalkyl, heteroaralkylthioalkyl, arylsulfinylalkyl, arylsulfonylalkyl, cycloalkylsulfinylalkyl, cycloalkylsufonylalkyl, heteroarylsulfonylalkyl, heteroarylsulfinylalkyl, aralkylsulfinylalkyl and aralkylsulfonylalkyl;

$R^{30}$ and $R^{31}$ are independently selected from the group consisting of hydrido, hydroxy, thiol, aryloxy, amino, alkylamino, dialkylamino, hydroxyalkyl, heteroaryloxyalkyl, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, haloaralkylsulfinylalkyl, aralkylsulfonylalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamaidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, sulfonylalkyl, alkylsulfonylalkyl, aralkoxysulfonylalkyl, alkoxysulfonylalkoxy, aralkoxysulfonylalkoxy, sulfonylalkoxy, alkoxysulfonylalkylamino, aralkoxysulfonylalkylamino, and sulfonylalkylamino;

$R^{30}$ and $R^{31}$ are optionally taken to form a linear moiety spacer group having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{23}$ and $R_{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group of 1,2-disubstituted radicals consisting of a cycloalkyl radical, a cycloalkenyl radical wherein cycloalkyl and cycloalkenyl radicals are substituted with one or more groups selected from $R^{30}$ and $R^{31}$, an aryl radical, an heteroaryl radical, a saturated heterocyclic radical and a partially saturated heterocyclic radical wherein said 1,2-substitutents are independently selected from C=O, C=S, C($R^{28}$)$R^{32}$, S(O), S(O)$_2$, OP(OR$^{31}$)R$^{30}$, P(O)R$^{30}$, P(S)R$^{30}$ and Si($R^{28}$)$R^{29}$;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group of radicals consisting of 1,2-disubstituted alkylene radicals and 1,2-disubstituted alkenylene radical wherein said 1,2-substitutents are independently selected from C=O, C=S, C($R^{28}$)$R^{29}$, S(O), S(O)$_2$, OP(OR$^{31}$)R$^{30}$, P(O)R$^{30}$, P(S)R$^{30}$, and Si($R^{28}$)$R^{29}$ and said alkylene and alkenylene radical are substituted with one or more $R^{30}$ or $R^{31}$ substituents;

$Q^s$ is selected from the group consisting of a single covalent bond. $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), SC(S)N($R^{14}$), SC(O)N($R^{14}$), OC(S)N($R^{14}$), N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)N($R^{14}$), N($R^{14}$)S(O)$_2$, Se, Se(O), Se(O)$_2$, Se(O)$_2$N($R^{17}$), N($R^{14}$)Se(O)$_2$, P(O)($R^8$), N($R^7$)P(O)($R^8$), P(O)($R^8$)N($R^7$), N($R^{14}$), ON($R^{14}$), and SiR$^{28}$R$^{29}$, (CH($R^{14}$))$_c$—W$^1$—(CH($R^{15}$))$_d$ wherein c and d are integers independently selected from 1 through 4, and $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O), P(O)($R^8$), N($R^7$)P(O)($R^8$), P(O)($R^8$)N($R^7$), N($R^{14}$), ON($R^{14}$), SiR$^{28}$R$^{29}$, and (CH($R^{14}$))$_e$—W$^{22}$—(CH($R^{15}$))$_h$ wherein e and h are integers independently selected from 0 through 2 and $W^{22}$ is selected from the group consisting of CR$^{41}$=CR$^{42}$, CR$^{41}$R$^{42}$=C; vinylidene), ethynylidene (C=C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperanyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, $(CH(R^{14}))_e$ and are bonded to $E^0$;

$R^{37}$ and $R^{37}$, when bonded to different carbons, are optionally taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{37}$ and $R^{38}$, when bonded to different carbons, are taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{38}$ and $R^{38}$, when bonded to different carbons, are taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having, from 3 through 8 contiguous members;

$R^{37}$ and $R^{38}$, when bonded to the same carbon, are taken together to form a group selected from a group consisting of oxo, thiono, alkylene, haloalkylene, and a linear moiety spacer having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$Y^0$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—$W^1$—$(CH(R^{15}))_d$ wherein c and d are integers independently selected from 1 through 4, and $W^1$ is selected from the group consisting of $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O)$_2$, P(O)($R^8$), N($R^7$)P(O)($R^8$), P(O)($R^8$)N($R^7$), N($R^{14}$), ON($R^{14}$), SiR$^{28}$R$^{29}$, and $(CH(R^{14}))_e$—$W^2$—$(CH(R^{15}))_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo and cyano when directly bonded to N, that $(CR^{37}R^{38})_f$, $(CH(R^{15}))_c$, and $(CH(R^{15}))_e$ are bonded to $E^0$, and $Q^b$ is selected from other than N($R^{26}$)N($R^{26}$)C(N$R^{25}$)N($R^{23}$)($R^{24}$) or ON($R^{26}$)C(N$R^{25}$)N($R^3$)($R^{24}$) when $Q^{ss}$ is $(CR^{37}R^{38})_f$ wherein f is other than the integer 1;

$Y^0$ is optionally $Q^b$—$Q^{sss}$ wherein $Q_{sss}$ is $(CH(R^{38}))_r$—$W^3$, r is an integer selected from 1 through 3, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, r is an integer selected from 1 through 3, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hydrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 3, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4- isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{sssr}$ wherein $Q^{sssr}$ is (CH($R^{38}$))$_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-isoquinolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In an embodiment of compounds of Formula I or a pharmaceutically acceptable salt thereof, J is selected from the group consisting of O and S;

J is optionally selected from the group consisting of CH—$R^6$ and N—$R^6$ wherein $R^6$ is a linear spacer moiety having a chain length of 1 to 4 atoms linked to the point of bonding of a substituent selected from the group consisting of $R^{4a}$, $R^{4b}$, $R^{39}$, $R^{40}$, $R^5$, $R^{14}$, and $R^{15}$ to form a heterocyclyl ring having 5 through 8 contiguous members;

B is formula (V):

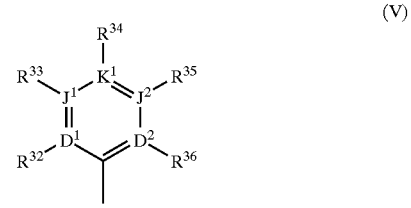

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N with the proviso that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, acetamido, haloacetamido, amidino, guanidino, dialkylsulfonium, trialkylphosphonium, dialkybulfoniumalkyl, carboxy, heteroaralkylthio, heteroaryloxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$ with the proviso that no more than one of $R^{16}$ and $R^{19}$ is $Q^b$ at the same time and that $Q^b$ is $Q^{be}$;

$R^{32}$ and $R^{33}$, $R^{33}$ and $R^{34}$, $R^{34}$ and $R^{35}$, and $R^{35}$ and $R^{36}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members a heteroaryl ring having 5 through 6 contiguous members, and an aryl with the proviso that no more than one of the group consisting of spacer pairs $R^{32}$ and $R^{33}$, $R^{33}$ and $R^{34}$, $R^{34}$ and $R^{35}$, and $R^{35}$ and $R^{36}$ can be used at the same time;

$R^9$ and $R^{10}$, $R^{10}$ and $R^{11}$, $R^{11}$ and $R^{12}$, and $R^{12}$ and $R^{13}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R^9$ and $R^{10}$, $R^{10}$ and $R^{11}$, $R^{11}$ and $R^{12}$, and $R^{12}$ and $R^{13}$ can be used at the same time;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring bon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to th $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, P(O)($R^8$), N($R^7$)P(O)($R^8$), P(O)($R^8$)N($R^7$), C(N$R^7$)N ($R^7$), ($R^7$)NC(N$R^7$), ($R^7$)NC(N$R^7$)N$R^7$, and N($R^7$) with the proviso that no more than one of the group consisting of rr and pa can be 0 at the same time;

$R^7$ and $R^8$ are independently selected from the group consisting of hydrido, hydroxy, alkyl, acyl, aroyl, heteroaroyl, and alkoxyalkyl;

$R^{14}$, $R^{15}$, $R^{37}$, and $R^{38}$ are independently selected from the group consisting of hydrido, hydroxy, halo, cyano, hydroxyalkyl, alkoxy, alkyl, alkoxyalkyl, cycloalkyl, cycloalkylalkyl, cycloalkenyl, cycloalkenylalkyl, haloalkyl, haloalkenyl, haloalkoxy, haloalkoxyalkyl, haloalkenyloxyalkyl, halocycloalkoxy, halocycloalkoxyalkyl, halocycloalkenyloxyalkyl, carboxy, carboxyalkyl, carboalkoxy, carboxamide, and carboxamidoalkyl;

$R^{14}$ and $R^{38}$ can be independently selected from the group consisting of acyl, aroyl, and heteroaroyl with the proviso that acyl is selected from other than formyl and 2-oxoacyl;

Ψ is selected from the group consisting of N$R^5$, O, C(O), C(S), S, S(O), S(O)$_2$, ON($R^5$), P(O)($R^8$), and C$R^{39}R^{40}$;

$R^5$ is selected from the group consisting of hydrido, hydroxy, amino, alkyl, alkoxy, alkoxyalkyl, haloalkyl, acyl, aroyl, and heteroaroyl;

$R^{39}$ and $R^{40}$ are independently selected from the group consisting of hydrido, hydroxy, halo, cyano, hydroxyalkyl, acyl, aroyl, heteroaroyl, acylamido, alkoxy, alkyl, alkoxyalkyl, haloalkyl, haloalkoxy, haloalkoxyalkyl, alkylsulfonyl, haloalkylsulfonyl, carboxy, carboxyalkyl, carboalkoxy, carboxamide, and carboxamidoalkyl;

M is selected from the group consisting of N and $R^1$—C;

$R^2$ and $R^1$ are independently selected from the group consisting of $Z^0$—Q, hydrido, alkyl, alkenyl, and halo;

$R^1$ is optionally selected from the group consisting of amino, aminoalkyl, alkylamino, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl heteroaroyl, aralkanoyl, heteroaralkanoyl, haloalkanoyl, hydroxyhaloalkyl, cyano, and phosphono;

$Z^0$ is selected from the group consisting of covalent single bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$),($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), S(O)$_2$, S(O)$_2$N($R^{41}$), N($R^{41}$)S(O)$_2$, Se, Se(O), Se(O)$_2$, S(O)$_2$N($R^{41}$), N($R^{41}$)Se(O)$_2$, P(O)($R^8$), N($R^7$)P(O)($R^8$), P(O)($R^8$)N($R^7$), N($R^{41}$), ON($R^{41}$), and Si$R^{28}R^{29}$, and (CH($R^{41}$))$_e$—$W^2$—(CH($R^{42}$))$_h$ wherein e and h are integers independently selected from 0 through 2 and $W^{22}$ is selected from the group consisting of $CR^{41}$=$CR^{42}$, $CR^{41}R^{42}$=C: vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{41}$ and $R^{42}$ are selected from other than halo and cyano when directly bonded to N and $Z^0$ is directly bonded to the pyrimidinone ring;

$R^{41}$ and $R^{42}$ are independently selected from the group consisting of amidino, hydroxyamino, hydrido, hydroxy, amino, halo, cyano, aryloxy, hydroxyalkyl, acyl, aroyl, heteroaroyl, heteroaryloxyalkyl, alkoxy, alkyl, aryl, aralkyl, aryloxyalkyl, aralkoxyalkylalkoxy, alkoxyalkyl, heteroaryloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroaralkyl, heteroaryltlioalkyl, heteroaralkylthioalkyl, alkylsulfonyl, haloalkylsulfonyl, arylsulfonyl, arylsulfonylalkyl, aralkylsulfonyl, cycloalkylsulfonyl, cycloalkylsulfonylalkyl, heteroarylsulfonylalkyl, heteroarylsulfonyl, and aralkylsulfonylalkyl;

Q is formula (II):

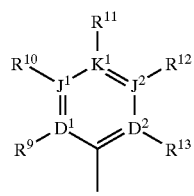

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are independently selected to maintain the tetravalent nature of carbon, trivalent nature of nitrogen, the divalent nature of sulfur, and the divalent nature of oxygen;

Q is optionally selected from formula (III):

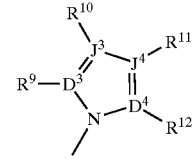

(III)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N with the proviso that $R^9$, $R^{10}$, $R^{11}$, and $R^{12}$ are each independently selected to maintain the tetravalent nature of carbon, trivalent nature of nitrogen, the divalent nature of sulfur, and the divalent nature of oxygen;

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that $Z^0$ is selected from other than a single covalent bond when Q is hydrido;

K is $(CR^{4a}R^{4b})_n$ wherein n is an integer selected from 1 through 2;

$R^{4a}$ and $R^{4b}$ are independently selected from the group consisting of halo, hydrido, hydroxy, cyano, hydroxyalkyl, alkyl, alkenyl, alkoxyalkyl, aralkyl, heteroaralkyl, alkylthioalkyl, haloalkyl, haloalkenyl, and cyanoalkyl;

$E^0$ is $E^1$, when K is $(CR^{4a}R^{4b})_n$, wherein $E^1$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N($R^7$)C(O), C(O)N($R^7$)S(O)$_2$, P(O)($R^8$), N($R^7$)P(O)($R^8$), P(O)($R^8$)N($R^7$), N($R^7$), ON($R^7$), $CR^{42}$=$CR^{4b}$, ethynylidene (C≡C; 1,2-ethynyl), and C=$CR^{4a}R^{4b}$;

K is optionally (CH($R^{14}$))$_j$—T wherein j is selected from a integer from 0 through 2 and T is selected from the group consisting of single covalent bond, O, S, and N($R^7$) with the proviso that (CH($R^{14}$))$_j$ is bonded to the pyrimidinone ring;

$E^0$ is optionally $E^2$, when K is (CH($R^{14}$))$_j$—T, wherein $E^2$ is selected from the group consisting of a covalent single bond, C(O), C(S), C(O)O, C(S)O, C(O)S, C(S)S, C(O)N($R^7$), ($R^7$)NC(O), C(S)N($R^7$), ($R^7$)NC(S), ($R^7$)NC(O)O, ($R^7$)NC(S)S, ($R^7$)NC(O)S, ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N(H)C(O), C(O)N(H)S(O)$_2$, P(O)($R^8$), N($R^7$)P(O)($R^8$), P(O)($R^8$)N($R^7$), and N($R^7$);

K is optionally G—(CH($R^{15}$))$_k$ wherein k is selected from an integer from 1 through 2 and G is selected from the group consisting of O, S, and N(R$^7$) with the proviso that R$^{15}$ is other than hydroxy, cyano, halo, amino, alkylamino, dialkylamino, and sulfhydryl when k is 1;

E$^0$ is optionally E$^3$ when K is G—(CH(R$^{15}$))$_k$, wherein E$^3$ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, P(O)(R$^8$), N(R$^7$)P(O)(R$^8$), P(O)(R$^8$)N(R$^7$), N(R$^7$), ON(R$^7$), CR$^{4a}$=CR$^{4b}$, ethynylidene (C≡C; 1,2-ethynyl), and C=CR$^{4a}$R$^{4b}$;

Y$^0$ is formula (IV):

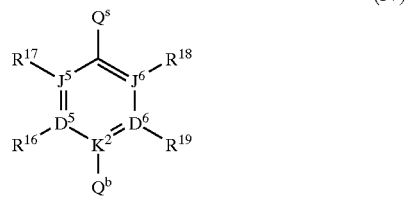

(IV)

wherein D$^5$, D$^6$, J$^5$, and J$^6$ are independently selected from the group consisting of C, N, O, S and a covalent bond with the provisos that no more than one is a covalent bond, K$^2$ is independently selected from the group consisting of C and N$^+$, no more than one of D$^5$, D$^6$, J$^5$, and J$^6$ is O, no more than one of D$^5$, D$^6$, J$^5$, and J$^6$ is S, one of D$^5$, D$^6$, J$^5$, and J$^6$ must be a covalent bond when two of D$^5$, D$^6$, J$^5$, and J$^6$ are O and S, no more than three of D$^5$, D$^6$, J$^5$, and J$^6$ is N when K$^2$ is N$^+$, and no more than four of D$^5$, D$^6$, J$^5$, and J$^6$ are N when K$^2$ is carbon with the provisos that R$^{16}$, R$^{17}$, R$^{18}$, and R$^{19}$ are each independently selected to maintain the tetravalent nature of carbon, trivalent nature of nitrogen, the divalent nature of sulfur, and the divalent nature of oxygen;

R$^{16}$ and R$^{17}$ are optionally independently taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

Q$^b$ is selected from the group consisting of NR$^{20}$R$^{21}$, $^+$NR$^{20}$R$^{21}$R$^{22}$, oxy, alkyl, aminoalkylenyl, alkylamino, dialkylamino, dialkylsulfoniumalkyl, acylamino and Q$^{be}$, wherein Q$^{be}$ is hydrido and R$^{20}$, R$^{21}$, and R$^{22}$ are independently selected from the group consisting of hydrido, amino, alkyl, hydroxy, alkoxy, aminoalkylenyl, alkylamino, dialkylamino, and hydroxyalkyl with the provisos that no more than one of R$^{20}$, R$^{21}$, and R$^{22}$ is hydroxy, alkoxy, alkylamino, amino, and dialkylamino at the same time and that R$^{20}$, R$^{21}$, and R$^{22}$ must be other than be hydroxy, alkoxy, alkylamino, amino, and dialkylamino when K$^2$ is N$^+$;

R$^{20}$ and R$^{21}$, R$^{20}$ and R$^{22}$, and R$^{21}$ and R$^{22}$ are independently optionally selected to form a spacer pair wherein a spacer pair is taken together to form a linear moiety having from 4 through 7 contiguous atoms connecting the points of bonding of said spacer pair members to form a heterocyclyl ring having 5 through 8 contiguous members with the proviso that no more than one of the group consisting of spacer pairs R$^{20}$ and R$^{21}$, R$^{20}$ and R$^{22}$, and R$^{21}$ and R$^{22}$ is used at the same time;

Q$^b$ is optionally selected from the group consisting of N(R$^{26}$)SO$_2$N(R$^{23}$)(R$^{24}$), N(R$^{26}$)C(O)OR$^5$, N(R$^{26}$)C(O)SR$^5$, N(R$^{26}$)C(S)OR$^5$ and N(R$^{26}$)C(S)SR$^5$ with the proviso that no more than one of R$^{23}$, R$^{24}$, and R$^{26}$ is hydroxy, alkoxy, alkylamino, amino, and dialkylamino when two of the group consisting of R$^{23}$, R$^{24}$, and R$^{26}$ are bonded to the same atom;

Q$^b$ is optionally selected from the group consisting of dialkylsulfonium, trialkylphosphonium, C(NR$^{25}$)NR$^{23}$R$^{24}$, N(R$^{26}$)C(NR$^{25}$)N(R$^{23}$)(R$^{24}$), N(R$^{26}$)C(O)N(R$^{23}$)(R$^{24}$), N(R$^{26}$)C(S)N(R$^{23}$)(R$^{24}$), C(NR$^{25}$)OR$^5$, C(O)N(R$^{26}$)C(NR$^{25}$)N(R$^{23}$)(R$^{24}$), C(S)N(R$^{26}$)C(NR$^{25}$)N(R$^{23}$)(R$^{24}$), N(R$^{26}$)N(R$^{26}$)C(NR$^{25}$)N(R$^{23}$)(R$^{24}$), ON(R$^{26}$)C(NR$^{25}$)N(R$^{23}$)(R$^{24}$), N(R$^{26}$)N(R$^{26}$)SO$_2$N(R$^{23}$)(R$^{24}$), C(NR$^{25}$)SR$^5$, C(O)NR$^{23}$R$^{24}$, and C(O)NR$^{23}$R$^{24}$ with the provisos that no more than one of R$^{23}$, R$^{24}$, and R$^{26}$ can be hydroxy, alkoxy, alkylaminol, amino, or dialkylamino when two of the group consisting of R$^{23}$, R$^{24}$, and R$^{26}$ are bonded to the same atom and that said Q$^b$ group is bonded directly to a carbon atom;

R$^{23}$, R$^{24}$, R$^{25}$, and R$^{26}$ are independently selected from the group consisting of hydrido, alkyl, hydroxy, alkoxy, aminoalkylenyl, alkylamino, dialkylamino, amino, and hydroxyalkyl;

R$^{23}$ and R$^{24}$ are optionally taken together to form a linear spacer moiety having from 4 through 7 contiguous atoms connecting the points of bonding to form a heterocyclyl ring having 5 through 8 contiguous members;

Q$^s$ is selected from the group consisting of a single covalent bond, (CR$^{37}$R$^{38}$)$_b$—(W$^0$)$_{az}$ wherein az is an integer selected from 0 through 1, b is an integer selected from 1 through 4, and W$^0$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), SC(S)N(R$^{14}$), SC(O)N(R$^{14}$), OC(S)N(R$^{14}$), N(R$^{15}$)C(O)N(R$^{14}$), (R$^{14}$)NC(O)N(R$^{15}$), N(R$^{15}$)C(S)N(R$^{14}$), (R$^{14}$)NC(S)N(R$^{15}$), S(O), S(O)$_2$, S(O)$_2$N(R$^{14}$), N(R$^{14}$)S(O)$_2$, P(O)(R$^8$), N(R$^7$)P(O)(R$^8$), P(O)(R$^8$)N(R$^7$), N(R$^{14}$), ON(R$^{14}$), (CH(R$^{14}$))$_c$—W$^1$—(CH(R$^{15}$))$_d$ wherein c and d are integers independently selected from 1 through 4, and W$^1$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), (R$^{14}$)NC(O)O, SC(S)N(R$^{14}$), (R$^{14}$)NC(S)S, SC(O)N(R$^{14}$), (R$^{14}$)NC(O)S, OC(S)N(R$^{14}$), (R$^{14}$)NC(S)O, N(R$^{15}$)C(O)N(R$^{14}$), (R$^{14}$)NC(O)N(R$^{15}$), N(R$^{15}$)C(S)N(R$^{14}$), (R$^{14}$)NC(S)N(R$^{15}$), S(O), S(O)$_2$, S(O)$_2$N(R$^{14}$), N(R$^{14}$)S(O)$_2$, P(O)(R$^8$), N(R$^7$)P(O)(R$^8$), PO)(R$^8$)N(R$^7$), N(R$^{14}$), ON(R$^{14}$), and (CH(R$^{14}$))$_e$—W$^{22}$—(CH(R$^{15}$))$_h$ wherein e and h are integers independently selected from 0 through 2 and W$^{22}$ is selected from the group consisting of CR$^{41}$=CR$^{42}$, CR$^{41}$R$^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, $(CH(R^{14}))_e$ and are bonded to $E^0$;

$Y^0$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—$W^1$—$(CH(R^{15}))_d$ wherein c and d are integers independently selected from 1 through 4, and $W^1$ is selected from the group consisting of $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15)C(O)N(R14)}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P(O)($R^8$), P(O)($R^8$)N($R^7$), N($R^{14}$), ON($R^{14}$), and $(CH(R^{14}))_e$—$W^2$—$(CH(R^{15}))_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo and cyano when directly bonded to N and that $(CR^{37}R^{38})_p$, $(CH(R^{14}))_c$, and $(CH(R^{14}))_e$ are bonded to $E^0$;

$Y^0$ is optionally $Q^b$—$Q^{sss}$ wherein $Q^{sss}$ is $(CH(R^{38}))_r$—$W^3$, r is an integer selected from 1 through 3, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hydrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, r is an integer selected from 1 through 3, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,3-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetmhydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,3-tetrahydropyranyl, and each carbon and hydrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 3, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{sssss}$ is $(CH(R^{38}))_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5- benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4--quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In another embodiment of compounds of Formula I or a pharmaceutically acceptable salt thereof, J is selected from the group consisting of O and S;
B is formula (V):

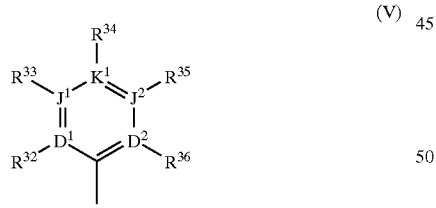

(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, acetamido, haloacetamido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroalkoxy, cycloalkyl, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkylamidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$ with the proviso that no more than one of $R^{16}$ and $R^{19}$ is $Q^b$ at the same time and that $Q^b$ is $Q^{be}$;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl, C5–C10 cycloalkenyl, and C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(O)N($R^7$), C(S)N($R^7$), ($R^7$)NC(O), ($R^7$)NC(S), and N($R^7$) with the proviso that no more than one of the group consisting of rr and pa can be 0 at the same time, $R^7$ and $R^8$ are independently selected from the group consisting of hydrido, hydroxy, alkyl, and alkoxyalkyl;

$R^{14}$, $R^{15}$, $R^{37}$, and $R^{38}$ are independently selected from the group consisting of hydrido, hydroxy, halo, alkyl, alkoxyalkyl, haloalkyl, haloalkoxy, and haloalkoxyalkyl;

$R^{14}$ and $R^{38}$ can be independently selected from the group consisting of aroyl and heteroaroyl;

Ψ is selected from the group consisting of $NR^5$, C(O), and S(O)$_2$;

$R^5$ is selected from the group consisting of hydrido, hydroxy, alkyl, and alkoxy;

$R^{39}$ and $R^{40}$ are independently selected from the group consisting of hydrido, hydroxy, halo, hydroxyalkyl, alkyl, alkoxyalkyl, haloalkyl, haloalkoxy, and haloalkoxyalkyl;

M is selected from the group consisting of N and $R^1$—C;

$R^1$ is selected from the group consisting of hydrido, alkyl, alkenyl, cyano, halo, haloalkyl, haloalkoxy, haloalkylthio, amino, aminoalkyl, alkylamino, amidino, guanidino, hydroxy, hydroxyamino, alkoxy, hydroxyalkyl, alkoxyamino, thiol, alkylthio, and phosphono;

$R^2$ is $Z^0$—Q;

$Z^0$ is selected from the group consisting of covalent single bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), S(O)$_2$, N($R^{41}$), and ON($R^{41}$), and $(CH(R^{41}))_e$—$W^{22}$—$(CH(R^{42}))_h$ wherein e and h are integers independently selected from 0 through 2 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^0$ is directly bonded to the pyrimidinone ring;

$R^{41}$ and $R^{42}$ are independently selected from the group consisting of amidino, hydroxyamino, hydrido, hydroxy, amino, and alkyl;

Q is selected from the group consisting of hydrido, with the proviso that $Z^0$ is other than a covalent single bond, the formula (II):

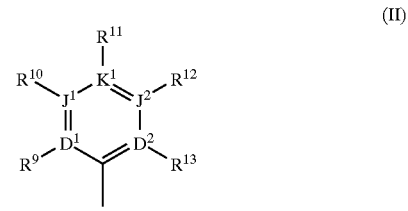

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ is N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $(CR^{4a}R^{4b})_n$ wherein n is an integer selected from 1 through 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^0$ is selected from the group consisting of a covalent single bond, C(O), C(S), C(O)N($R^7$), ($R^7$)NC(O), S(O)$_2$, ($R^7$)NS(O)$_2$, and S(O)$_2$N($R^7$);

$Y^0$ is formula (IV):

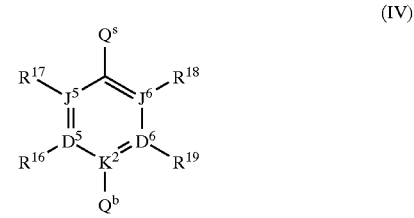

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$Q^b$ is selected from the group consisting of $NR^{20}R^{21}$, $^+NR^{20}R^{21}R^{22}$, aminoalkylenyl, and $Q^{be}$, wherein $Q^{be}$ is hydrido and $R^{20}$, $R^{21}$, and $R^{22}$ are independently selected from the group consisting of hydrido, alkyl, hydroxy, amino, aminoalkylenyl, dialkylamino, alkylamino, and hydroxyalkyl with the proviso that no more than one of $R^{20}$ and $R^{21}$ is hydroxy, amino, alkylamino, or dialkylamino at the same time;

$Q^b$ is optionally selected from the group consisting of $C(NR^{25})NR^{23}R^{24}$, $N(R^{26})C(NR^{25})N(R^{23})(R^{24})$, $C(O)N(R^{26})C(NR^{25})N(R^{23})(R^{24})$, $N(R^{26})N(R^{26})C(NR^{25})N(R^{23})(R^{24})$, and $ON(R^{26})C(NR^{25})N(R^{23})(R^{24})$ with the provisos that no more than one of $R^{23}$, $R^{24}$, and $R^{26}$ is hydroxy, alkylamino, amino, or dialkylamino when two of the group consisting of $R^{23}$, $R^{24}$, and $R^{26}$ are bonded to the same atom;

$R^{23}$, $R^{24}$, $R^{25}$, and $R^{26}$ are independently selected from the group consisting of hydrido, alkyl, hydroxy, amino, alkylenylamino, dialkylamino, alkylamino, and hydroxyalkyl;

$Q^s$ is selected from the group consisting of a single covalent bond, $(CR^{37}R^{38})_b$—$(W^0)_{az}$ wherein az is an integer selected from 0 through 1, b is an integer selected from 1 through 5, and $W^0$ is selected from the group consisting of O, C(O), S(O), S(O)$_2$, S(O)$_2$N($R^{14}$), $N(R^{14})S(O)_2$, and $N(R^{14})$, $(CH(R^{14}))_c$—$W^1$—$(CH(R^{15}))_d$ wherein c and d same integers independently selected from 1 through 4 and $W^1$ is selected from the group consisting of O, S, C(O), C(S), C(O)O, C(S)O, C(O)S, C(S)S, C(O)N($R^{14}$), $(R^{15})NC(O)$, C(S)N($R^{14}$), $(R^{14})NC(S)$, OC(O)N($R^{14}$), $(R^{14})NC(O)O$, SC(S)N($R^{14}$), $(R^{14})NC(S)S$, SC(O)N($R^{14}$), $(R^{14})NC(O)S$, OC(S)N($R^{14}$), $(R^{14})NC(S)O$, $N(R^{15})C(O)N(R^{14})$, $(R^{14})NC(O)N(R^{15})$, $N(R^{15})C(S)N(R^{14})$, $(R^{14})NC(S)N(R^{15})$, S(O), S(O)$_2$, S(O)$_2$N($R^{14}$), $N(R^{14})S(O)_2$, P(O)($R^8$), $N(R^7)P(O)(R^8)$, P(O)($R^8$)N($R^7$), $N(R^{14})$, ON($R^{14}$), and $(CH(R^{14}))_e$—$W^{22}$—$(CH(R^{15}))_h$ wherein e and h are integers independently selected from 0 through 2 and $W^{22}$ is selected from the group consisting of $CR^{41}=CR^{42}$, $CR^{41}R^{42}=C$; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, and $(CH(R^{14}))_e$ are bonded to $E^0$;

$Y^0$ is optionally $Q^b$—$Q^{ss}$ wherein $Q^{ss}$ is selected from the group consisting of $(CR^{37}R^{38})_f$ wherein f is an integer selected from 1 through 4, $(CH(R^{14}))_c$—$W^1$—$(CH(R^{15}))_d$ wherein c and d are integers independently selected from 1 through 2, and $W^1$ is selected from the group consisting of $W^1$ is selected from the group consisting of O, S, C(O), C(O)N($R^{14}$), $(R^{14})NC(O)$, $N(R^{15})C(O)N(R^{14})$, $(R^{14})NC(O)N(R^{15})$, $N(R^{14})$, ON($R^{14}$), and $(CH(R^{14}))_e$—$W^2$—$(CH(R^{15}))_h$ wherein e and h are integers independently selected from 0 through 2 and $W^2$ is selected from the group consisting of $CR^{4a}=CR^{4b}$, ethynylidene (C≡C; 1,2-ethynyl), and C≡$CR^{4a}R^{4b}$ with the provisos that $R^{14}$ and $R^{15}$ are selected from other than halo when directly bonded to N and that $(CR^{37}R^{38})_f$, $(CH(R^{14}))_c$, and $(CH(R^{14}))_e$ are bonded to $E^0$;

$Y^0$ is optionally $Q^b$—$Q^{sss}$ wherein $Q^{sss}$ is $(CH(R^{38}))_r$—$W^3$, r is an integer selected from 1 through 2, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, r is an integer selected from 1 through 2, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,5-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 2, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7- benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a) pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^o$;

$Y^o$ is optionally $Q^b$—$Q^{ssssr}$ wherein $Q^{ssssr}$ is $(CH(R^{38}))_r$—$W^6$, r is an integer selected from 1 through 2, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a) pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^o$.

In a preferred embodiment of compounds of Formula I or a pharmaceutically acceptable salt thereof, J is O;

B is the Formula:

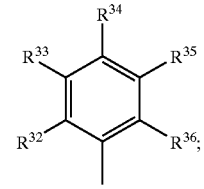

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, alkoxyalkyl, haloalkoxyalkyl, hydroxy, amino, alkoxyamino, nitro, lower alkylamino, alkylthio, alkylthioalkyl, alkylsulfinyl, alkylsulfonyl, alkylsulfonylalkyl, aryl, aralkyl, cycloalkyl, cycloalkylalkyl, alkylsulfonamido, alkylaminosulfonyl, amidosulfonyl, monoalkyl amidosulfonyl, dialkyl amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^9$, $R^{10}$, $R^{11}$, $R^{12}$, and $R^{13}$ are optionally selected from the group consisting of heteroaryl and heterocyclyl with the proviso that $R^9$, $R^{10}$, $R^{11}$, $R^{12}$, and $R^{13}$ are substitutents for other than B;

$R^{16}$, $R^{19}$, $R^{32}$, $R^{33}$, $R^{34}$, $R^{35}$, and $R^{36}$ are independently optionally $Q^b$ with the proviso that no more than one of $R^{16}$ and $R^{19}$ is $Q^b$ at the same time and that $Q^b$ is $Q^{be}$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is selected from the group consisting of C3–C12 cycloalkyl and C4-heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbons and a nitrogen adjacent to the carbon at the point of attachment may be optionally substituted with $R^9$ or $R^{13}$, a ring carbon or nitrogen adjacent to the $R^9$ position and two atoms from the point of attachment may be substituted with $R^{10}$, a ring carbon or nitrogen adjacent to the $R^{13}$ position and two atoms from the point of attachment may be substituted with $R^{12}$, a ring carbon or nitrogen three atoms from the point of attachment and adjacent to the $R^{10}$ position may be substituted with $R^{11}$, a ring carbon or nitrogen three atoms from the point of attachment and adjacent to the $R^{12}$ position may be substituted with $R^{33}$, and a ring carbon or nitrogen four atoms from the point of attachment and adjacent to the $R^{11}$ and $R^{33}$ positions may be substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), $(R^7)NC(O)$, $(R^7)NC(S)$, and $N(R^7)$ with the proviso that no more than one of the group consisting of rr and pa is 0 at the same time;

$R^7$ is selected from the group consisting of hydrido, hydroxy, and alkyl;

$R^{15}$ is selected from the group consisting of hydrido, hydroxy, halo, alkyl, and haloalkyl;

Ψ is selected from the group consisting of NH and NOH;

M is selected from the group consisting of N and $R^1$—C;

$R^1$ is selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$, and $(CH(R^{41}))_e$—$W^{22}$—$(CH(R^{42}))_h$ wherein e and h are integers independently selected from 0 through 1 and $W^{22}$ is selected from the group consisting of $CR^{41}=CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^0$ is directly bonded to the pyrimidinone ring;

$R^{41}$ and $R^{42}$ are independently selected from the group consisting of amidino, hydroxyamino, hydrido, hydroxy, amino, and alkyl;

Q is selected from the group consisting of hydrido, with the proviso that $Z^0$ is other than a covalent single bond, and the formula (II):

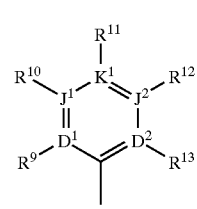

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $(CR^{4a}R^{4b})_n$ wherein n is an integer selected from 1 through 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^0$ is $E^1$, when K is $(CR^{4a}R^{4b})_n$, wherein $E^1$ is selected from the group consisting of a covalent single bond, C(O), C(S), $C(O)N(R^7)$, $(R^7)NC(O)$, $S(O)_2$, $(R^7)NS(O)_2$, and $S(O)_2N(R^7)$;

$Y^0$ is formula (IV):

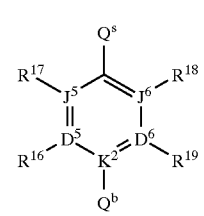

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N with the proviso that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, lower alkylamino, alkylthio, alkylsulfinyl, alkylsulfonyl, alkanoyl, haloalkanoyl, alkyl, alkenyl, halo, haloalkyl, haloalkoxy, hydroxyalkyl, alkylenylamino, haloalkoxyalkyl, carboalkoxy, and cyano;

$Q^b$ is selected from the group consisting of $NR^{20}R^{21}$, aminoalkylenyl, $Q^{be}$ wherein $Q^{be}$ is hydrido, $N(R^{26})C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, aminoalkylenyl, amino, dialkylamino, alkylamino, and hydroxyalkyl;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$, and $(CH(R^{14}))_c$ are bonded to $E^o$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally selected from the group consisting of aroyl and heteroaroyl;

$Y^o$ is optionally $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=$CR^{4b}$ with the proviso that $(CH(R^{14}))_e$ is bonded to $E^o$;

$Y^o$ is optionally selected from the group consisting of $Q^b$—$Q^{ssss}$ and $Q^b$—$Q^{ssssr}$ wherein $Q^{ssss}$ is $(CH(R^{38}))_r$—$W^5$ and $Q^{ssssr}$ $(CH(R^{38}))_r$—$W^6$, r is an integer selected from 1 through 2, and $W^5$ and $W^6$ are independently selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ and of the ring of the $W^6$, other than the points of attachment of $W^5$ and $W^6$, is optionally substituted with one or more of the group consisting of $R^9$, $R^{10}$, $R^{11}$, and $R^{12}$, with the provisos that $Q^b$ is bonded to lowest number substituent position of each $W^5$, $Q^b$ is bonded to highest number substituent position of each $W^6$, and $(CH(R^{38}))_r$ is bonded to $E^o$.

In a more preferred embodiment of compounds of Formula I or a pharmaceutically acceptable salt thereof, J is O;

B is the Formula:

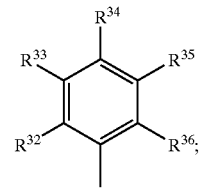

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, alkanoyl, haloalkanoyl, nitro, lower alkylamino, alkylthio, aryl, aralkyl, cycloalkyl, cycloalkylalkyl, alkylsulfonamido, amidosulfonyl, monoalkyl amidosulfonyl, dialkyl amidosulfonyl, alkyl, alkenyl, halo, haloalkyl, haloalkenyl, haloalkoxy, hydroxyalkyl, alkylenlyamino, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is selected from the group consisting of C3–C12 cycloalkyl and C4–heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbons and a nitrogen adjacent to the carbon at the point of attachment may be optionally substituted with $R^9$ or $R^{13}$, a ring carbon or nitrogen adjacent to the $R^9$ position and two atoms from the point of attachment may be substituted with $R^{10}$, a ring carbon or nitrogen adjacent to the $R^{13}$ position and two atoms from the point of attachment may be substituted with $R^{12}$, a ring carbon three atoms from the point of attachment and adjacent to the $R^{10}$ position may be substituted with $R^{11}$, a ring carbon three atoms from the point of attachment and adjacent to the $R^{12}$ position may be substituted with $R^{33}$, and a ring carbon four atoms from the point of attachment and adjacent to the $R^{11}$ and $R^{33}$ positions may be substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, hydroxy, amino, lower alkylamino, alkylthio, alkylsulfinyl, alkylsulfonyl, alkylsulfonamido, amidosulfonyl, monoalkyl amidosulfonyl, dialkyl amidosulfonyl, alkyl, halo, haloalkyl, haloalkoxy, hydroxyalkyl, aminoalkyl, carboalkoxy, carboxyalkyl, carboxy, carboxamido, and cyano;

$R^9$, $R^{10}$, $R^{11}$, $R^{12}$, and $R^{13}$ are optionally selected from the group consisting of heteroaryl and heterocyclyl with the proviso that $R^9$, $R^{10}$, $R^{11}$, $R^{12}$, and $R^{13}$ are substitutents for other than B;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

Ψ is NH;

M is selected from the group consisting of N and $R^1$—C;

$R^1$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$-Q;

$Z^0$ is selected from the group consisting of covalent single bond and $(CR^{41}R^{42})_q$ wherein q is an integer selected from 1 through 2, $(CH(R^{41}))_g$—$W^0$—$(CH(R^{42}))_p$ wherein g and p are integers independently selected from 0 through 3 and $W^0$ is selected from the group consisting of O, S, and $N(R^{41})$, and $(CH(R^{41}))_e$—$W^{22}$—$(CH(R^{42}))_h$ wherein e and h are integers independently selected from 0 through 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^0$ is directly bonded to the pyrimidinone ring;

$R^{41}$ and $R^{42}$ are independently selected from the group consisting of hydrido, hydroxy, and amino;

Q is selected from the group consisting of hydrido, with the proviso that $Z^0$ is other than a covalent single bond, aryl, and heteroaryl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CHR^{4a}$ wherein $R^{4a}$ is selected from the group consisting of hydrido, hydroxyalkyl, alkyl, alkoxyalkyl, alkylthioalkyl, and haloalkyl;

$E^0$ is selected from the group consisting of a covalent single bond, C(O)N(H), (H)NC(O), $(R^7)NS(O)_2$, and $S(O)_2N(R^7)$;

$Y^0$ is formula (IV):

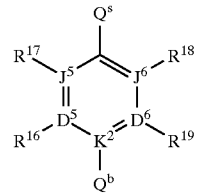

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a single covalent bond, $(CR^{37}R^{38})_b$ wherein b is an integer selected from 1 though 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, S(O), $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$, and $(CH(R^{14}))_c$ are bonded to $E^0$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally selected from the group consisting of aroyl and heteroaroyl;

$Y^0$ is optionally $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=CH with the proviso that $(CH(R^{14}))_e$ is bonded to $E^0$.

In an even more preferred embodiment of compounds of Formula I or a pharmaceutically acceptable salt thereof, J is O;

B is the Formula:

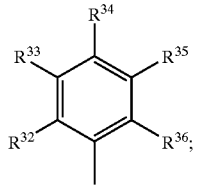

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl, and haloalkyl;

Ψ is NH;

M is selected from the group consisting of N and $R^1$—C;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o$—Q;

$Z^o$ is selected from the group consisting of a covalent single bond, O, S, NH, and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, aminoalkyl, carboalkoxy, carboxy, carboxyalkyl, amidocarbonyl, halo, haloalkyl, and cyano;

K is $CH_2$;

$E^o$ is $C(O)N(H)$;

$Y^o$ is formula (IV):

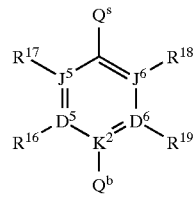

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is optionally O, no more than one of $D^5$, $D^6$, $J^5$, and $J^6$ is optionally S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In another even more preferred embodiment of compounds of Formula I or a pharmaceutically acceptable salt thereof, J is O;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl, and haloalkyl;

$\Psi$ is NH;

M is selected from the group consisting of N and $R^1$—C;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of covalent single bond, O, S, NH, and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, alkylenylamino, carboalkoxy, carboxy, carboxyalkyl, amidocarbonyl, halo, haloalkyl, and cyano;

K is $CH_2$;

$E^0$ is C(O)N(H);

$Y^0$ is formula (IV):

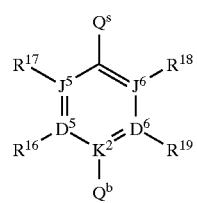

(IV)

wherein $D^5$, $D^6$, $J^5$, and $J^6$ are independently selected from the group consisting of C, N, O, S and a covalent bond with the provisos that no more than one is a covalent bond, $K^2$ is C, no more d none of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a single covalent bond, $CH_2$, and $CH_2CH_2$.

In still another even more preferred embodiment of compounds of Formula I or a pharmaceutically acceptable salt thereof, J is O;

B is selected from the group consisting of C3–C7 cycloalkyl and C4-heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbons and a nitrogen adjacent to the carbon at the point of attachment may be optionally substituted with $R^9$ or $R^{13}$, a ring carbon or nitrogen adjacent to the $R^9$ position and two atoms from the point of attachment may be substituted with $R^{10}$, a ring carbon or nitrogen adjacent to the $R^{13}$ position and two atoms from the point of attachment may be substituted with $R^{12}$, a ring carbon three atoms from the point of attachment and adjacent to the $R^{10}$ position may be substituted with $R^{11}$, a ring carbon three atoms from the point of attachment and adjacent to the $R^{12}$ position may be substituted with $R^{33}$, and a ring carbon four atoms from the point of attachment and adjacent to the $R^{11}$ and $R^{33}$ positions may be substituted with $R^{34}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, alkylenylamino, carboalkoxy, carboxy, carboxyalkyl, amidocarbonyl, halo, haloalkyl, and cyano;

$R^{33}$ and $R^{34}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl, and haloalkyl;

Ψ is NH;

M is selected from the group consisting of N and $R^1$—C;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of covalent single bond, O, S, NH, and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CH_2$;

$E^0$ is $C(O)N(H)$;

$Y^0$ is formula (IV):

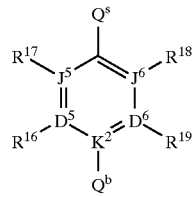

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of, $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In a most preferred embodiment of compounds of Formula I or a pharmaceutically acceptable salt thereof, J is O;

B is the Formula:

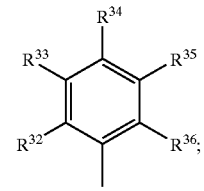

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

Ψ is NH;

M is selected from the group consisting of N and $R^1$—C;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

K is $CH_2$;

$E^0$ is C(O)N(H);

$Y^0$ is formula (IV):

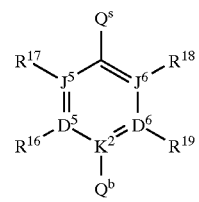

(IV)

wherein $D^5$, $D^6$, $J_5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$;

$R^{20}$, $R^{21}$, $R^{23}$, $R^{24}$, and $R^{25}$ are independently selected from the group consisting of hydrido and alkyl;

$Q^s$ is $CH_2$.

In another most preferred embodiment of compounds of Formula I or a pharmaceutically acceptable salt thereof, J is O;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}-(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

Ψ is NH;

M is selected from the group consisting of N and $R^1$—C;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

K is $CH_2$;

$E^0$ is C(O)N(H);

$Y^0$ is formula (IV):

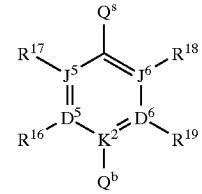

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$;

$R^{20}$, $R^{21}$, $R^{23}$, $R^{24}$, $R^{25}$, and $R^{26}$ are independently selected from the group consisting of hydrido and alkyl;

$Q^s$ is $CH_2$.

In still another most preferred embodiment of compounds of Formula I or a pharmaceutically acceptable salt thereof, J is O;

B is selected from the group consisting of C3–C7 cycloalkyl and C4-heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbons and nitrogens adjacent to the carbon at the point of attachment may be optionally substituted with $R^9$ or $R^{13}$, a ring carbon or nitrogen adjacent to the $R^9$ position and two atoms from the point of attachment may be substituted with $R^{10}$, a ring carbon or nitrogen adjacent to the $R^{13}$ position and two atoms from the point of attachment may be substituted with $R^{12}$, a ring carbon three atoms from the point of attachment and adjacent to the $R^{10}$ position may be substituted with $R^{11}$, a ring carbon three atoms from the point of attachment and adjacent to the $R^{12}$ position may be substituted with $R^{33}$, and a ring carbon four atoms from the point of attachment and adjacent to the $R^{11}$ and $R^{33}$ positions may be substituted with $R^{34}$;

$R^9$, $R^{11}$, and $R^{13}$ are independently selected from the group consisting of hydrido, hydroxy, amino, amidino, guanidino, lower alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

$R^{33}$ and $R^{34}$ are independently selected from the group consisting of hydrido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, and cyano;

$R^{33}$ is optionally $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrido, hydroxy and alkyl;

$R^{15}$ is selected from the group consisting of hydrido, halo, alkyl, and haloalkyl;

Ψ is NH;

M is selected from the group consisting of N and $R^1$—C;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CH_2$;

$E^0$ is C(O)N(H);

$Y^0$ is formula (IV):

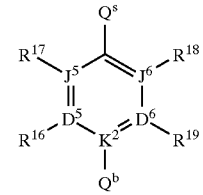

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than on of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$;

$R^{20}$, $R^{21}$, $R^{23}$, $R^{24}$, and $R^{25}$ are independently selected from the group consisting of hydrido and alkyl;

$Q^s$ is $CH_2$.

In a preferred specific embodiment of Formula I, compounds have the Formula I-S:

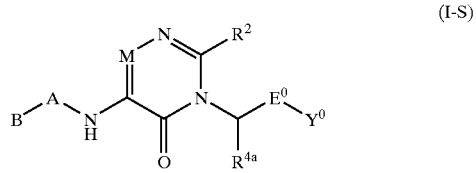

(I-S)

or a pharmaceutically acceptable salt thereof, wherein;

B is the Formula:

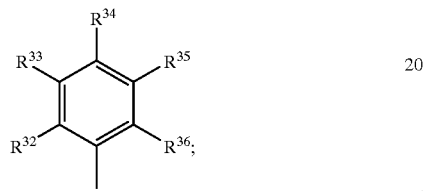

$R^{32}$, $R^{33}$, $R^{34}$, $R^{35}$, and $R^{36}$ independently selected from the group consisting of hydrido, amidino, guanidino, carboxy, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, cyano, and $Q^b$;

B is selected from the group consisting of hydrido, trimethylsilyl, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 1-octyl, 2-octenyl, 3-octenyl, 4-octenyl, 5-octenyl, 6-octenyl, 7-octenyl, 2-octynyl, 3-octynyl, 4-octynyl, 5-octynyl, 6-octynyl, 2-octyl, 1-methyl-2-heptenyl, 1-methyl-3-heptenyl, 1-methyl-4-heptenyl, 1-methyl-5-heptenyl, 1-methyl-6-heptenyl, 1-methyl-2-heptynyl, 1-methyl-3-heptynyl, 1-methyl-4-heptynyl, 1-methyl-5-heptynyl, 1-methyl-6-heptynyl, 1-methyl-2-heptenyl, 1-methyl-3-heptynyl, 1-methyl-4-heptynyl, 1-methyl-5-heptynyl, 3-octyl, 1-ethyl-2-hexenyl, 1-ethyl-3-hexenyl, 1-ethyl-4-hexenyl, 1-ethyl-2-hexynyl, 1-ethyl-3-hexynyl, 1-ethyl-4-hexynyl, 1-ethyl-5-hexenyl, 1-pentyl-2-propenyl, 4-octyl, 1-propyl-2-pentenyl, 1-propyl-3-pentenyl, 1-propyl-4-pentenyl, 1-butyl-2-butenyl, 1-propyl-2-pentynyl, 1-propyl-3-pentynyl, 1-butyl-2-butynyl, 1-butyl-3-butenyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

B is optionally selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, cyclopentyl, cyclohexyl, adamantyl, norbornyl, 3-trifluoromethylnorbornyl, bicyclo[3.1.0]hexan-6-yl, cycloheptyl, and cyclooctyl, wherein each ring carbon is optionally substituted with $R^{33}$, ring carbons or a nitrogen adjacent to the carbon atom at the point of attachment is optionally substituted with $R^9$ or $R^{13}$, a ring carbon or a nitrogen adjacent to the $R^9$ position and two atoms from the point of attachment is optionally substituted with $R^{10}$, and a ring carbon or a nitrogen adjacent to the $R^{13}$ position and two atoms from the point of attachment is optionally substituted with $R^{12}$;

$R^9$, $R^{10}$, $R^{11}$, $R^{12}$, and $R^{13}$ are independently selected from the group consisting of hydrido, amidino, guanidino, carboxy, carboxymethyl, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, and cyano;

A is selected from the group consisting of single covalent bond, O, S, NH, $N(CH_3)$, $N(OH)$, $C(O)$, $CH_2$, $CH_3CH$, $CF_3CH$, $NHC(O)$, $N(CH_3)C(O)$, $C(O)NH$, $C(O)N(CH_3)$, $CF_3CC(O)$, $C(O)CCH_3$, $C(O)CCF_3$, $CH_2C(O)$, (O)CCH₂, CH₂CH₂, CH₂CH₂CH₂, CH₃CHCH₂, CF₃CHCH₂, CH₃CC(O)CH₂, CF₃CC(O)CH₂, CH₂C(O)CCH₃, CH₂C(O)CCF₃, CH₂CH₂C(O), and CH₂(O)CCH₂;

A is optionally selected from the group consisting of CH₂N(CH₃), CH₂N(CH₂CH₃), CH₂CH₂N(CH₃), and CH₂CH₂N(CH₂CH₃) with the proviso that B is hydrido;

M is selected from the group consisting of N and R¹—C;

R¹ is selected from the group consisting of hydrido, hydroxy, amino, thiol, amidino, hydroxyamino, aminomethyl, 1-aminoethyl, 2-aminoethyl, methylamino, dimethylamino, cyano, methyl, ethyl, isopropyl, propyl, trifluoromethyl, pentafluoroethyl, 2,2,2-trifluoroethyl, 2,2,3,3,3-pentafluoropropyl, methoxy, ethoxy, propoxy, hydroxymethyl, 1-hydroxyethyl, 2-hydroxyethyl, methoxyamino, ethoxyamino, methylthio, ethylthio, trifluoromethoxy, 1,1,2,2-tetrafluoroethoxy, fluoro, chloro, and bromo;

R² is Z⁰—Q;

Z⁰ is selected from the group consisting of covalent single bond, O, S, NH, CH₂, CH₂CH₂, CH(OH), CH(NH₂), CH₂CH(OH), CH₂CHNH₂, CH(OH)CH₂, and CH(NH₂)CH₂;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, wherein a carbon adjacent to the carbon at the point of attachment is optionally substituted by R⁹, the other carbon adjacent to the carbon at the point of attachment is optionally substituted by R¹³, a carbon adjacent to R⁹ and two atoms from the carbon at the point of attachment is optionally substituted by R¹⁰, a carbon adjacent to R¹³ and two atoms from the carbon at the point of attachment is optionally substituted by R¹², and any carbon adjacent to both R¹⁰ and R¹² is optionally substituted by R¹¹;

K is CHR⁴ᵃ wherein R⁴ᵃ is selected from the group consisting of methyl, ethyl, propyl, isopropyl, hydroxymethyl, 1-hydroxyethyl, methoxymethyl, trifluoromethyl, pentafluoroethyl, 2,2,2-trifluoromethyl, methylthiomethyl, and hydrido;

E⁰ is a covalent single bond, C(O)N(H), (H)NC(O), and S(O)₂N(H);

Y⁰ is selected from the group of formulas consisting of:

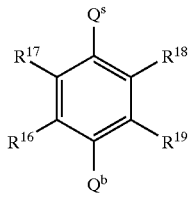
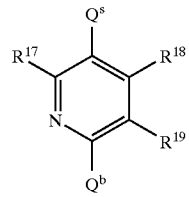

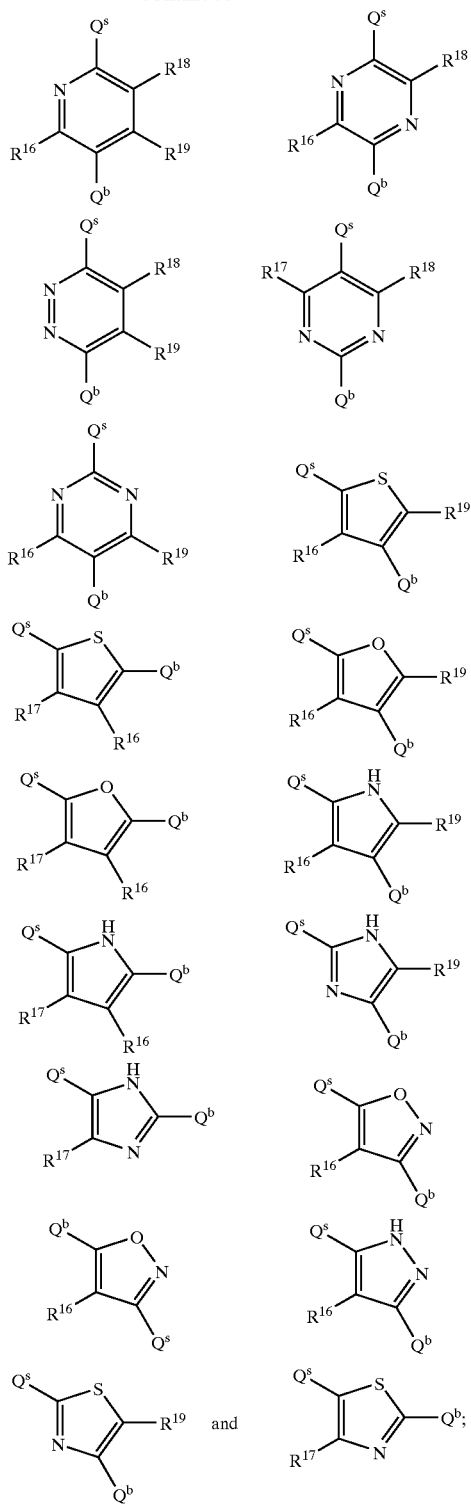

R¹⁶, R¹⁷, R¹⁸, and R¹⁹ are independently selected from the group consisting of hydrido, methyl, ethyl, isopropyl, propyl, amidino, guanidino, carboxy, methoxy, ethoxy, isopropoxy, propoxy, hydroxy, amino, methoxyamino, ethoxyamino, aminomethyl, 1-aminoethyl, 2-aminoethyl, N-N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $C(NR^{25})NR^{23}R^{24}$ and $N(R^{26})C(NR^{25})N(R^{23})(R^{24})$, with the proviso that no more than one of $R^{20}$ and $R^{21}$ is hydroxy, N-methylamino, and N,N-dimethylamino at the same time and that no more than one of $R^{23}$ and $R^{24}$ is hydroxy, N-methylamino, and N,N-dimethylamino at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, hydroxy, 2-aminoethyl, 2-(N-methylamino)ethyl, and 2-(N,N-dimethylamino)ethyl;

$Q^s$ is selected from the group consisting of a single covalent bond, $CH_2$, $CH_2CH_2$, $CH_3CH$, $CF_3CH$, $CH_3CHCH_2$, $CF_3CHCH_2$, $CH_2(CH_3)CH$, $CH=CH$, $CF=CH$, $C(CH_3)=CH$, $CH=CHCH_2$, $CF=CHCH_2$, $C(CH_3)=CHCH_2$, $CH_2CH=CH$, $CH_2CF=CH$, $CH_2C(CH_3)=CH$, $CH_2CH=CHCH_2$, $CH_2CF=CHCH_2$, $CH_2C(CH_3)=CHCH_2$, $CH_2CH=CHCH_2CH_2$, $CH_2CF=CHCH_2CH_2$, and $CH_2C(CH_3)=CHCH_2CH_2$.

In a more preferred specific embodiment of Formula I, compounds have the Formula I-MPS wherein B is an aromatic;

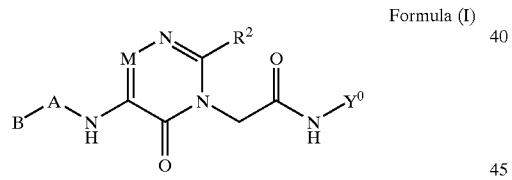

Formula (I)

(I-MPS wherein B is aromatic)
or a pharmaceutically acceptable salt thereof, wherein;
B is the Formula:

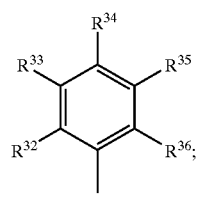

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-methylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, $N(CH_3)$, $N(OH)$, $CH_2$, $CH_3CH$, $CF_3CH$, $NHC(O)$, $N(CH_3)C(O)$, $C(O)NH$, $C(O)N(CH_3)$, $CH_2CH_2$, $CH_2CH_2CH_2$, $CH_3CHCH_2$, and $CF_3CHCH_2$;

$Q^b$ is selected from the group consisting of $NR^{20}R^{21}$, $Q^{be}$ wherein $Q^{be}$ is hydrido, and $C(NR^{25})NR^{23}R^{24}$, with the provisos that no more than one of $R^{20}$ and $R^{21}$ is hydroxy at the same time and that more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, methyl, ethyl, propyl, butyl, isopropyl, and hydroxy;

$Q^s$ is selected from the group consisting of a single covalent bond, $CH_2$, and $CH_2CH_2$.

In another more preferred specific embodiment of Formula I, compounds have the Formula I-MPS wherein B is a non-cyclic substituent:

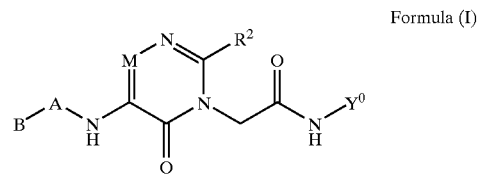

Formula (I)

(I-MPS wherein B is a non-cyclic substituent)
or a pharmaceutically acceptable salt thereof, wherein;
B is selected from the group consisting of hydrido, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, N(CH$_3$), N(OH), CH$_2$, CH$_3$CH, CF$_3$CH, NHC(O), N(CH$_3$)C(O), C(O)NH, C(O)N(CH$_3$), CH$_2$CH$_2$, CH$_2$CH$_2$CH$_2$, CH$_3$CHCH$_2$, and CF$_3$CHCH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

$Q^b$ is selected from the group consisting of NR$^{20}$R$^{21}$, $Q^{be}$, wherein $Q^{be}$ is hydrido, C(NR$^{25}$)NR$^{23}$R$^{24}$, and N(R$^{26}$)C(NR$^{25}$)N(R$^{23}$)(R$^{24}$), with the provisos that no more than one of R$^{23}$ and R$^{24}$ is hydroxy at the same time and that no more than one of R$^{23}$ and R$^{24}$ is hydroxy at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy;

$Q^s$ is selected from the group consisting of a single covalent bond, CH$_2$, and CH$_2$CH$_2$.

In still another more preferred specific embodiment of Formula I, compounds have the Formula I-MPS wherein B is a non-aromatic cyclic substituent:

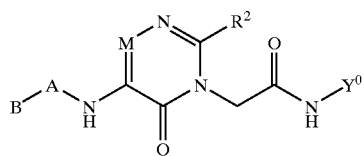

Formula (I)

(I-MPS wherein B is a non-aromatic cyclic substituent) or a pharmaceutically acceptable salt thereof, wherein;

B is optionally selected from the group consisting of cyclopropyl, cyclobutyl, oxetan-3-yl, azetidin-1-yl, azetidin-2-yl, azetidin-3-yl, thiaetan-3-yl, cyclopentyl, cyclohexyl, norbornyl, bicyclo[3.1.0]hexan-6-yl, and cycloheptyl, wherein each ring carbon is optionally substituted with R$^{33}$, ring carbons or a nitrogen adjacent to the carbon atom at the point of attachment is optionally substituted with R$^9$ or R$^{13}$, a ring carbon or nitrogen adjacent to the R$^9$ position and two atoms from the point of attachment is optionally substituted with R$^{10}$, and a ring carbon or nitrogen adjacent to the R$^{13}$ position and two atoms from the point of attachment is optionally substituted with R$^{12}$;

A is selected from the group consisting of single covalent bond, NH, N(CH$_3$), N(OH), CH$_2$, CH$_3$CH, CF$_3$CH, NHC(O), N(CH$_3$)C(O), C(O)NH, C(O)N(CH$_3$), CH$_2$CH$_2$, CH$_2$CH$_2$CH$_2$, CH$_3$CHCH$_2$, and CF$_3$CHCH$_2$;

$R^{33}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

$Q^b$ is selected from the group consisting of NR$^{20}$R$^{21}$, $Q^{be}$ wherein $Q^{be}$ is hydrido, and C(NR$^{25}$)NR$^{23}$R$^{24}$, with the provisos that no more than one of R$^{20}$ and R$^{21}$ is hydroxy at the same time and that no more than one of R$^{23}$ and R$^{24}$ is hydroxy at the same time;

$R^{20}$, $R^{21}$, $R^{23}$, $R^{24}$, and $R^{25}$ are independently selected from the group consisting of hydrido, methyl, ethyl, propyl, butyl, isopropyl, and hydroxy;

$Q^s$ is selected from the group consisting of a single covalent bond, CH$_2$, ant CH$_2$CH$_2$.

The more preferred specific embodiment (I-MPS) compounds of the present invention having the Formula:

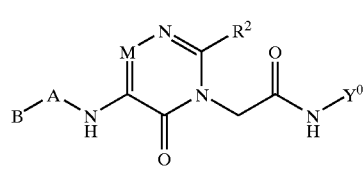

Formula (I)

or a pharmaceutically acceptable salt thereof, have common structural units, wherein;

M is selected from the group consisting of N and R$^1$—C;

$R^1$ is selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^0$—Q;

$Z^0$ is selected from the group consisting of covalent single bond, O, S, NH, and CH$_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by R$^9$, the other carbon adjacent to the carbon at the point of attachment is optionally substituted by R$^{13}$, a carbon adjacent to R$^9$ and two atoms from the carbon at the point of attachment is optionally substituted by R$^{10}$, a carbon adjacent to R$^{13}$ and two atoms from the carbon at the point of attachment is optionally substituted by R$^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, fluoro, chloro, bromo, and cyano;

$Y^o$ is selected from the group of formulas consisting of:

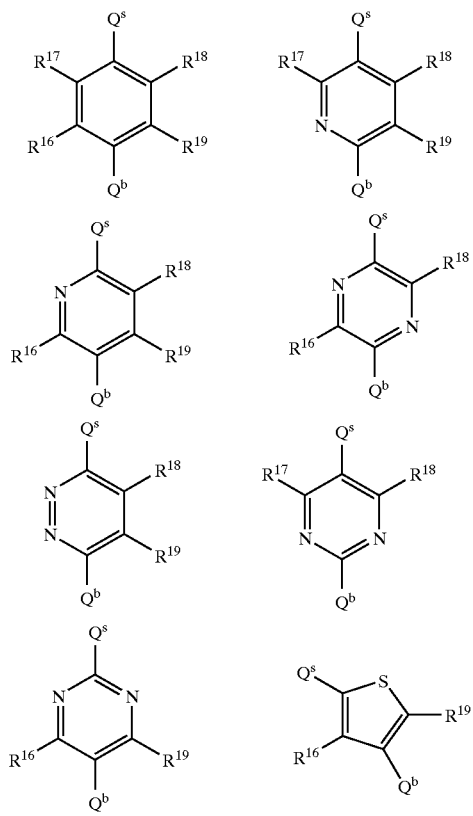
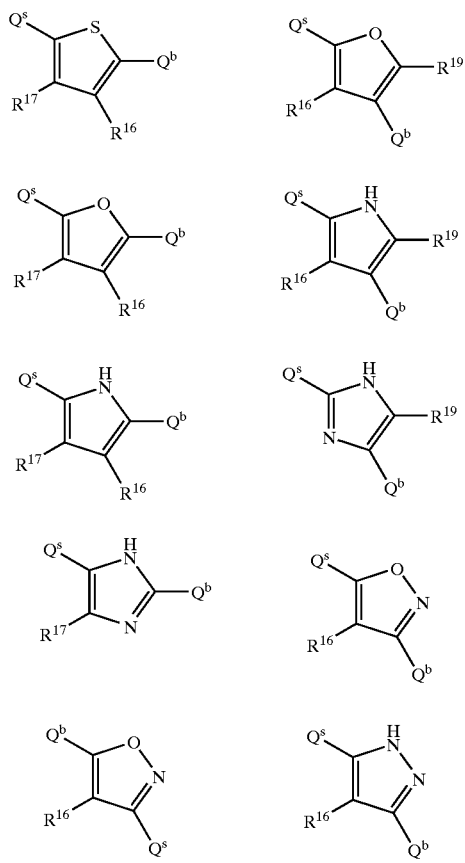
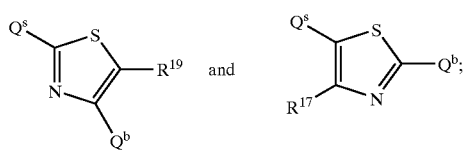

and $R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$.

In a most preferred specific embodiment of Formula I, compounds have the Formula I-EMPS wherein B is an aromatic;

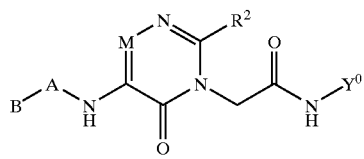

Formula (I)

(I-EMPS where B is aromatic)
or a pharmaceutically acceptable salt thereof, wherein;
B is the Formula:

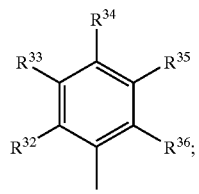

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, $N(CH_3)$, $CH_2$, $CH_3CH$, and $CH_2CH_2$;

$Q^b$ is selected from the group consisting of $NR^{20}R^{21}$ and $C(NR^{25})NR^{23}R^{24}$, with the proviso that said $Q^b$ group is bonded directly to a carbon atom;

$R^{20}$, $R^{21}$, $R^{23}$, $R^{24}$, and $R^{25}$ are independently selected from the group consisting of hydrido, methyl, and ethyl;

$Q^s$ is $CH_2$.

In another most preferred specific embodiment of Formula I, compounds have the Formula I-EMPS wherein B is a non-cyclic substituent;

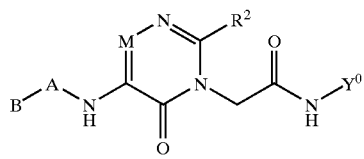

Formula (I)

(I-EMPS wherein B is a non-cyclic substituent)
or a pharmaceutically acceptable salt thereof, wherein;
B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, $N(CH_3)$, $CH_2$, $CH_3CH$, and $CH_2CH_2$;

A is optionally selected from the group consisting of $CH_2N(CH_3)$, $CH_2N(CH_2CH_3)$, $CH_2CH_2N(CH_3)$, and $CH_2CH_2N(CH_2CH_3)$ with the proviso that B is hydrido;

$Q^b$ is selected from the group consisting of $NR^{20}R^{21}$, $C(NR^{25})NR^{23}R^{24}$, and $N(R^{26})C(NR^{25})N(RF^{23})(R^{24})$, with the proviso that said $Q^b$ group is bonded directly to a carbon atom;

$R^{20}$, $R^{21}$, $R^{23}$, $R^{24}$, $R^{25}$, and $R^{26}$ are independently selected from the group consisting of hydrido, methyl, and ethyl;

$Q^s$ is $CH_2$.

In still another most preferred specific embodiment of Formula I, compounds have the Formula I-EMPS wherein B is a non-aromatic cyclic substituent:

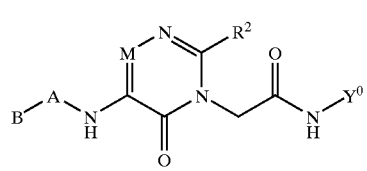

Formula (I)

(I-EMPS wherein B is a Non-aromatic Cyclic Substituent)
or a pharmaceutically acceptable salt thereof, wherein;
B is optionally selected from the group consisting of cyclopropyl, cyclobutyl, oxetan-3-yl, azetidin-3-yl, thiaetan-3-yl, cyclopentyl, and cyclohexyl, wherein each ring carbon is optionally substituted with $R^{33}$, ring carbons or a nitrogen adjacent to the carbon atom at the point of attachment is optionally substituted with $R^9$ or $R^{13}$, a ring carbon or nitrogen adjacent to the $R^9$ position and two atoms from the point of attachment is optionally substituted with $R^{10}$, and a ring carbon or nitrogen adjacent to the $R^{13}$ position and two atoms from the point of attachment is optionally substituted with $R^{12}$;

$R^{33}$ are independently selected from the group consisting of hydrido, amidino, guanidino, methyl, ethyl, methoxy, ethoxy, hydroxy, carboxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, cyano, and $Q^b$;

A is selected from the group consisting of single covalent bond, NH, N(CH$_3$), CH$_2$, CH$_3$CH, and CH$_2$CH$_2$;

Q$^b$ is selected from the group consisting of NR$^{20}$R$^{21}$ and C(NR$^{25}$)NR$^{23}$R$^{24}$, with the proviso that said Q$^b$ group is bonded directly to a carbon atom;

R$^{20}$, R$^{21}$, R$^{23}$, R$^{24}$, and R$^{25}$ are independently selected from the group consisting of hydrido, methyl, and ethyl;

Q$^s$ is CH$_2$.

The most preferred specific embodiment (I-EMPS) compounds of the present invention having the Formula:

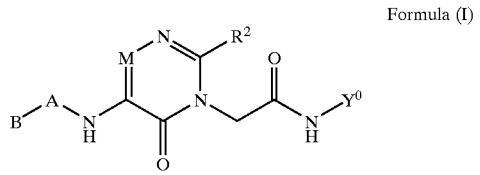

Formula (I)

or a pharmaceutically acceptable salt thereof, have common structural units, wherein;

M is selected from the group consisting of N and R$^1$-C;

R$^1$ is selected from the group consisting of hydrido, hydroxy, amino, amidino, hydroxyamino, aminomethyl, methylamino, cyano, methyl, trifluoromethyl, methoxy, hydroxymethyl, methoxyamino, methylthio, trifluoromethoxy, fluoro, and chloro;

R$^2$ is Z$^0$-Q;

Z$^0$ is a covalent single bond;

Q is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment is optionally substituted by R$^9$, the other carbon adjacent to the carbon at the point of attachment is optionally substituted by R$^{13}$, a carbon adjacent to R$^9$ and two atoms from the carbon at the point of attachment is optionally substituted by R$^{10}$, a carbon adjacent to R$^{13}$ and two atoms from the carbon at the point of attachment is optionally substituted by R$^{12}$, and any carbon adjacent to both R$^{10}$ and R$^{12}$ is optionally substituted by R$^{11}$;

R$^9$, R$^{11}$, and R$^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

R$^{10}$ and R$^{12}$ are independently selected from the group consisting of hydrido, amidino, amidocarbonyl, N-methylamidocarbonyl, guanidino, methyl, ethyl, methoxy, ethoxy, hydroxy, hydroxyethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, amidosulfonyl, N-methylamidosulfonyl, N,N-dimethylamidosulfonyl, methoxycarbonyl, fluoro, chloro, bromo, and cyano;

Y$^0$ is selected from the group of formulas consisting of:

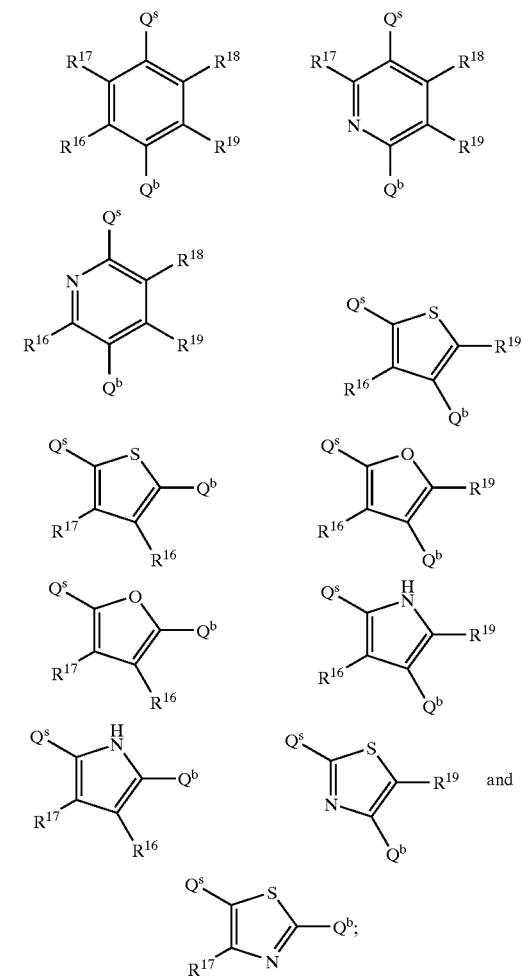

R$^{16}$, R$^{17}$, R$^{18}$, and R$^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, amidosulfonyl, N-methylamidosulfonyl, hydroxymethyl, carboxy, and cyano.

The compounds of this invention can be used in anticoagulant therapy for the treatment and prevention of a variety of thrombotic conditions including coronary artery and cerebrovascular disease. The compounds of this invention can be used to inhibit serine protease associated with the coagulation cascade and factors II, VII, VIII, IX, X, XI, or XII. The compounds of the invention can inhibit the formation of blood platelet aggregates, inhibit the formation of fibrin, inhibit thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of canalized vessels in a mammal. The compounds can also be used in prophylactic treatment of subjects who are at risk of developing such disorder. The compounds can be used to lower the risk of atherosclerosis. The compounds of Formula (I) would also be useful in prevention of cerebral vascular accident (CVA) or stroke.

Besides being useful for human treatment, these compounds are also useful for veterinary treatment of companion animals, exotic animals and farm animals, including mammals, rodents, and the like. More preferred animals include horses, dogs, and cats.

In yet another embodiment of the present invention, the novel compounds are selected from the compounds set forth in Examples 1 through Example 19 and Tables 1.

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrido atom. Double letter elemental symbols are used as defined for the elements of the periodical table (i.e., Cl represents chlorine, Se represents selenium, etc.).

As utilized herein the term "alkyl", either alone or within other terms such as "haloalkyl" and "alkylthio", means an acyclic alkyl radical containing from 1 to about 10, preferably from 3 to about 8 carbon atoms and more preferably 3 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 3 to about 8 carbon atoms and more preferably 3 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 3 to about 8 carbon atoms and more preferably having 3 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical —CH=, or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxykyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene (CH$_2$=C), 1,2-vinylidene (—CH=CH—), and 1,4-butadienyl (—CH=CH—CH=CH=).

The term "halo" means halogens such as fluorine, chlorine, bromine or iodine atoms.

The term "haloalkyl" embraces radicals wherein any one or more of the alkyl carbon atoms is substituted with halo as defied above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloroethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydroxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "lower haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "lower alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tefrafluoroethoxy, pentafluoroethoxy, and fluoropropoxy. Examples of such haloalkoxyalkyl radicals include fluoromethoxymethyl, chloromethoxyethyl, trifluromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "lower alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to forn monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoethylenedioxy, tetrachloroethylenedioxy, alkylsubstituted monofluoromethylenedioxy, and arylsubstituted monofluoromethylenedioxy.

The term "aryl", alone or in combination, means a cabocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heteocyclyl" embraces saturated and partially saturated heteroatom-containing ring-shaped radicals having from 4 though 15 ring members, herein referred to as "C4–C15 heterocyclyl" selected from carbon, nitrogen, sulfur and oxygen, wherein at least one ring atom is a heteroatom. Heteocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heteocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like.

The term "heteroaryl" embraces fully unsaturated heteroatom-containing ring-shaped aromatic radicals having from 5 through 15 ring members selected from carbon, nitrogen, sulfur and oxygen, wherein at least one ring atom is a heteroatom. Heteroaryl radicals may contain one, two or three rings wherein such rings may be attached in a pendant manner or may be fused. Examples of "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3triazolyl, 2H-1,2,3-triazolyl, etc.] tetrazolyl [e.g. 1H-tetrazolyl, 2H-tetrazolyl, etc.]. etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyctic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzotiophene, and the like.

Said "heterocyclyl" group may have 1 to 3 substituents as defined below. Pref red heterocyclic radicals include five to twelve membered fused or unfused radicals. Non-limiting examples of heteroaryl radicals include pyrrolyl, pyridinyl, pyridyloxy, pyrazolyl, triazolyl, pyrimidinyl, pyridazinyl, oxazolyl, thiazolyl, imidazolyl, indolyl, thiophenyl, furanyl, tetrazolyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, pyrazinyl, piperazinyl, 1,3,5-triazinyl, 1,3,5-trithianyl, benzo(b)thiophenyl, benzimidazolyl, quinolinyl, tetraazolyl, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals aced to a sulfonyl radical, where haloalkyl is defined as above. "Haloalkylsulfonylalkyl", embraces haloalkylsulfonyl radicals attached to an alkyl radical, where alkyl is defined as above. The term "aminosulfonyl" denotes an amino radical attached to a sulfonyl radical.

The term "sulfinyl", whether used alone or linked to other terms such as alkylsulfinyl, denotes respetively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfonyl radicals attached to an alkyl radical, where alkyl is defined as above.

The term "aralkyl" embraces aryl-substituted alkyl radicals. Preferable aralkyl radicals are "lower aralkyl" radicals having aryl radicals attached to alkyl radicals having one to six carbon. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additional substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to 15 carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term cycloalkyl embraces radicals having seven to 15 carbon atoms and having two to four rings. Examples include radicals such as norbornyl (i.e., bicyclo[2.2.1]heptyl) and adamantyl. The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "lower cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "lower halocycloalkyl" radicals having three to about eight carbon atoms. Examples of such halocycloalkyl radicals include fluorocyclopropyl, difluorocyclobutyl, trifluorocyclopentyl, tetrafluoroclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals.

The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycoakylsulfinylalkyl". embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocabonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. An example of "lower alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difloromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The terms alkylamino denotes "monoalkylamino" and "dialkylamino" containing one or two alkyl radicals, respectively, attached to an amino radical.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The team "heteroarylsulfinyl" embraces radicals containing an heteroaryl radical, as defined above, attached to a divalent S(O) atom. The term "heteroarylsulfinylalkyl" denotes heteroarylsulfinyl radicals attached to a linear or branched alkyl radical, of one to ten carbon atoms. The term "Heteroarylsulfonyl", embraces hetoaryl radicals attached to a sulfonyl radical, where heteroaryl is defined as above. "Heteroarylsulfonylalkyl", embraces heteroalsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluomethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyopropylphenoxy, 3-ethylphenoxy, 3-pentafluoroethylphenoxy, 3-(1,1,2,2-tetrafluoroethoxy)-phenoxy, and 4-tert-butylphenoxy.

The term "aroyl" embraces aryl radicals, as defined above, attached to an carbonyl radical as defined above. Examples of such radicals include benzoyl and toluoyl.

The terms "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. Examples of such radicals include benzyloxy, 1-phenylethoxy, 3-trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "hal aryloxyalkyl" embraces aryloxyalkyl radicals, as defined above, wherein one to five halo radicals are attached to an aryloxy group.

The term "heroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroralkoxy" embraces oxycontaining heteroarlkyl radicals attached through an oxygen atom to other radicals. More preferred heteroaralkoxy radicals are "lower heteroaralkoxy" radicals having heteroaryl radicals attached to lower alkoxy radical as described above.

The term "haloheteroaryloxyalkyl" embraces heteroaryloxyalkyl radicals, as defined above, wherein one to four halo radicals are attached to an heteroaryloxy group.

The term "heteroarylamino" embraces heteocyclyl radicals, as defined above, attached to an amino group. Examples of such radicals include pyridylamino.

The term "hetearoylaminoalkyl" embraces heteroaylamino radicals, as defined above, attached to an alkyl group. Examples of such radicals include pyridylmethylamino.

The term "heteroaryloxyalkyl" embraces heterocyclyl radicals, as defined above, attached to an oxy group. Examples of such radicals include 2-thiophenyloxy, 2-pyrimidyloxy, 2-pyridyloxy, 3-pyridyloxy, and 4-pyridyloxy.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Example of such radicals include methoxymethyl.

The term "carbonyl" denotes a carbon radical having two of the four covalent bonds shared with an oxygen atom. The term "carboxy" embraces a hydroxyl radical, as defined above, attached to one of two unshaved bonds in a carbonyl group. The term "carboxamide" embraces amino, monoalkylamino, dialkylamino, monocycloalkylamino, alkylcycloalkylamino, and dicycloalkylamino radicals, attached to one of two unshaved bonds in a carbonyl group. The term "carboxamidoalkyl" embraces carboxamide radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Example of "acyl" are formyl, acetyl, benzoyl, trifluoroacetyl, phthaloyl, malonyl, nicotinyl, and the like. The term "haloalkanoyl" embraces one or more halo radical, as defined herein, attached to alkanoyl radical as defined above. Examples of such radicals include, for example, chloroacetyl, trifluoroacetyl, bromopropanoyl, and heptafluorobutanoyl.

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

The term "amino" denotes a nitrogen atom containing two substituents such as hydrido, hydroxy or alkyl and having one covalent bond available for bonding to a single atom such as carbon. Examples of such amino radicals include, for example, $-NH_2$, $-NHCH_3$, $-NHOH$, and $-NHOCH_3$. The term "imino" denotes a nitrogen atom containing one substituent such as hydrido, hydroxy or alkyl and having two covalent bonds available for bonding to a single atom such as carbon. Examples of such imino radicals include, for example, $=NH$, $=NCH_3$, $=NOH$, and $=NOCH_3$. The term "imino carbonyl" denotes a carbon radical having two of the four covalent bond sites shared with an imino group. Examples of such imino carbonyl radicals include, for example, $C=NH$, $C=NCH_3$, $C=NOH$, and $C=NOCH_3$. The term "amidino" embraces a substituted or unsubstituted amino group bonded to one of two available bonds of an ininocarbonyl radical. Examples of such amidino radicals include, for example, $NH_2-C=NH$, $NH_2-C=NCH_3$, $NH_2-C=NOCH_3$ and $CH_3NH-C=NOH$. The term "guanidino" denotes an amidino group bonded to an amino group as defined above where said amino group can be bonded to a third group. Examples of such guanidino radicals include, for example, $NH_2-C(NH)NH-$, $NH_2-C(NCH_3)-NH-$, $NH_2-C(NOCH_3)-NH-$, and $CH_3NH-C(NOH)-NH-$.

The term "sulfonium" denotes a positively charged trivalent sulfur atom where said sulfur is substituted with three carbon based groups such as alkyl, alkenyl, aralkyl, or aryl. The term "dialkyl sulfonium" denotes a sulfonium group where said sulfur is substituted with two alkyl groups. Examples of such dialkylsulfonium radicals include, for example, $(CH_3)_2S^+-$. The term "dialkyl sulfonium alkyl" denotes a dialkyl sulfonium group where said group is bonded to one bond of an alkylene group as defined above. Examples of such dialkylsulfoniumalkyl radicals include $(CH_3)_2S^+-CH_2CH_2-$.

The term "phosphonium" denotes a positively charged tetravalent phosphorus atom where said phosphorus is substituted with four carbon based groups such as alkyl, alkenyl, aralkyl, or aryl. The term "trialkyl phosphonium" denotes a phosphonium group where said phosphorus is substituted with three alkyl groups. Examples of such trialkylphosphonium radicals include, for example, $(CH_3)_3P^+$.

Said "alkyl", "alkenyl", "alkanoyl", "alkylene", "alkenylene", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylkyl", "alkylsulfinyl", "alkylsulfinylalkyl", "haloalkylsulfinylalky", "aralkyl", "heteroaralkyl", "perhaloaralkyl", "aralkylsufonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl". "arylsulfonylalkyl", "heteroarylsulfinyl", "heterarlysulfinylalkyl", "heteroarylsulfonyl", "heteroarylsulfonylalkyl", "heteroarylamino", "heteroaylaminoalkyl", "hetararyloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroalkoxyalkyl", "arylthio", "arylthioalkyl", "alkoxyalkyl", "acyl", "amidino, "guanidino", "dialkylsulfonium", "trialkylphosphonium", and "dialkylsulfoniumalkyl" groups defined above may optionally have 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycl alkenyl, cycloalkylsulfinyl, cycloalkylsulfinylalkyl, cycloalkylsulfonyl, cycloalkylsulfonylalkyl, heteroarylamino, N-heteroamino-N-alkylamino, heteroarylaminoalkyl, heteroaryloxy, hetararyloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylithio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, aminoalkyl, hydoxyheteroarakyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 continuous atoms. The spacer may have 1 to 7 atoms of a univalent or multi-valent chain. Univalent chains may be constituted by a radical selected from =(CH)—, =C(R$^{2a}$), —O—, —S—, —S(O)—, —S(O)$_2$—, —NH—, —N(R$^{2a}$)—, —N=, —CH (OH)—, =C(OH)—, —CH(OR$^{2a}$)—, =C(OR$^{2a}$)—, and —C(O)— wherein R$^{2a}$ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or4 or 5 or 6 or 7 atoms or a stright chain of 1 or 2 or 3 or 4 or 5 or 6 atoms with a side chain. The chain may be constituted of one or more radicals selected from: lower alkylene, lower alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$^{2a}$)O—, —O(CH$_2$CHR$^{2a}$)O—, —OCF$_2$O—, —O(CF$_2$)$_2$O—, —S—, —S(O)—, —S(O)$_2$—, —N(H)—, —N(H)O—, —N(R$^{2a}$)O—, —N(R$^{2a}$)—, —C(O)—, —C(O)NH—, —C(O)NR$^{2a}$—, —N=, —OCH$_2$—, —SCH$_2$—, S(O)CH$_2$—, —CH$_2$C (O)—, —CH(OH)—, =C(OH)—, —CH(OR$^{2a}$)—, =C(OR$^{2a}$)—, —S(O)$_2$CH$_2$—, and —NR$^{2a}$CH$_2$— and many other radicals defined above or generally known or ascertained by one of skill-in-the art. Side chains may include substituents such as 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarymidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, alkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroaralkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, 1-isomers, the racenic mixtures thereof and other mixtures thereof, as falling within the scope of the invention. Pharmaceutically acceptable sales of such tautomeric, geometric or steroisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocydic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The present invention also comprises a treatment and prophylaxis in anticoagulant therapy for the treatment and prevention of a variety of thrombotic conditions including coronary artery and cerebrovascular disease in a subject, comprising administering to the subject having such disorder a therapeutically-effective amount of a compound of Formula (I):

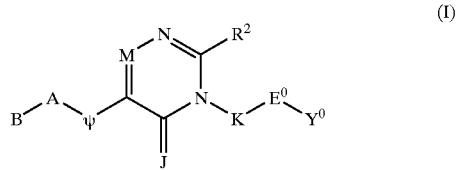

or a pharmaceutically-acceptable salt thereof.

As a further embodiment, compounds of the present invention of Formula (I) or a pharmaceutically-acceptable salt thereof as defined above, comprise a treatment and prophylaxis of coronary artery disease, cerebrovascular disease and other coagulation cascade related disordes in a subject, comprising administering to the subject having such disorder a therapeutically-effective amount of compounds of formula (I) of the present invention or a pharmaceutically-acceptable salt thereof.

Compounds of the present invention of Formula (I) or a pharmaceutically-acceptable salt thereof can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

Compounds of Formula (I) are capable of inhibiting activity of serine proteases related to the coagulation cascade, and thus could be used in the manufacture of a medicament, a method for the prophylactic or therapeutic treatment of diseases mediated by coagulation cascade serine proteases, such as inhibiting the formation of blood platelet aggregates, inhibiting the formation of fibrin, inhibiting thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke deep vein thrombosis, disseminated intravascular coagulation, ocular build up of fibrin, and reocclusion or restenosis of canalized vessels in a mammal. The compounds also can be used to study the mechanism of action of coagulation cascade serine proteases to enable the design of better inhibitors and development of better assay methods. The compounds of Formula (I) would be also useful in prevention of cerebral vascular accident (CVA) or stroke.

Also included in the family of compounds of Formula (I) are the pharmaceutically-acceptable salts thereof. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula (I) may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucotonic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula (I) include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula (I) by reacting, for example, the appropriate acid or base with the compound of Formula (I).

The present invention also comprises a pharmaceutical composition comprising a therapeutically-effective amount of a compound of Formulas (I) in association with at least one pharmaceutically-acceptable carrier, adjuvant or diluent. Pharmaceutical compositions of the present invention can comprise the active compounds of Formula (I) in association with one or more non-toxic, pharmaceutically-aceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The active compounds and composition may, for example, be administered orally, intravascularly, intraperitoneally, subcutaneously, intramuscularly, ocularly, or topically. For treating ocular build up of fibrin, the compounds may be administered introcularly or topically as well as orally or parenterally.

The compounds can be administered in the form of a depot injection or implant preparation which may be formulated in such a mannner as to permit a sustained release of the active ingredient. The active ingredient can be compressed into pelletsor small cylinders and implanted subcutaneously or intranusculary as depot injections or implants. Implants may employ inert materials such as biodegradable polymers or synthetic silicon s, for example. Silastic, silicone rubber or other silicon containing polymers.

The compounds can also be administered in the form of liposome delivery systems, such as small unilamillar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or ployethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdernal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paaffin and/or liquid paraffin or other mineral oils can be used.

For therapeutic purposes, the active compounds of the present invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

In practicing the methods of the present invention for the treatment and prevention of a variety of thrombotic conditions including coronary artery and cerebrovascular disease, the compounds and pharmaceutical compositions of the present invention are administered alone or in combination with one another, or in combination with other therapeutics or in vivo diagnostic agents. The coagulation cascade inhibitors of the present invention can also be co-administered with suitable anti-platelet agreggation agents, including, but not limited to ticlopidine or clopidrogel, fibrinogen receptor antagonists (e.g. to treat or prevent unstable angina or to prevent reocculsion after angioplasty and restenosis), anticoagulants such as aspirin, warfarin or heparins, thrombolytic agents such as plasminogen activators or streptokinase to achieve synergistic effects in the treatment of various pathologies lipid lowering agents including antihypercholesterolemics (e.g. HMG CoA reductase inhibitors such as mevastatin, lovastatin, simvastatin, pravastatin, and fluvastatin, HMG CoA synthatase inhibitos etc.), anti-diabetic drugs, or other cardiovascular agents (loop diuretics, thiazide type diuretics, nitrates, aldosterone antagonistics (i.e., spironolactone and epoxymexlerenone), angiotensin converting enzyme (e.g. ACE) inhibitors, angiotensin II receptor antagonists, beta-blockers, antiarrythmics, anti-hypertension agents, and calcium channel blockers) to treat or prevent atheriosclerosis. For example, patients suffering from coronary artery disease, and patients subjected to angioplasty procedures, would benefit from coadministration of fibrinogen receptor antagonists and coagulation cascade inhibitors of the present invention. Also, coagulation cascade inhibitors could enhance the efficiency of tissue plasminogen activator-mediated thrombolytic reperfusion.

Typical doses of coagulation cascade inhibitors of the present invention with other suitable anti-platelet agents, anticoagulation agents, cardiovascular therapeutic agents, or thrombolytic agents may be the same as those doses of coagulation cascade inhibitors administered without coadministration of additional anti-platelet agents, anticoagulation agents, cardiovascular therapeutic agents, or thrombolytic agents, or may be substantially less than those doses of coagulation cascade inhibitors administered without coadministration of additional anti-platelet agents, anticoagulation agents, cardiovascular therapeutic agents, or thrombolytic agents, depending on a patient's therapeutic needs.

All mentioned references are incorporated by reference as if here written.

Although this invention has been described with respect to specific embodiments, the details of these embodiments are not to be construed as limitations. The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR, mass spectrometry, elemental composition, and similar procedures. These compounds also may be formed in vivo. The following examples contain detailed descriptions of the methods of preparation of compounds of Formula (I). These detailed descriptions fall within the scope and are presented for illustrative purposes only and are not intended as a restriction on the scope of the invention. All parts are by weight and temperatures are Degrees centigrade unless otherwise indicated.

The following general synthetic sequences are useful in making the present invention. Abbreviations used in the schemes and tables include: "AA" represents amino acids, "AcCN" represents acetonitrile, "AcOH" represents acetic acid, "BINAP" represents 2,2'-bis(diphenylphosphino)-1,1'-binaphthyl, "BnOH" represents benzyl alcohol, "BnCHO" represents 2-phenylethanal, "BnSO$_2$Cl" represents benzylsulfonyl chloride, "Boc" represents tert-butyloxycarbonyl, "BOP" represents benzotriazol-1-yl-oxy-tris-(dimethylamino), "bu" represents butyl, "dba" represents dibenzylidene-acetone, "DCC" represents 1,3-dicyclohexylcarbodiimide, "DCM" represents dichloromethane or methylene chloride, "DIBAH" or "DIBAL" represents diisobutylaluminum hydride, "DMF" represents dimethylformamide. "DMSO" represents dimethylsulfoxide, "DPPA" represents diphenylphosphoryl azide", "EDC" represents 1-[3-(dimethylamino)propyl]-3-ethylcarbodiimide hydrochloride, "Ex. No." represents Example Number, "Fmoc", represents 9-fluorenylmethoxycarbonyl, "HOBt" represents hydroxybenzoltriazole", "LDA" represents lithium diisopropylamide, "MW" represents molecular weight, "NMM" represents N-methylimorpholine, "Ph" represents phenyl or aryl, "PHTH" represents a phthaloyl group, "pnZ" represents 4-nitrobenzyloxy-carbonyl, "PTC" represents a phase transfer catalyst, "py" represents pyridine, "RNH$_2$" represents a primary organic amine, "SEM" represents 2-(trimethylsilyl)ethoxy-methyl chloride, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, "THSCN" represents trimethylsilyl cyanide, and "Cbz" or "Z" represents benzyloxycarbonyl.

GENERAL SYNTHETIC PROCEDURES AND SPECIFIC EXAMPLE

The compounds of the present invention can be synthesized, for example, according to the following procedures and Schemes given below.

A general synthetic approach to a wide variety of $R^2$-substituted pyrimidinones is shown in Schemes 1 through Scheme 5 below. Treatment of a solution of ethyl benzimidate hydrochloride in methanol with aminoacetaldehyde dimethyl a provided the substituted benzamidine. Cyclization of the benzamidine with dimethyl methoxymethylene-malonate resulted in the formation of the pyrimidinone heterocyclic core with the required functional groups for further manipulation. Demethylation of the ester with lithium iodide followed by Curtius rearrangement of the resulting acid installed the crucial nitrogen at C-5 as a protected carbarnate. Hydrolysis of the dimethyl acetal and oxidation of the resulting aldehyde with sodium chlorite gave the glycine unit at N-3. Protection of the acid as a t-butyl ester followed by deprotection of carbarnate by hydrogenation gave the free amine at C-5. Treatment of this amine with a sulfonyl chloride or with an aldehyde under reductive amination conditions gave the sulfonamide or secondary amine, respectively. The protected acids were then unmasked with HCl. These acids are then coupled under standard peptide coupling conditions with various amines. These amines are typically multifunctional, and are used in some protected form. Removal of these protecting groups provides the compounds for evaluation. These synthetic schemes and procedures are exemplified below.

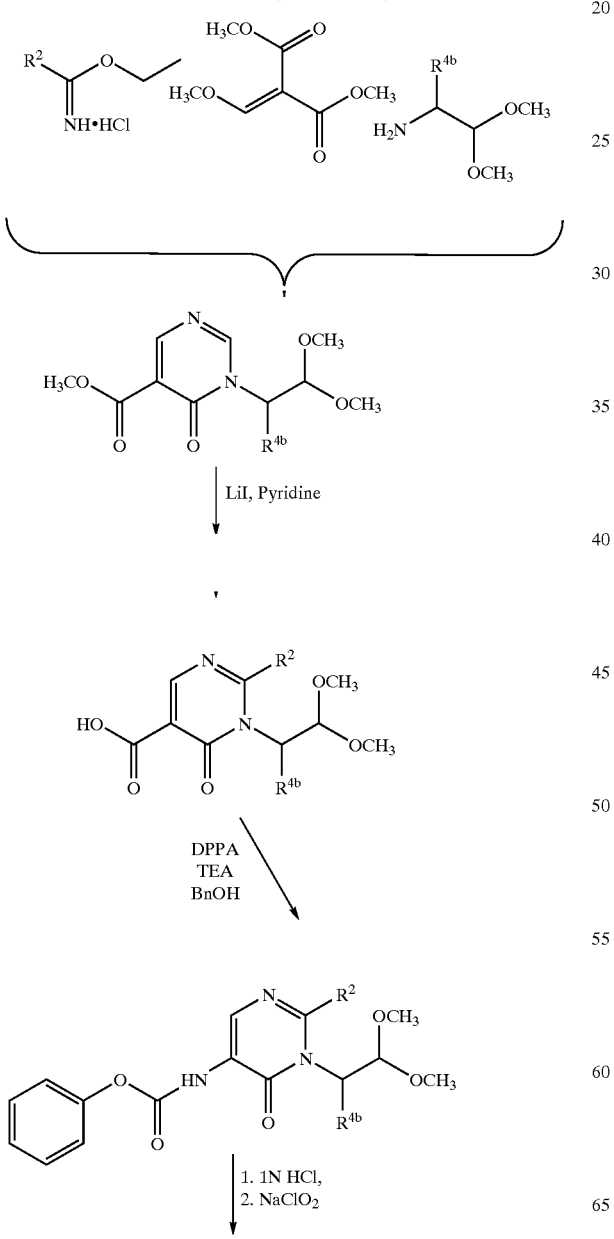

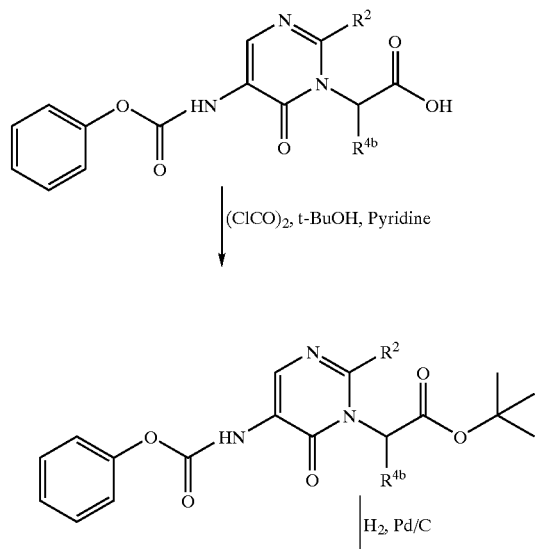

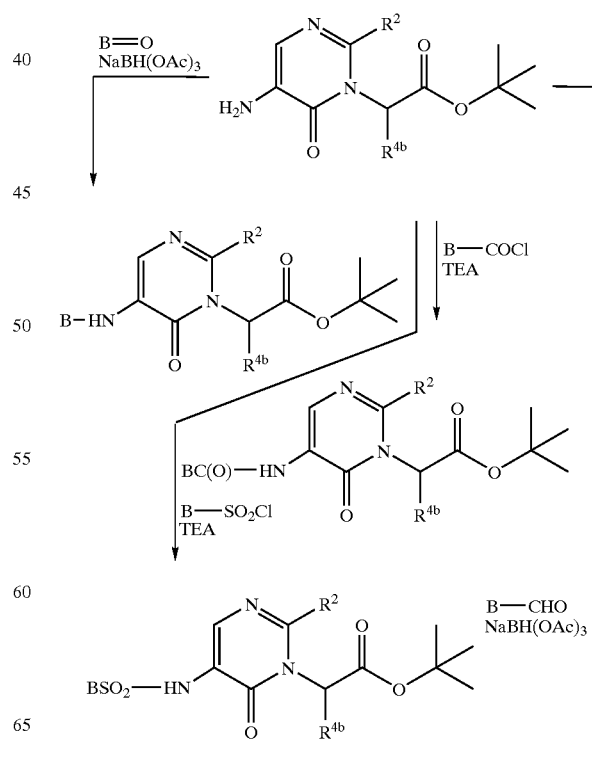

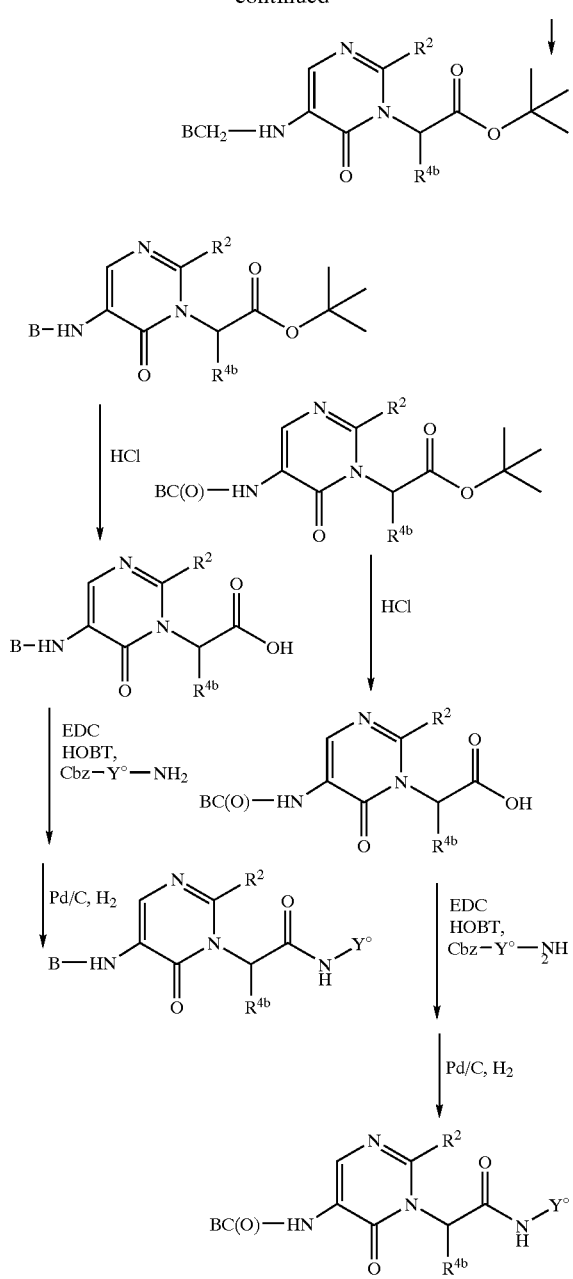

Scheme 5: General Pyrimidinone Synthesis-I (Concluded)

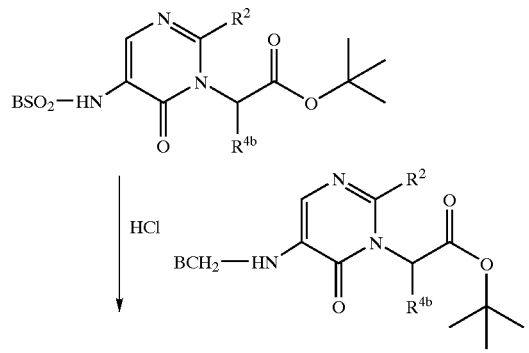

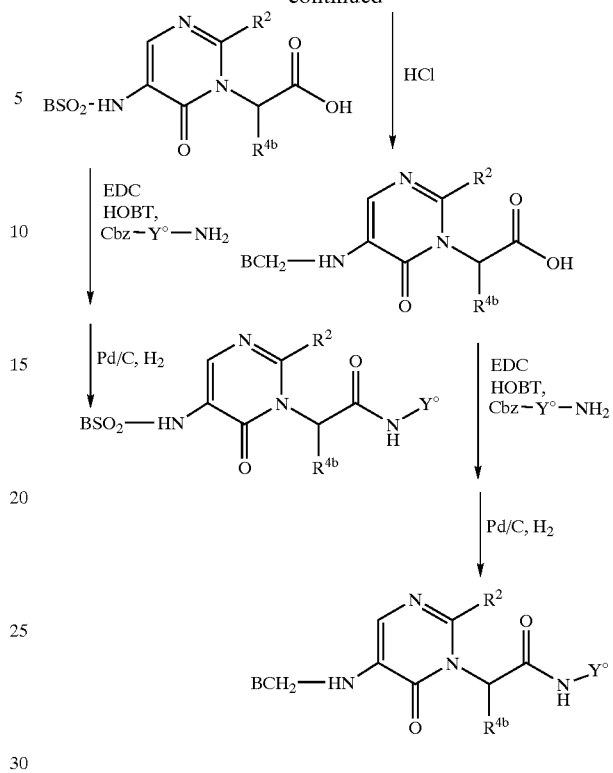

Synthetic Scheme 1 through Scheme 5 are exemplified in the following examples.

Example 1

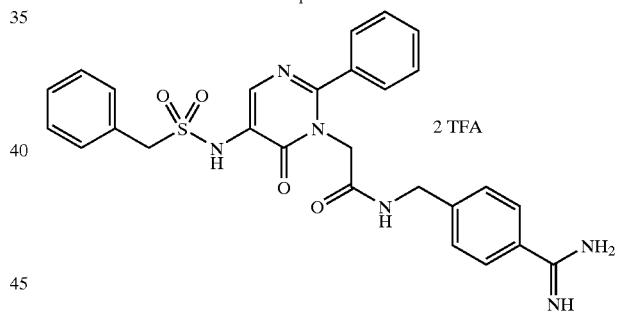

(EX-1A) A solution of ethyl benzimidate hydrochloride (92.25 g, 496.9 mmol) in 300.0 mL dry methanol (1.68 M) was cooled to ca 0° C. and added a solution of aminoacetaldehyde dimethyl acetal (73.10 mL, 670.9 mmol) in dry methanol (75.0 mL, 9.0 M) drop wise at such a rate the temperature was kept below 5° C. The resulting solution was allowed to stir for 3 days with the temperature being maintained below 5° C. The reaction mixture was then concentrated under reduced pressure to give a yellow oil. The residue was dissolved in 1 N NaOH (750 mL) and extracted with dichloromethane (4×250 mL). The organic solutions were combined, dried (MgSO$_4$), and concentrated to give 108.13 g crude N-(2,2-dimethoxyethyl)benzamidine as a yellow oil. The crude N-(2,2-dimethoxyethyl) benzamidine (108.13 g, 519.2 mmol) in dry methanol (125.0 mL, 4.2 M) was added dimethyl methoxymethylenemalonate (94.13 g, 540.5 mmol) in one portion at room temperature. The resulting mixture was heated to approximately 100° C., where the solvent was slowly distilled off over a two hour period. The resulting dark brown solution was allowed to cool to room temperature and was diluted ethyl acetate (1 L). The organic solution was washed with saturated NH$_4$Cl (2×500 mL) and brine (1×500 ml). The organic solution was dried (MgSO$_4$), filtered and concentrated. Purification of the crude product by MPLC (25% ethyl acetate/hexane) gave pure methyl 1-(2,2-dimethoxyethyl-2-phenylpyrimidin-6(1H)-one-5-carboxylate (EX-1A) in 73% yield as a tan oil: $^1$H NMR (300 MHz, CDCl$_3$) δ 8.73 (s, 1H), 7.59–7.49 (m, 5H), 4.86 (t, J=5.5 Hz, 1H), 4.16 (d, J=5.4 Hz, 2H), 3.95 (s, 3H), 3.32 (s, 6H); $^{13}$C NMR (75 MHz, CDCl$_3$) δ 165.9, 164.6, 159.3, 158.2, 134.6, 130.9, 128.93, 128.78, 114.9, 101.9, 56.0, 55.1, 52.7, 49.1; HRMS (ES) calcd for C$_{16}$H$_{19}$N$_2$O$_5$ 319.1294, found 319.1288.

(EX. 1B) A solution of methyl 1-2,2-dimethoxyethyl-2-phenylpyrimidin-6(1H)-one-5-carboxylate (93.00 g, 292.2 mmol) in 420.0 mL dry pyridine (0.70 M) was added lithium iodide (98.00 mL, 732.2 mmol) in one portion with stirring at room temperature, upon which an exotherm occurs. The resulting light brown suspension was heated to reflux for 2 hours. The dark brown reaction was allowed to cool to room temperature and the volatiles were removed under reduced pressue. The resulting oil was diluted with 1 N HCl (500 mL). The aqueous solution was extracted with dichloromethane/methanol (4:1, 4×250 mL). The combined organic solutions were washed with 6 N HCl (2×250 mL), dried (MgSO$_4$), filtered and concentrated. The crude product was purified by crystallization (ethyl acetate/hexane) to give pure 1-(2,2-dimethoxyethyl-2-phenylpyrimidin-6(1H)-one-5-carboxylate (EX-1B) in 63% yield as a white solid: $^1$H NMR (300 MHz, CDCl$_3$) δ 12.99 (s, 1H), 8.97 (s, 1H), 7.63–751 (m, 5H), 4.78 (dd, J=4.3, 5.5 Hz, 1H), 4.28 (d, J=5.4 Hz, 2H), 3.30 (s, 6H); $^{13}$C NMR (75 MHz, CDCl$_3$) δ 165.8, 165.1, 164.1, 159.1, 133.6, 131.5, 129.1, 129.0, 112.6, 101.0, 55.8, 49.2; HRMS (ES) calcd for C$_{15}$H$_{17}$N$_2$O$_5$ 305.1137, found 305.1113.

(EX 1C) A suspension of 1-(2,2-dimethoxyethyl-2-phenylpyrimidin-6(1H)-one-5-carboxylate-(65.93 g, 216.67 mmol) in 800 mL 1,4-dioxane (0.27 M) was added triethylanine (50.0 mL, 358.7 mmol) followed by diphenylphosphoryl azide (51.40 mL, 238.5 mmol) in one portion at room temperature. The resulting solution was slowly heated to reflux for 2 hours. The reaction mixture was then added benzyl alcohol (45.00 mL, 434.8 mmol) and refluxing was maintained for approximately 14 hours. The black solution was allowed to cool to room temperature, and the volatiles were removed under vacuum. The resulting residue was diluted with ethyl acetate (1.5 L). The organic solution was washed with saturated NH$_4$Cl (2×500 mL), 1 N NaOH (1×500 mL), and brine (1×500 ml). The organic solution was dried (MgSO4), filtered and concentrated to give the crude product. Purification by MPLC(15%–30% ethyl acetate/hexane) afforded pure [5-[(benzyloxyarbonyl)amino]-2-phenyl-6-oxo-1,6-dihydro-1-pyrimidinyl]acetaldehyde dimethyl acetal (EX-1C) as light brown solid in 46% yield. $^1$H NMR (400 MH, CDCl$_3$) δ 8.72 (br s, 1H), 7.53–7.32 (m, 11H), 5.20 (s, 2H), 4.68 (t, J=5.6 Hz, 1H), 4.12 (d, J=5.6 Hz, 2H), 3.22 (s, 6H); $^{13}$C NMR (100 MHz. CDCl$_3$) δ 158.3, 153.7, 153.2, 135.9, 134.9, 134.7, 130.1, 129.1, 128.9, 128.8, 128.71, 128.66, 128.4, 125.1, 101.3, 67.7, 55.4, 48.6; HRMS (EI) calcd for C$_{22}$H$_{24}$N$_3$O$_5$ 410.1716, found 410.1741.

(EX-1D) A solution of [5-[(benzyloxycarbonyl)amino]-2-phenyl-6-oxo-1,6-dihydro-1-pyridinyl]acetaldehyde dimethyl acetal (17.24 g, 42.11 mmol) in 103.0 mL tetrahydrofuran was added 35.0 mL 1 N HCl. The resulting biphasic mixture was allowed to heated to reflux for 12 hours. The reaction mixture was allowed to cool to room temperature and the volatiles were removed under vacuum. The resulting residue was diluted with water (200 mL) and the pH was adjusted to 7 by addition of solid NaHCO3. The resulting emulsion was extracted with dichloromethane (4×150 mL). The combined organic solutions were washed with water (1×200 mL), dried (MgSO$_4$), filtered, and concentrated to give 15.74 g crude [5[(benzyloxycarbonyl)amino]-2-phenyl-6-oxo-1,6-dihydro-1-pyrimidinyl]acetaldehyde.

A solution of crude [5-[(benzyloxycarbonyl)amino]-2-phenyl-6-oxo-1,6-dihydro-1-pyrimidinyl]acetaldehyde (15.30 g, 42.11 mmol) in 198.0 mL of tetrahydrofuran, t-butyl alcohol, and 2-methyl-2-butene (1:1:1.3, 0.21 M) was cooled to 0° C. The solution was then slowly added a solution of sodium chlorite (29.94 g, 331.1 mmol) and sodium dihydrogenphosphate monohydrate (35.42 g, 256.7 mmol) in 102.0 mL of water (3.2 M based on sodium chlorite). The resulting gold colored, biphasic solution was stirred for 10 minutes and the cold bath was removed. The reaction was stirred for 1 hour at room temperature. The volatiles were removed under reduced pressure. The resulting solution was diluted with water (200 mL) and the pH was adjusted to 3 by addition of sat NaHCO3 and 1 N HCl. The aqueous solution was extracted by tetrahydrofuran, dichloromethane (1:2, 4×180 mL). The combined organic solutions were dried (MgSO4), filtered, and concentrated to give the crude product. Purification by trituration with ethyl ether gave an 88% yield of [5-[(benzyloxycarbonyl)amino]-2-phenyl-6-oxo-1,6-dihydro-1-pyrimidinyl]acetic acid as a white solid: $^1$H NMR (300 MHz, d-DMSO) δ 13.34 (br s, 1H), 9.03 (s, 1H), 7.57–7.34 (m, 10H), 5.23 (s, 2H), 4.56 (s, 2H); $^{13}$C NMR (75 MHz, d-DMSO) δ 169.4, 158.0, 154.6, 154.3, 137.1, 134.8, 130.9, 129.4, 129.1, 128.78, 128.72, 128.50, 125.5, 67.0, 48.8; HRMS (EI) calcd for C$_{20}$H$_{18}$N$_3$O$_5$ 380.1246, found 380.1246.

(EX-1E) A suspensi n of [5-[(benzyloxycarbonyl)amino]-2-phenyl-6-oxo-1,6-dihydro-1-pyrimidinyl]acetic acid (5.2503 g, 13.84 mmol) in 70.0 mL chloroform (0.2 M) was cooled in an ice bath to approximately 0° C. The cold suspension was then added oxalyl chloride (6.00 mL, 68.78 mmol) drop wise via syringe. After vigorous gas evolution, a golden homogeneous solution resulted. After stirring for 5 minutes, the cold bath was removed and the solution was stirred for an additional 2 hours at room temperature. The solvent was removed under reduced pressure and placed on the high vacuum system to remove residual solvents for 10 minutes. The resulting yellow solid was diluted with 70.0 mL chloroform (0.2 M) and added pyridine (1.70 mL, 21.02 mmol) and 2-methyl-2-propanol (3.50 ml, 36.60 mmol). The resulting tan colored solution was stirred for 1 hour at room temperature, and then heated to reflux for 12 hours. The reaction mixture was cooled to room temperature and diluted with chloroform (300 mL). The organic solution was washed with water (1×100 mL), saturated NaHCO$_3$(1×100 mL), and brine (1×100 mL). The organic solution was dried (MgSO$_4$), filtered and concentrated. The crude reaction was purified by MPLC (25% ethyl acetate/hexanes) to give the product in 49% yield: $^1$H NMR (300 MHz, CDCl$_3$) δ 8.81 (br s, 1H), 7.57–7.38 (m, 11H), 5.27 (s, 2H), 4.57 (s, 2H), 1.47 (s, 9H); $^{13}$C NMR (75 MHz, CDCl$_3$) δ 166.4, 158.0, 153.2, 135.9, 135.0, 134.4, 130.6, 129.1, 128.9, 128.7, 128.5, 128.4, 125.4, 83.4, 67.7, 49.1, 28.2; HRMS (EI) calcd for C$_{24}$H$_{26}$N$_3$O$_5$ 436.1872, found 436.1876.

(EX-1F) A solution of [5-amino-2-phenyl-6-oxo-1,6-dihydro-1-pyrimidinyl]acetic acid t-butyl ester (1.8647 g, 4.282 mmol) in 21.0 mL methanol (0.2 M) was added 2113 mg 10% Pd/C in one portion. The resulting mixture was stirred under an atmosphere of hydrogen gas (balloon) at room temperature for approximately 16 hour. The crude reaction mixture was filtered through a pad of Celite 545 and the solvent was removed under reduced pressure. The crude product was triturated from ethyl ether to give pure product [5-amino-2-phenyl-6-oxo-1,6-dihydro-1-pyrimidinyl]acetic acid t-butyl ester (EX-1F) in 99% yield: $^1$H NMR (400 MHz, CDCl$_3$) δ 7.41–7.39 (m, 6H), 4.48 (s, 2H), 4.06 (br s, 2H), 1.39 (s, 9H); $^{13}$C NMR (100 MHz, CDCl$_3$) δ 166.8, 158.6, 149.3, 134.9, 132.9, 130.0, 128.9, 128.5, 127.7, 82.9. 48.7. 28.1; HRMS (EI) calcd for C$_{16}$H$_{20}$N$_3$O$_3$ 302.1505, found 302.1491.

(EX-1G) A solution of [5-amino-2-phenyl-6-oxo-1,6-dihydro-1-pyrimidinyl]acetic acid t-butylester (1.0300 g, 3.418 mmol) in 5.5 mL tetrahydrofuran and 2.0 mL dimethylformamide (0.45 M) was added N-methylmorpholine (1.20 mL, 10.91 mmol) in one portion. The solution was cooled to 0° C. in an ice bath. After stirring for 10 minutes, a solution of 718.2 mg a-toluenesulfonyl chloride (3.767 mmol) in 5.5 mL tetrahydrofuran (0.68 M) was added drop wise over a 5 minute period. The reaction mixture was stirred for 2 hours at 0° C. The reaction mixture was diluted with ethyl acetate (150 mL). The organic solution was washed with 1 N HCl (2×25 mL), saturated NaHCO$_3$ (2×25 mL), and brine (1×50 mL). The organic solution was dried (MgSO$_4$), filtered and concentrated under reduced pressure. The resulting yellow solid was triturated with ethyl ether, filtered, and dried under vacuum to afford pure product (EX-1G) as a white solid in 74% yield: $^1$H NMR (400 MHz, d-DMSO) δ 9.34 (s, 1H), 7.76 (s, 1H), 7.55–7.28 (m, 10H), 4.59 (s, 2H), 4.49 (s, 2H), 1.32 (s, 9H); $^{13}$C NMR (100 MHz, d-DMSO) δ167.0, 158.8, 156.5, 142.1, 134.5, 131.7, 131.0. 130.1, 129.4, 129.0, 128.94, 128.58, 124.8, 83.0, 59.6, 49.2, 28.1: HRMS (EI) calcd for C$_{23}$H$_{26}$N$_3$O$_5$S 456.1593, found 456.1597.

(EX-1H) A solution of (EX-1G) (1.0643 g, 2.336 mmol) in 9.0 mL 4M HCl in dioxane (0.1 M) was stirred for 12 hours at room temperature. The crude reaction was concentrated under reduced pressure. The resulting residue was triturated with ethyl ether to afford pure product (EX-1H) in 87% yield as a white solid. $^1$H NMR (400 MHz, d-DMSO) δ 9.32 (s, 1H), 7.74 (s, 1H), 7.51–730 (m, 10H), 4.58 (s, 2H), 4.48 (s, 2H); $^{13}$C NMR (100 MHz, d-DMSO) δ 169.2, 158.7, 156.6, 141.8, 1345, 131.7, 131.0, 130.1, 129.4. 129.0, 128.90, 128.56, 124.8, 59.6, 48.9; HRMS (EI) calcd for C$_{19}$H$_{18}$N$_3$O$_5$S 400.0967, found 400.0959.

(EX-1I) A solution of acid (EX-1H) (406.8 mg, 1.018 mmol) in 10.0 mL dimethylformamide (0.10 M) was added N,N-diisopropylethylamine (0.900 mL, 5.167 mmol), N-hydroxybenzotriazole (167.7 mg, 1.241 mmol), and 1-[3-(dimethylamino)propyl]-3-ethylcarbodiimide hydrochloride (236.1 mg, 1.232 mmol). The resulting mixture was allowed to stir for 30 minutes at room temperature after which the mixture had become homogeneous. The reaction mixture was then added 4-(Cbz-amidino)benzylamine (324.6 mg, 1.126 mmol) in one portion at room temperature. The resulting mixture was then allowed to stir for 18 hours. The reaction mixture was diluted with ethyl acetate (50 mL). The organic solution was washed with 5% citric acid (1×25 mL), saturated NaHCO$_3$ (1×25 mL), and brine (1×25 mL). The organic solution was dried (MgSO$_4$), filtered and concentrated. The crude reaction mixture was purified trituration with ethyl ether to afford pure product (EX-1I) in as a white solid $^1$H NMR (300 MHz, d-DMSO) δ 9.36–9.18 (br m, 3H), 8.82–8.78 (m, 1H), 7.98 (d, J=8.3 Hz, 2H), 7.84, (s, 1H), 7.56–7.32 (m, 16H), 5.15 (s, 2H), 4.65 (s, 2H), 4.58 (s, 2H), 4.40 (d, J=5.4 Hz, 2H); HRMS (EI) calcd for C$_{35}$H$_{33}$N$_6$O$_6$S$_2$ 665.2182, found 665.2177.

A solution of Cbz-amidine (EX-1I) (237.7 mg, 357.6 mmol) in 3.5 mL methanol and 4 M HCl in dioxane (4:1, 0.1 M) was added 42.1 mg 10% Pd/C in one portion. The resulting mixture was stirred under an atmosphere of hydrogen gas (balloon) at room temperature for approximately 16 hours. The crude reaction mixture was filtered through a pad of Celite 545 and the solvent was removed under reduced pressure. Purification of the crude product by HPLC (gradient, 5%–95% acetonitrile/water with 0.1% trifluoroacetic acid) afforded pure product as a white solid. $^1$H NMR (300 MHz, d-DMSO) δ 9.31–9.28 (m, 4H), 8.88 (br s, 1H), 7.81–7.77 (m, 3H), 7.60–7.54 (m, 5H), 7.43–737 (m, 7H), 4.65 (s, 2H), 4.58 (s, 2H), 4.42–4.41 (m, 2H); HRMS (EI) calcd for C$_{27}$H$_{27}$O$_4$S 531.1815, found 531.1794.

Example 2

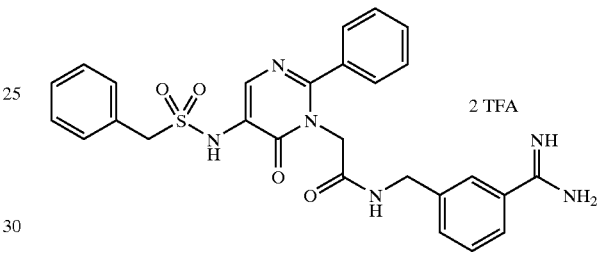

By following the method of Example 1, the title compound was prepared: $^1$H NMR (300 MHz, d-DMSO) δ 9.40–9.33 (m, 4H), 8.86 (s, 1H), 7.82 (s, 2H), 7.72–737 (m, 15H). 4.65–459 (m, 4H), 4.41–4.40 (m, 2H); HRMS (EI) calcd for C$_{27}$H$_{27}$N$_6$O$_4$S 531.1815, found 531.1794.

Example 3

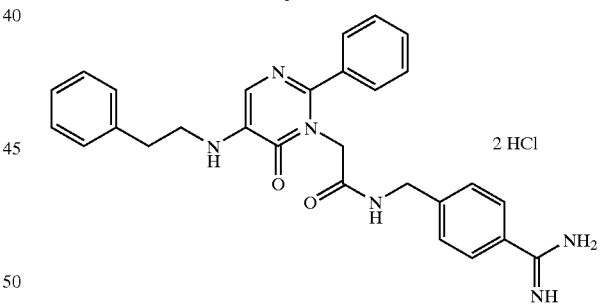

(EX3A) A solution of [5-amino-2-phenyl-6-oxo-1,6-dihydro-1-pyrimidinyl]acetic acid t-butyl ester (EX-1F) (613.7 mg. 2.037mmol) in 7.0 mL, tetiydrofuran and dichloromethane (1:1, 0.3 M) was added 25.0 mL acetic acid and phenylacetaldehyde (0.475 ml, 4.060 mmol). The solution was cooled to 0° C. in an ice bath and added sodium triacetoxyborohydride (1.9131 g, 9.027 mmol) in one portion. After stirring for 5 minutes, the ice bath was removed and the reaction mixture was allowed to stir at room temperature for 2 hours. The reaction was quenched by the addition of 1 N NaOH (5 mL), and the mixture was stirred for 5 minutes. The reaction mixture was diluted 0.5 N NaOH (100 mL). The aqueous solution was extracted with ethyl acetate (3×25 mL). The combined organic solutions were washed with 0.5 N NaOH (1×25 mL) and brine (1×25 mL).

The solution was dried (MgSO₄), filtered and concentrated under reduced pressure. Purification by MPLC (25% ethyl acetate/hexanes) afforded EX-3A as a yellow oil in 74% yield. ¹H NMR (400 MHz, CDCl₃) δ 7.43–7.40 (m, 4H), 7.31–7.26 (m, 2H), 7.23–7.16 (m, 5H), 4.70 (br s, 1H), 4.49 (s, 2H), 3.38–334 (m, 2H), 2.96–2.92 (m, 2H), 1.40 (s, 9H); HRMS (EI) calcd for $C_{24}H_{28}N_3O_3$ 406.2131, found 406.2125.

A solution of EX-3A (521.3 mg, 1.286 mmol) in 13.0 mL 4M HCl in dioxane (0.1 M) was stirred for 12 hours at room temperature. The crude reaction was concentrated under reduced pressure. The resulting residue was triturated with ethyl ether to afford pure product EX-3B in quantitative yield as a yellow solid: ¹H NMR (300 MHz, d-DMSO) δ 7.66–7.57 (m, 5H), 733–7.23 (m, 6H), 4.57 (s, 2H), 3.44–3.35 (m, 2H), 2.97–2.92 (m, 2H); ¹³C NMR (75 MHz, d-DMSO) δ 168.8, 157.0, 148.0, 139.9, 135.0, 132.2, 129.69, 129.48, 129.07, 126.9, 48.8, 44.5, 34.5; HRMS (EI) calcd for $C_{20}H_{20}N_3O_3$ 350.1505, found 350.1520.

A solution of EX-3B (497.8 mg, 1.290 mmol) in 13.0 mL, dimethylformamide (0.10 M) was added N,N-diisopropylethylamine (1.800 mL, 1033 mmol), N-hydroxybenzotriazole (212.8 mg, 1.575 mmol), and 1-[3-(dimethylamino)propyl]-3-ethylcarbodiimide hydrochloride (302.5 mg, 1.578 mmol). The resulting, mixture was allowed to stir for 30 minutes at room temperature after which the mixture had become homogeneous. The reaction mixture was then added 4-(Cbz-amidino)benzylamine (410.9 mg, 1.425 mmol) in one portion at room temperature. The resulting mixture was then allowed to stir for 18 hours. The reaction mixture was diluted with ethyl acetate (50 mL). The organic solution was washed with 5% citric acid (1×25 mL), saturated NaHCO₃ (1×25 mL), and brine (1×25 mL). The organic solution was dried (MgSO₄), filtered and concentrated. The crude reaction mixture was purified trituration with ethyl ether to afford pure product EX-3C in as a white solid: ¹H NMR (400 MHz, d-DMSO) δ 9.08 (br s, 2H), 8.62 (t, J=5.8 Hz, 1H), 7.90 (d, J=83 Hz, 2H), 7.44–7.15 (m, 17H), 535 (t, J=5.9 Hz, 1H), 5.07 (s, 2H), 4.44 (s, 2H), 4.29 (d, J=5.4 Hz, 2H), 331–3.26 (m, 2H), 2.88–2.85 (m, 2H); HRMS (EI) calcd for $C_{36}H_{35}N_6O_4$ 615.2720, found 615.2688.

A solution of EX-3C (222.6 mg, 362.1 mmol) in 4.0 mL methanol and 4 M HCl in dioxane (3:1, 0.1 M) was added 53.0 mg 10% Pd/C in one portion. The resulting mixture was stirred under an atmosphere of hydrogen gas (balloon) at room temperature for approximately 16 hours. The crude reaction mixture was filtered through a pad of Celite 545 and the solvent was removed under reduced pressure. Purification of the crude product by trituration from ethyl ether afforded pure product as a yellow solid. ¹H NMR (300 MHz, d-DMSO) δ 9.62–930 (br m, 5H). 7.88 (br m, 2H), 7.58–6.86 (br m, 15H), 4.59 (br s, 2H), 436 (br s, 2H), 3.38 (br s, 2H), 2.91 br s, 2H); HRMS (EI) calcd for $C_{28}H_{29}N_6O_2$ 481.2352, found 481.2348

Pyrimidinones having, for example, a directly bonded 2-aryl, 2-heteroaryl, or 2-heteroatom linking/bonding an organic group through the heteroatom to the pyrimidinone ring can be prepared using Scheme 6 and Scheme 7 below. The heteroatom is typically a sulfur, nitrogen, oxygen, or another suitable heteroatom. Use of the general procedure in Scheme 6 to prepare specific heteroatom substituted pyrimidinones is disclosed in Examples 4 and 5.

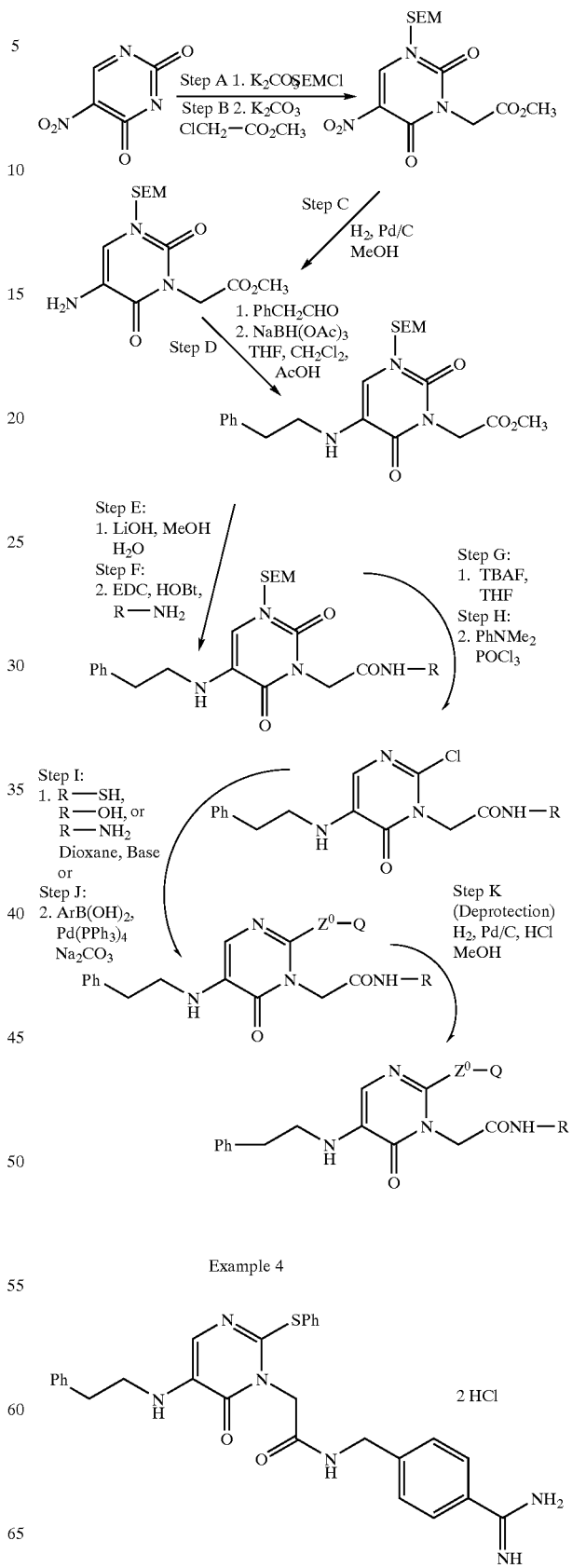

Scheme 6: Preparation f 2-Substituted Pyrimidinones

Example 4

(EX-4A) A solution of 5-nitro-2,4(1H,3H) pyrimidinedione in dimethylsulfoxide (0.2 M) is added 1.1 equivalents potassium carbonate in one portion with stirring. After approximately 10 minutes, a solution of 1 equivalent 2-(trimethylsilyl)ethoxy-methyl chloride in dimethylsulfoxide is added drop wise. The reaction mixture is then heated to 40° C. and allowed to stir for 18 hours. Typical aqueous work up followed by chromatographic purification provides pure product EX-4A.

EX-4B) A solution of 5-nitro-1-SEM-2,4(1H,3H) pyrimidinedione (EX-4A) in dimethylsulfoxide (0.2 M) is added 1.1 equivalents potassium carbonate in one portion with stirring. After approximately 10 minutes a solution of 1 equivalent methyl bromoacetate in dimethylsulfoxide is added drop wise. The reaction mixture is then heated to 40° C. and allowed to stir for 18 hours. Typical aqueous work up followed by chromatographic purification provides pure product EX-4B.

EX-4C) A solution of 5-nitro-1-SEM-3-methoxycarbonylmethyl (EX-4B) 2,4(1,H3H) pyrimidinedione in methanol is degassed with hydrogen gas. To the solution is then added 5% Pd/C which is stirred under an atmosphere of hydrogen at room temperature for 24 hours. The crude reaction is filtered though a pad of Celite 545 and concentrated under reduced pressure. Purification by column chromatography gives pure 5-amino-1-SEM-3-methoxycarbonylmethyl-2,4(1H,3H)pyrimidinedione EX-4C.

EX-4D) To a solution of 5-amino-1-SEM-3-methoxycarbonylmethyl-2,4(1H,3H)pyrimidinedione (EX-4C) in tetrahydrofuran and dichloromethane (1:1, 0.3 M) is added a catalytic amount of acetic acid and 1 equivalent phenylacetaldehyde. The solution is cooled to 0° C. in an ice bath and 1 equivalent sodium triacetoxyborohydride is added in one portion. After stirring for 5 minutes, the ice bath is removed, and the reaction mixture is allowed to stir at room temperature for 2 hours. The reaction is quenched by the addition of 1 N NaOH, and the mixture is stirred for 5 minutes. Typical aqueous work up, followed by chromatographic purification provides pure product EX-4D.

EX-4E) To a solution of 1-SEM-3-methoxycarbonylmethyl-5-(2-phenylethyl)amino-2,4(1H,3H)pyrimidinedione (EX-4D) in tetrahydofuran and methanol (1:1, 0.2 M) is added 1 equivalent of lithium hydroxide in water. After the reaction is complete, the volatiles are removed under reduced pressure. The remaining aqueous solution is cooled in an ice bath and acidified to a pH of 1 with 1.0 N HCl. Extraction with organic solvent and removal of the solvent under reduced pressure gives pure product EX-4E.

EX-4F) To a solution of 1-SEM-3-methylenecarboxy-5-(2-phenylethyl)amino-2,4(1H,3H)pyrimidinedione dimethylformamide (0.1 M) are added 5 equivalents of N,N-diisopropylethylamine, 1 equivalent of N-hydroxybenzotriazole, and 1 equivalent of 1-[3-dimethylamino)propyl]-3-ethylcarbodiimide hydrochloride. The resulting mixture is stirred for 30 minutes. The reaction mixture is then treated with 1 equivalent of the appropriate amine and allowed to stir over night. Typical aqueous work up followed by chromatographic purification gives pure product EX-4F.

EX-4G) To a solution of 1-SEM-3-methylenecarbamide-5-(2-phenylethyl)amino-2,4(1H,3H)pyrimidinedione in tetrahydrofuran (0.3M) is added 2 equivalents of tetrabutylammonium fluoride in tetrahydrofuran. The resulting solution is refluxed for several hours. Typical aqueous work up is followed by chromatographic purification to give pure product EX-4G.

EX-4H) To a solution of 3-methylenecarboxamide-5-(2-phenylethyl)amino-2,4(1H,3H)pyrimidinedione (EX-4G) in N,N-dimethylaniline (0.3M) is added 1 equivalent of phosphorus oxychloride. The resulting solution is refluxed for several hours. Typical aqueous work up is followed by chromatographic purification to give pure product EX-4H.

EX-4I) To a solution of 2-chloro-3-methylenecarbamide-5-(2-phenylethyl)amino-2,4(1H,3H)pyrimidinedione (EX-4H) in dioxane (0.3M) is added 2 equivalents of phenylthiol. The resulting solution is refluxed for several hours. Typical aqueous work up is followed by chromatographic purification to give pure product EX-4I.

A solution of 2-thiophenyl-3-methylenecarboxamide-5-(2-phenylethyl)amino-2,4(1H,3H)pyrimidinedione (EX-4I) in methanol and 4M HCl dioxane (3:1, 0.1 M) is degassed with hydrogen gas. To the solution is then added 5% Pd/C which is stirred under an atmosphere of hydrogen at room temperature for 24 hours. The crude reaction is filtered through a pad of Celite 545 and concentrated under reduced pressure. Purification by column chromatography gives pure product.

Example 5

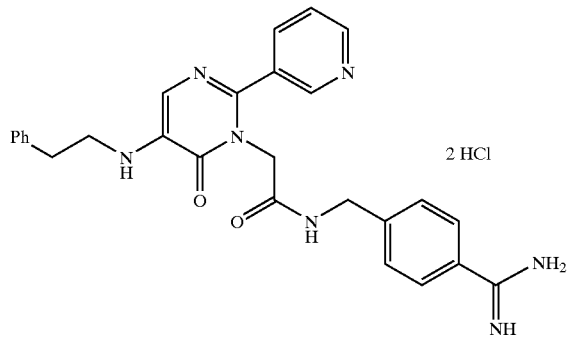

EX-5A) To a degassed solution of 2-chloro-3-methylencarboxamide-5-(2-phenylethyl)amino-2,4(1H,3H) pyrimidinedione and 1 equivalent of 3-pyridineboronic acid in 1-propanol (0.5M) is added 1.2 equivalents of 2.0 M sodium carbonate followed by 1 mol % of tetrakis (triphenylphosphine)palladium. The resulting mixture is heated to reflux for several hours. After cooling to room temperature, typical aqueous work up is followed by chromatographic purification to give pure product EX-5A.

A solution of 2-(3-pyridinyl)-3 -methylenecarboxamide-5-(2-phenylethyl)amino-2,4(1H,3H)pyrimidinedione (EX-5A) in methanol and 4M HCl dioxane (3:1, 0.1 M) is degassed with hydrogen gas. To the solution is then added 5% Pd/C, and the solution is stirred under an atmosphere of hydrogen at room temperature for 24 hours. The crude reaction is filtered through a pad of Celite 545 and concentrated under reduced pressure. Purification by column chromatography gives pure product.

Pyrimidinones having, for example, a directly bonded 2-aryl, 2-heteroaryl, or 2-heteroatom linking/bonding an organic group through the heteroatom to the pyrimidinone ring can also be prepared using Scheme 7 below. In this reaction scheme, the aryl is introduced by forming a carbon-carbon bond. Heteroatom suitable for forming heterolinked aryl pyrimidinones include sulfur, nitrogen, oxygen, or another suitable heteroatom. Use of the general procedure in Scheme7 to prepare specific heteroatom substituted pyrimidinones is disclosed in Examples 6 and 7.

Scheme 7: Alternate Pyrimidinone Synthesis

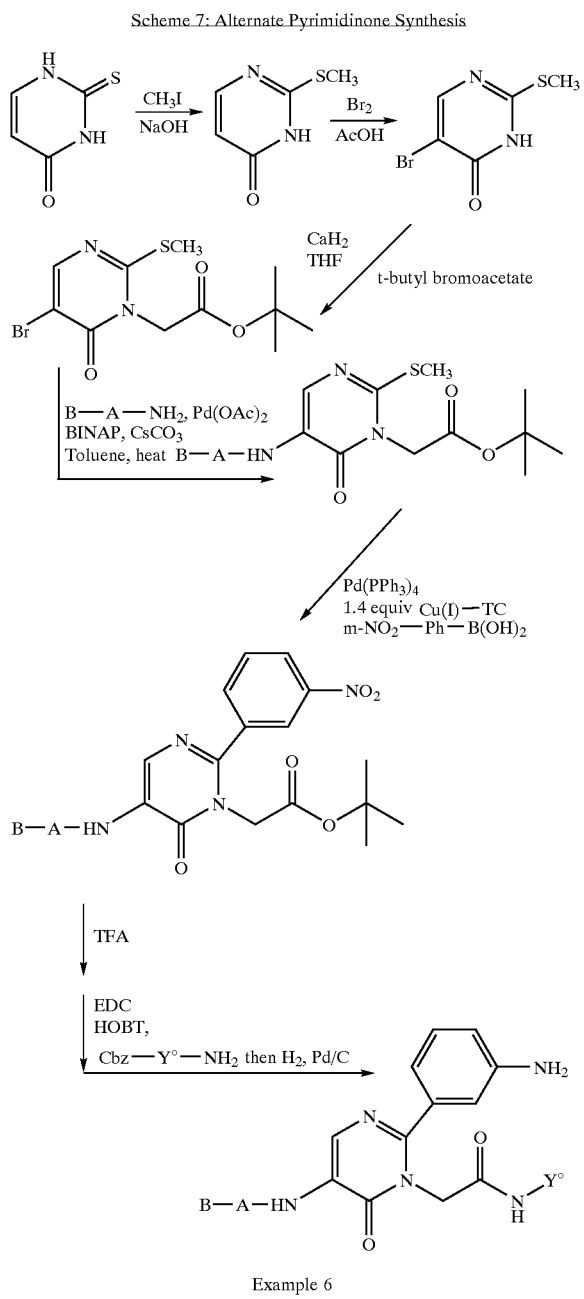

Example 6

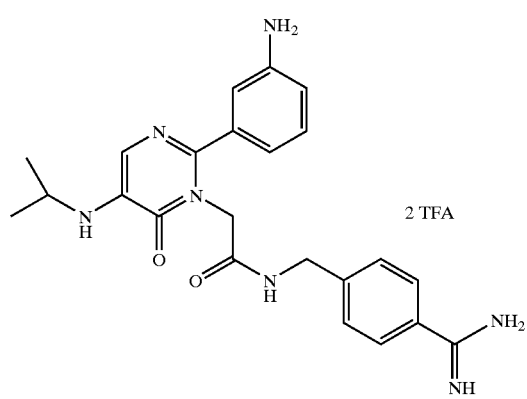

(EX-6A) 2-Thiouracil (66.7 g, 520.5 mmol) was dissolved in a sodium hydroxide solution (41.6 g of solid NaOH in 365 mL of water). The mixture was then treated with methyl iodide (37 mL, 583 mmol), and the resulting reaction mixture was allowed to stir for 16 h at room temperature. The solution was then acidified with glacial acetic acid (30 mL). The white precipitate was collected by suction filtration, and the solid was washed several times with cold water and dried to afford 74 g of EX-6A as a white crystalline solid in quantitative yield.

(EX-6B) A solution of EX-6A (74.0 g, 520.5 mmol) in glacial acetic acid (2275 mL) was cooled to 0° C. with an ice bath and treated with $Br_2$. The reaction mixture was allowed to warm to room temperature, and to stir for 16 h. A yellow precipitate formed which was filtered and washed with ether three times. 97.2 g of EX-6B was isolated in 62% yield.

(EX-6C) A mixture of calcium hydride in THF was cooled to 0° C. and treated with neat EX-6B followed by neat t-butyl bromoacetate. The reaction mixture was allowed to stir at 0° C. for 1 h. The reaction mixture was then allowed to stir for 2 h after the mixture was allowed to warm to room temperature. The reaction mixture was heated to reflux temperature for 16 h. After the reaction mixture was cooled to room temperature, the mixture was slowly poured into a 1 L ice water slurry. The quenched mixture was extracted with dichloromethane (3×500 mL). The organic layers were combined and washed with water and brine. After the organic layer was dried over $MgSO_4$ and filtered, the volatile components were removed in vacuo to afford 28.81 g (90%) of EX-6C as an off white solid as a mixture of N-alkylated and O-alkylated isomers (9:1). N-alkylated isomer: $^1H$ NMR (300 MHz, $CDCl_3$) d 8.07 (s, 1H), 4.75 (s, 2H), 2.57 (s, 3H), 1.47 (s, 9H); $^{13}C$ NMR (75 MHz, $CDCl_3$) d 165.1, 162.7, 158.4, 152.5, 108.3, 83.7, 46.8, 28.2 (3C), 15.5; HRMS (EI) calcd for $C_{11}H_{15}BrN_2O_3S$ 335.0065, found 335.0077.

(EX-6D) In an argon-filled glove box a 12 ounce Fischer-Porter bottle containing a magnetic stir bar was charged with EX-6C (5.00 g, 15.0 mmol), $Pd(OAc)_2$ (168 mg, 0.75 mmol, 5 mole %), rac-BINAP (654 mg, 1.05 mmol, 7 mole %), $Cs_2CO_3$ (6.84 g, 21.0 mmol), and anhydrous, degassed toluene (65.0 ml). To this mixture was added isopropyl amine (3.00 ml. 35.2 mmol). The bottle was capped with a pressure head fitted with a pressure gauge and removed from the glove box. The closed-system was heated in an oil bath at 118–120° C. with magnetic stirring for 16 h thereafter. A head-space pressure of ~10 psi was developed during the reaction. The Fischer-Porter bottle containing the reaction mixture was removed from the oil bath, allowed to cool for 30 min, vented to an argon-flow system and sampled by syringe. LCMS analysis showed 35% product with 65% starting material remaning. Under a blanket of argon, the pressure head was removed and the reaction mixture was treated with $Pd(OAc)_2$ (337 mg, 1.5 mmol, 10 mole %), rac-BINAP (1.00 g, 1.6 mmol, 11 mole %), $Cs_2CO_3$ (10.0 g, 30.7 mmol), and isopropyl amine (6.00 ml, 70.4 mmol). The bottle was capped with the pressure head and again heated to 118–120° C. with magnetic stirring for 16 h. The sampling procedure was repeated and LCMS revealed that the reaction was complete. The reaction mixture was allowed to cool to RT and filtered through a medium frit sintered-glass funnel. The solids were washed thoroughly with toluene and discarded. The filtrate was concentrated and purified by flash chromatography (Merck 230–400 mesh $SiO_2$, 10% ethyl acetate in hexanes) to afford 3.80 g (81% yield) of (EX-6D)

as a tan solid: ¹H NMR (300 MHz, CDCl₃) d 7.05 (s, 1H), 4.74 (s, 2H), 3.44 (septet, J=6.3 Hz, 1H), 2.53 (s, 3H), 1.47 (s, 9H), 1.21 (d, J=6.3 Hz, 6H); ¹³C NMR (75 MHz, CDCl₃) d 165.7(s), 158.7(s), 147.4(s), 130.5(s), 123.6(d), 82.9(s), 45.9(t), 44.1d, 28.0 (q), 22.1 (q), 14.8(q); HRMS (ESI) calcd for C₁₄H₂₄N₃SO₃ [M+H]⁺=314.1538, found 314.1539.

(EX-6E) In an argon-filled glove box a 3-ounce Fischer-Porter bottle containing a magnetic stir bar was charged with EX-6D (1.00 g, 3.20 mmol), 3-nitrophenyl boronic acid (634 mg, 3.80 mmol), Cu(I)-2-thiophenecarboxylate (1.21 g, 6.37 mmol), and Pd(PPh3)₄ (100 mg, 0.86 mmol, 2.7 mol %). THF (25 ml) was added and the bottle was capped with a pressure head fitted with a pressure gauge and removed from the glove box. The closed-system was heated in an oil bath at 70° C. with magnetic stirring for 16 h thereafter. The reaction mixture was allowed to cool to RT, vented and diluted with ether (200 ml). The mixture was filtered through a medium frit sintered glass funnel. The green solid was washed with ether (100 ml) and discarded. The filtrate was concentrated and purified by flash chromatography (Merck 230–400 mesh SiO₂, 10% ethyl acetate in hexanes to 30%) to afford 961 mg (78% yield) of EX-6E as a yellow foam: ¹H NMR (300 MHz, CDCl₃) d 8.39 (s, 1H), 8.31 (d, J=8.1 Hz, 1H), 7.86 (d, J=7.8 Hz, 1H), 7.64 (t, J=8.1 Hz, 1H), 7.15 (bs, 1H), 4.51 (s, 2H), 3.58 (septet, J=6.0 Hz, 1H), 1.46 (s, 9H), 1.27 (d, J=6.3 Hz, 6H); HRMS (ESI) calcd for C₁₉H₂₅N₄O₅ [M+H]⁺=389.1815, found 389.1825.

(EX-6F) A 250-mL round-bottom flask fitted with a magnetic stir bar was charged with EX-6E (755 mg, 1.9 mmol) and trifluoroacetic acid (30 mL). This mixture was stirred at RT under an argon-flow atmosphere for 30 min and concentrated on a rotary evaporator. The residue was triturated with ether (50 mL) and coevaporated with heptane (2×50 mL) to afford 801 mg (95% yield) of EX-6F as a clear yellow glass: ¹H NMR (300 MHz, DMSO-d₆) d 834–8.26 (m, 2H), 7.89 (d, J=7.8 Hz, 1H), 7.76 (t, J=7.9 Hz, 1H), 7.20 (s, 1H), 4.51 (s, 2H), 3.57 (septet, J=6.6 Hz, 1H), 1.17 (d, J=6.6 Hz, 6H); HRMS (ESI) calcd for C₁₅H₁₇N₄O₅ [M+H]⁺ of free base=333.1223, found 333.1199.

Prepared from EX-6F according to the procedure described for the CBZ-protected precursor to afford the product ¹H NMR (300 MHz, CDCl₃) d 9.34 (bs, 1H), 832 (s, 1H), 8.14 (d, J=8.0 Hz, 1H), 7.81 (t, J=7.8 Hz, 2H), 7.53 (d, J=7.8 Hz, 2H), 7.47 (t, J=7.8 Hz, 1H), 7.39–7.25 (m, 5H), 7.08 (s, 1H), 7.00 (d, J=7.8 Hz, 2H), 5.12 (s, 2H), 4.61 (d, J=7.8 Hz, 1H), 4.35 (s, 2 H), 421 (m, 1H), 3.50 (d of septets, 8 lines J=6.3 Hz, 1H), 1.22 (d, J=6.3 Hz, 6H); ¹³C NMR (75 MHz CDCl₃) d 168.5 (s), 167.4 (s), 164.0 (s), 158.6 (s), 148.2 (s), 143.8 (s), 142.6 (s), 136.6 (s), 136.2 (s), 135.0 (d), 133.4 (s), 133.2 (s), 129.9 (d), 128.7 (d), 128.3 (d), 127.8 (d), 127.5 (d), 124.4 (d), 124.1 (d), 121.8 (d), 67.4 (t), 49.9 (t), 44.1 (d), 43.2 (t), 22.4 (q); HRMS (ESI) calcd for C₃₁H₃₂N₇O₆ [M+H]⁺: 598.2463, found 598.2414.

Prepared from EX-6G a g to the method described for SC-81703 to afford the product: ¹H NMR (300 MHz, CD₃OD) d 9.25 (bs, 1H), 8.97 (m, 1H), 8.78 (bs, 1H), 7.93–7.14 (complex m, 9H), 4.77 (s, 2H), 4.51 (s, 3H), 3.66 (m, 1H), 1.30 (d, J=6.3 Hz, 6H); HRMS (ESI) calcd for C₂₃H₂₈N₇O₂ [M+H]⁺=598 of free base 434.2304, found 434.2318.

Example 7

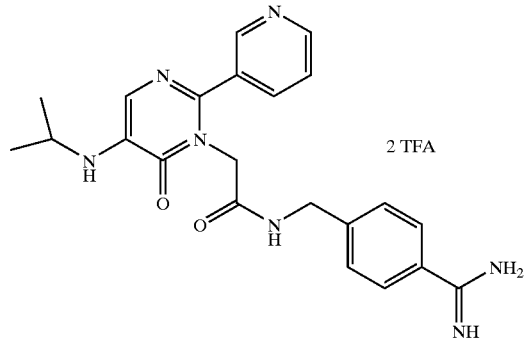

(EX-7A) Prepared from EX-CD using the same procedure described for EX-6E with the only exception that Cs₂CO₃ base was used. As such, EX-6D (213 mg, 0.68 mmol), pyridine-3-boronic acid 1,3-propanediol cyclic ester (166 mg, 1.02 mmol) and Cs₂CO₃ (771 mg, 2.37 mmol) afforded 143 mg of EX-7A (61% yield) after flash chromatography (Merck 230–400 mesh SiO₂, 2% MeOH in CHCl₃) as a slightly yellow glass: ¹H NMR (300 MHz, CDCl₃) d 8.79–8.66 (m, 2H), 7.90–7.26 (complex m, 3H), 7.16 (s, 1H), 4.53 (s, 2H), 3.57 (septet, J=6.3 Hz, 1H), 1.44 (s, 9H), 1.27 (d, J=6.3 Hz, 6H); HRMS (ESI) calcd for C₁₈H₂₅N₄O₃ [M+H]⁺=345.1927, found 345.1928.

(EX-7B) Prepared from EX-7A (143 mg, 0.41 mmol) using the same procedure described for EX-6F to afford 212 mg (100% yield) of EX-7B as a yellow foam: ¹H NMR (300 MHz, CDCl₃) d 8.72–8.64 (m, 2H), 7.95–7.89 (m, 1H), 7.62–7.52 (complex m, 2H), 7.42–7.37 (m, 1H), 7.20 (s, 1H), 4.52 (s, 2H), 3.57 (septet, J=6.3 Hz, 1H), 1.18 (d, J=6.3 Hz, 6H); HRMS (ESI) calcd for C₁₄H₁₇N₄O₃ [M+H]⁺ 289.1301, found 289.1296.

(EX-7C) Prepared from EX-7B using the same procedure described for the CBZ-protected material to afford EX-7C; HRMS (ESI) calcd for C₃₀H₃₂N₇O₄ [M+H]³⁰ =554.2516, found 554.2523.

Prepared from EX-7C using the same procedure described for Example 6 to afford the product.

Example 8

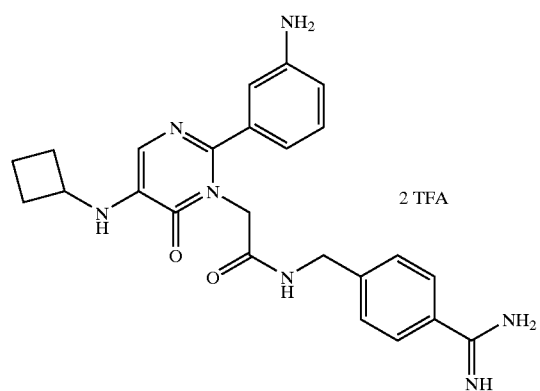

By following the method of Example 6, the title compound was prepared: HRMS (ESI) calcd for C₂₄H₂₇N₇O₂ [M+H]⁺ 446.2304, found 446.2309.

Methylene analogs of pyrimidinones wherein a methylene is present as a replacement for the carbonyl of the acetamide at the N-3 position of the pyrimidinone can be prepared using Scheme 8 "A General Methylene Pyrimidinone Preparation" as detailed below along with the specific Example 9.

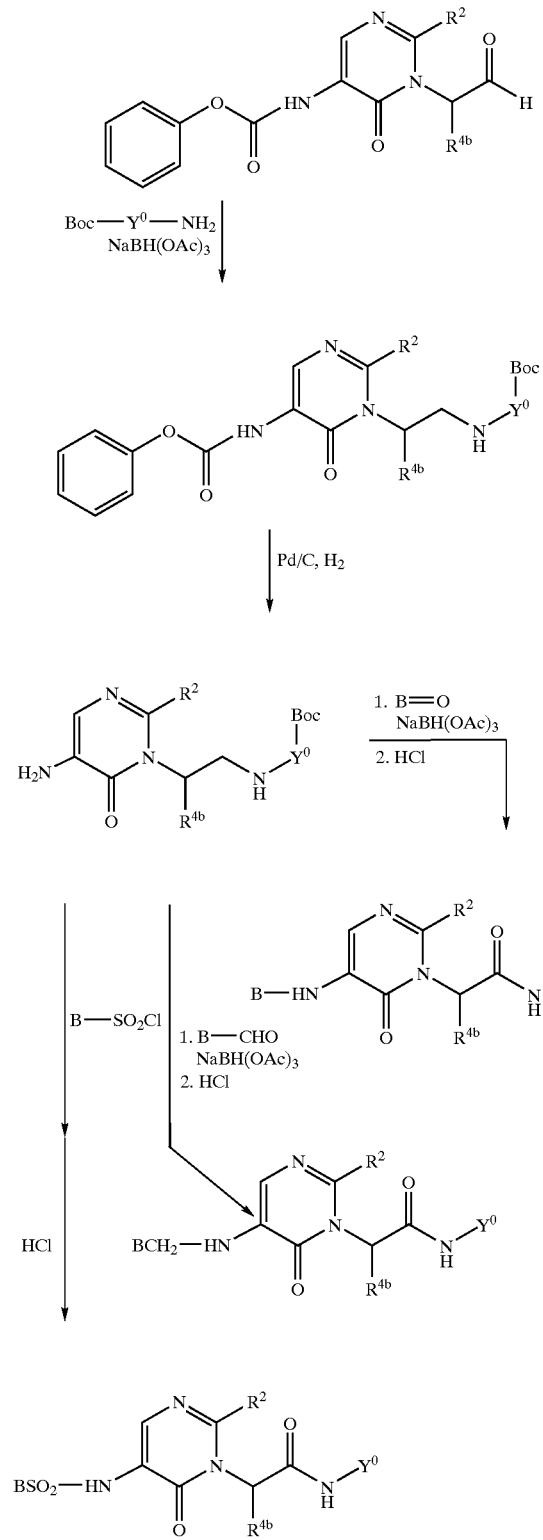

Example 9

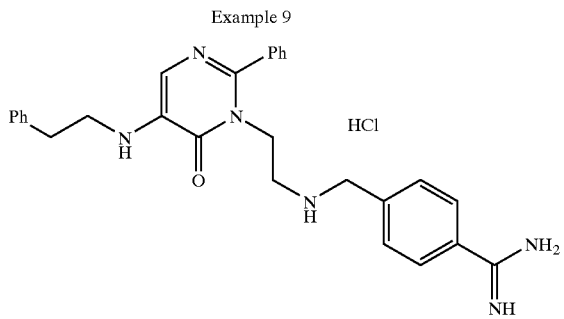

EX-9A) To a solution of [[5-[(benzyloxycarbonyl)amino]-2-phenyl-6-oxo-1,6-dihydro-1-pyrimidinyl]acetaldehyde in tetrahydrofuran and dichloromethane (1:1, 0.3 M) is added a catalytic amount of acetic acid and 1 equivalent of the appropriate amine. The solution is cooled to 0° C. in an ice bath, and 1 equivalent sodium triacetoxyborohydride is added in one portion. After stirring for 5 minutes, the ice bath is removed, and the reaction mixture is allowed to stir at room temperature for 2 hours. The reaction is quenched by the addition of 1 N NaOH, and the mixture is stirred for 5 minutes. Typical aqueous work up is followed by chromatographic purification to provide pure product EX-9A.

EX-9B) To a solution of [5-[(benzyloxycarbonyl)amino]-2-phenyl-6-oxo-1,6-dihydro-1-pyrimidinyl]acetamide (EX-9A) in methanol (0.2 M) is added 10% Pd/C in one portion. The resulting mixture is stirred under an atmosphere of hydrogen gas (balloon) at room temperature for approximately 16 hours. The crude reaction mixture is filtered through a pad of Celite 545, and the solvent is removed under reduced pressure. Trituration of the residue from ethyl ether gives pure product EX-9B.

EX-9C) To a solution of [5-amino-2-phenyl-6-oxo-1,6-dihydro-1-pyrimidinyl]acetamide (EX-9B) in tetrahydrofuran and dichloromethane (1:1, 0.3 M) is added a catalytic amount of acetic acid and 1 equivalent phenylacetaldehyde. The solution is cooled to 0° C. in an ice bath, and 1 equivalent sodium triacetoxyborohydride is added in one portion. After stirring for 5 minutes, the ice bath is removed, and the reaction mixture is allowed to stir at room tempemaure for 2 hours. The reaction is quenched by the addition of 1 N NaOH, and the mixture is stirred for 5 minutes. Typical aqueous work up is followed by chromatographic purification to provide pure product EX-9C.

A solution of [5-(2-phenylethyl)amino-2-phenyl-6-oxo-1,6-dihydro-1-pyrimidinyl]acetamide in 4M HCl dioxane (0.2 M) is stirred for several hours. After the reaction is complete, the volatiles are removed under reduced pressure. The residue is purified by trituation with ethyl ether to afford pure product 5.

Sulfonyl analogs of pyrimidinones wherein a sulfonyl is present as a replacement for the carbonyl of the acetamide at the N-3 position of the pyrimidinone can be prepared using procedures generally based on those disclosed in Schemes 1–5 by substituting an appropriate aminomethanesulfonamide of an N-Boc-amidino-protected amine in place of the 1,1-dimethoxyethylamine. For example, the N-(4-amidinobenzyl)2-aminomethanesulfonamide can be used. Using this approach, sulfonyl analogs in Examples 10 and 11 can be prepared.

Example 10

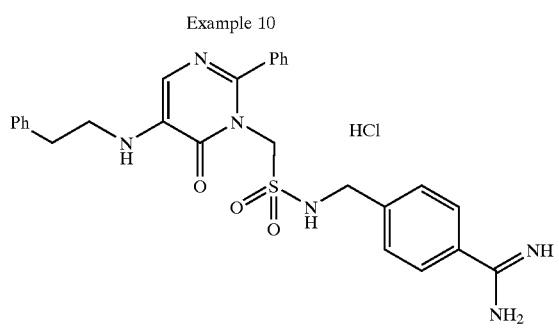

Example 11

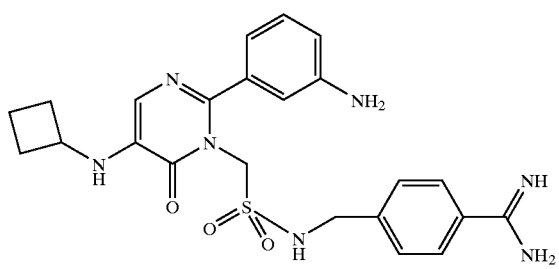

Triazinone analogs of pyrimidinones wherein a nitrogen is present as a replacement for the carbon at the 4-position of the pyrimidinone can be prepared usmig Scheme 9 "A Genral 4-Aza Pyrimidinone Preparation" as detailed below along with the specific Example 12.

Scheme 9: General 4-AzaPyrimidinon Synthesis

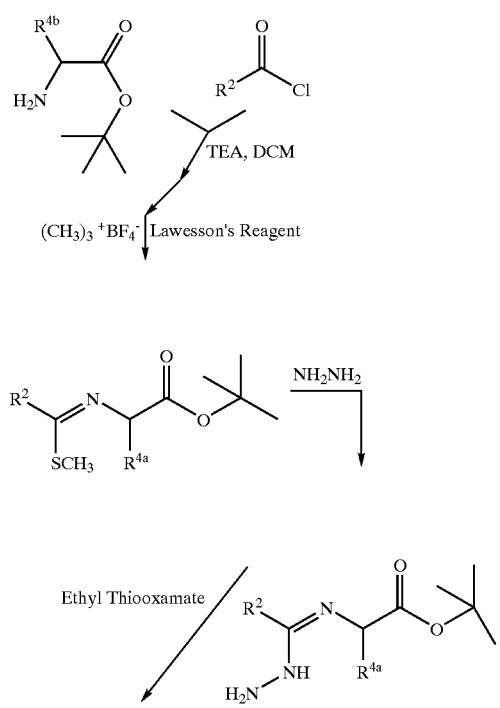

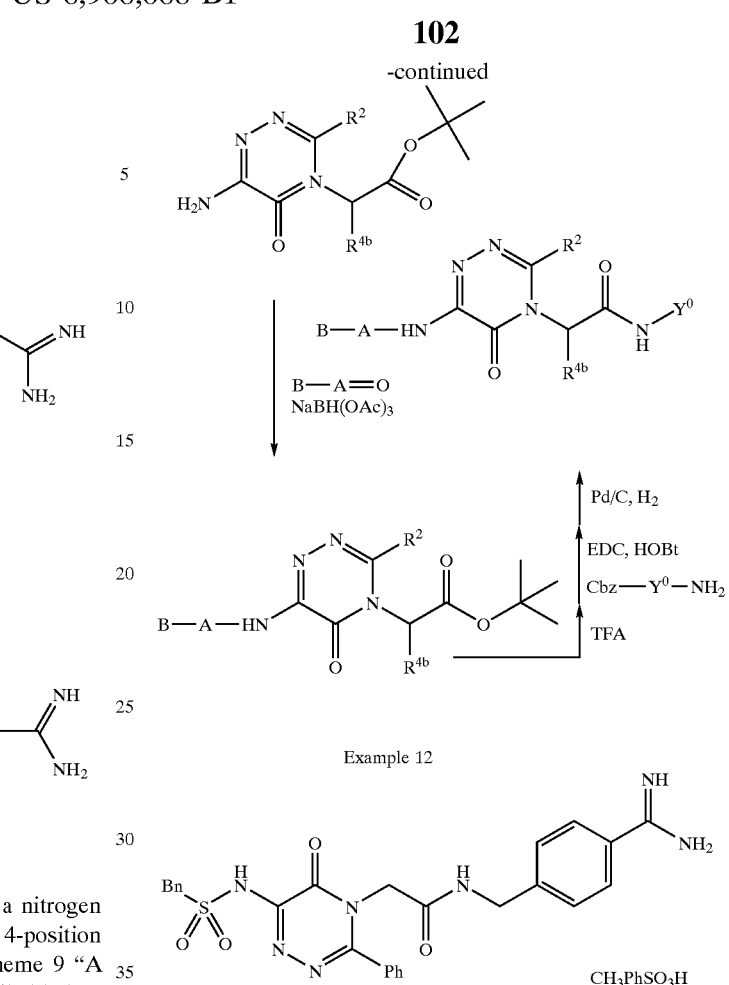

Example 12

EX-12) A solution of glycine t-butyl ester hydrochloride (1 mmol) in dichloromethane is treated with benzoyl chloride (1 mmol) and triethyl amine (2 mmol). The reaction mixture is allowed to stir at room temperature for 16 h. The mixture is washed with water and extracted with dichloromethane. The combined organic layers are dried over $MgSO_4$. After removing the volatiles in vacuo pure product EX-12A is isolated.

EX-12B) A mixture of N-benzoylglycine t-butyl ester (1 mmol; EX-12A), Lawesson's reagent (0.5 mmol) and toluene are heated to 80° C. for 16 h. The reaction mixture is concentrated under reduced pressure. Purification via column chromatography on silica gel gives pure product EX-12B.

EX-12C) A mixture of N-thiobenzoylglycine t-butyl ester (1 mmol; EX-12B) in dichloromethane is treated with trimethyloxonium tetrafluoroborate (1.1 mmol) at −78° C. After stirring the reaction mixture for 2 h, the mixture is washed with $NaHCO_3$ (aq) and extracted with dichloromethane. The combined organic layers are dried over $MgSO_4$ and filtered. After concentration of the volatile organic components, the desired product EX-12C is isolated.

EX-12D) A solution of N-thiomethylbenzylglycine t-butyl ester (1 mmol; EX-12C) in methanol is treated with hydrazine (1 mmol). The volatile materials are removed in vacuo, and the desired ccmpound EX-12D is isolated without further purification.

EX-12E) A mixture of compound EX-12D (1 mmol) and ethyl thiooxamate (1 mmol) in methanol is heated to reflux temperature for 4 h. A precipitation of colorless crystals occurs, and the crystals of the desired product EX-12E are isolated by suction filtration.

A solution of compound EX-12E (1 mmol) and pyridine (5 mmol) in acetonitrile is treated with a solution of a-toluenesulfonyl chloride (3 mmol) in acetonitrile. The reaction mixture is stirred at −10° C. to 0° C. for 3 h. A white precipitate forms after the reaction is complete. The crystals of the desired product EX-12F are isolated by suction filtration.

EX-12G) Trifluoroacetic acid is added to a mixture of compound EX-12F (1 mmol) in anisole at 0° C. The reation mixture is allowed to stir at 0° C. for 1 h. The reaction mixture is extracted with an organic solvent. Removal of the organic solvent under reduced pressure gives pure product EX-12G.

EX-12H) Compound EX-12G (1 mmol), EDC(1.3 mmol), and HOBt (1.3 mmol) are mixed in DMF, and the mixture is stirred at 20° C. for 15 minutes. To this mixture is added a solution of benzyl-[[(4-aminomethylphenyl)iminomethyl] amino]carbamate hydrogen chloride salt (1.3 mmol) and DIEA (1.3 mmol) in DMF. Typical aqueous work-up is followed by chromatographic purification to provide the desired product EX-12H.

Compound EX-12H (1 mmol), p-toluene sulfonic acid mono hydrate (1 mmol) and 10% Pd on activated carbon (0.1 mmol) are mixed with methanol. The mixture is stirred for 2 h under hydrogen atmosphere which is introduced and maintained through a rubber balloon. After filtering off the catalyst and removing the methanol, the desired product is isolated.

Formula (I) compounds of this invention possessing hydroxyl, thiol, and amine functional groups can be converted to a wide variety derivatives. Altenatively, derivatized Formula (I) compounds can be obtained by first derivatizing one or more intermediates in the processes of preparation before further transforming the derivatized intermediate to comounds of Formula (I). A hydroxyl group in the form of an alcohol or phenol can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. Similarly, carbarnic acid esters (urethanes) can be obtained by reacting a hydroxyl group with isocyanates and carbamoyl chlorides. Sulfonate, phosphonate, and phosphate esters can be prepared using the corresponding acid chloride and similar reagents. Compounds of Formula (I) that have at least one thiol group present can be converted to the corresponding thioesters derivatives analogous to those of alcohols and phenols using the same reagents and comparable reaction conditions. Compounds of Formula (I) that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide or a tertiary amine. Suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formula (I) are available from commercial sources or the references cited above, which are incorporated herein by reference.

Formula (I) compounds of this invention possessing hydroxyl, thiol, and amine functional groups can be alkylated to a wide variety of derivatives. Alternatively, alkylated Formula (I) compounds can be obtained by first alkylating one or more intermediates in the processes of preparation before further transforming the alkylated intermediate to comounds of Formula (I). A hydroxyl group of compounds of Formula (I) can be readily converted to ether Alkylation to form an ether is readily effected using a suitable alkylating reagent such as an alkyl bromide, alkyl iodide or alkyl sulfonate. The coresponding aralkyl, heteroaralkyl, alkoxyalkyl, aralkyloxyalkyl, and hetetoaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents, amine catalyst such as pyridine in an inert solvent. Compounds of Formula (I) that have at least one thiol group present can be converted to the corresponding thioether derivatives analogous to those of alcohols and phenols using the same reagents and comparable reaction conditions. Compounds of Formula (I) that have at least one primary, secondary or tertiary amine group present can be converted to the corresponding secondary tertiary or quaternary ammonium derivative. Quaternary ammonium derivatives can be prepared using the appropriate bromides. iodides, and sulfonates analogous to those used with alcohols and phenols. Conditions involve reaction of the amine by warming it with the alkylating reagent with a stoichiometric amount of the amine (ie., one equivalent with a tertiary amine, two with a secondary, and three with a primary). With primary and secondary amines, two and one equivalents, respectively, of an acid scavenger are used concurrently. Secondary or tertiary amines can be prepared from the corresponding primary or secondary amine. A primary amine can be dialkylated by reductive amination using an aldehyde, such as formaldehyde, and sodium cyanoborohydride in the presence of glacial acetic acid. A primary amine can be monoalkylated by first monoprotecting the amine with a ready cleaved protecting group, such as trifluoroacetyl. An alkylating agent, such as dimethylsulfate, in the presence of a non-nucleophilic base, such as Barton's base (2-tert-butyl-1,1,3,3-tetramethylguanidine), gives the monomethylated protected amine. Removal of the protecting group using aqueous potassium hydroxide gives the desired monoalkylated amine. Additional suitable procedures and methods for preparing these derivatives can be found in House's Modern Synthetic Reactions, W. A. Benjamin, Inc., Shriner, Fuson, and Curtin in. The Systematic Identification of Organic Compounds, 5th Edition, John Wiley & Sons, and Fieser and Fieser in Reagents for Organic Synthesis published by John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formula (I) are available from commercial sources or the references cited above, which are incorporated herein by reference.

The results of the aforementioned synthetic approaches to the preparation pyrimidinones by derivatization of a nucleophilic substituent such as may be present in B, $R^1$, $R^2$ and $Y^0$ are shown in Table 1 for the specific Examples 13 through 19. The specific examples recited below should be considered a being merely illustrative of the wide variety possible and not as limiting to one of ordinary skill in the art.

TABLE 1

Structures of Pyrimidinones Prepared by
General Derivatization Procedures

General Structure

| Ex. No. | $R^2$ | B—A— | $Y^0$ | MW (m/z + 1) |
|---|---|---|---|---|
| 13 | phenyl | methoxyacetyl | 4-amidinobenzyl | 449.47 |
| 14 | phenyl | 4-methylbenzoyl | 4-amidinobenzyl | 495.54 |
| 15 | phenyl | 4-nitrobenzoyl | 4-amidinobenzyl | 526.52 |
| 16 | phenyl | isobutyryl | 4-amidinobenzyl | 447.50 |
| 17 | phenyl | 2,4,6-trimethylbenzoyl | 4-amidinobenzyl | 523.60 |
| 18 | phenyl | benzoyl | 4-amidinobenzyl | 481.52 |
| 19 | phenyl | acetyl | 4-amidobenzyl | 419.45 |

Assays for Biological Activity

TF-VIIa Assay

In this assy 100 nM recombinant soluble tissue factor and 2 nM recombinant human factor VIIa are added to a 96-well assay plate containing 0.4 mM of the substrate, N-Methylsulfonyl-D-phe-gly-arg-p-nitroaniline and either inhibitor or buffer (5 mM $CaCl_2$, 50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of TF-VIIa activity is calculated from $OD_{405\ nm}$ value from the experimental and control sample.

Xa Assay 0.3 nM human factor Xa and 0.15 mM N-α-Benzyloxycarbonyl-D-arginyl-L-glycyl-L-arginine-p-nitroaniline-dihydrochloride (S-2765) are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the ieaction at 405 nm for the release of p-nitroaniline. Percent inhibition of Xa activity is calculated from $OD_{405\ nm}$ value from the experimental and control sample.

Thrombin Assay 0.28 nM human thrombin and 0.06 mM H-D-Phenylalanyl-L-pipecolyl-L-arginine-p-nitroaniline dibydrochloride are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of thrombin activity is calculated from $OD_{405\ nm}$ value from the experimental and control sample.

Trypsin Assay 5 ug/ml trypsin, type IX from porcine pancreas and 0.375 mM N-α-Benzoyl-L-arginine-p-nitroanilide (L-BAPNA) are added to a 96-well assay plate containing either inhibitor or buffer (50 mM Tris-HCl, pH 8.0, 100 mM NaCl, 0.1% BSA). The reactions, in a final volume of 100 ul are measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of trypsin activity is calculated from $OD_{405\ nm}$ value from the experimental and control sample.

Recombinant soluble TF, consisting of amino acids 1–219 of the mature protein sequence was expressed in *E. coli* and purified using a Mono Q Sepharose FPLC. Recombinant human VIIa was purchased from American Diagnostica, Greenwich Conn. and chromogenic substrate N-Methylsulfonyl-D-phe-gly-arg-p-nitroaniline was prepared by American Peptide Company, Inc., Sunnyvale, Calif. Factor Xa was obtained from Enzyme Research Laboratories, South Bend Ind., thrombin from Calbiochem, La Jolla, Calif., and trypsin and L-BAPNA from Sigma, St. Louis Mo. The chromogenic substrates S-2765 and S-2238 were purchased from Chromog nix, Sweden.

The biological activity of the compounds of Examples 1 through 19 as determined by the bioassay procedures is summarized in the Table 2.

TABLE 2

Inhibitory Activity of Pyrimidinones
toward Factor Xa, TF-VIIA, Thrombin II,
and Trypsin II.

| Example Number | TF-VIIA IC50 (uM) | Thrombin II IC50 (uM) | Factor Xa IC50 (uM) | Trpysin II IC50 (uM) |
|---|---|---|---|---|
| 1 | 15.4 | 22.4 | — | 0.5 |
| 2 | >30 | >30 | — | >30 |
| 3 | 1.0 | 1.0 | — | 0.6 |
| 4 | — | — | — | — |
| 5 | — | — | — | — |
| 6 | 0.05 | 43% @ 30 um | 33% @ 30 uM | <0.04 |
| 7 | 0.7 | 11.3 | 33% @ 30 uM | 0.04 |
| 8 | 0.08 | 42% @ 30 uM | 15% @ 30 uM | 0.04 |
| 9 | — | — | — | — |
| 10 | — | — | — | — |
| 11 | — | — | — | — |
| 12 | — | — | — | — |
| 13 | — | — | — | — |
| 14 | — | — | — | — |
| 15 | — | — | — | — |
| 16 | — | — | — | — |
| 17 | — | — | — | — |
| 18 | — | — | — | — |
| 19 | — | — | — | — |

What we claim is:

1. A compound having the Formula:

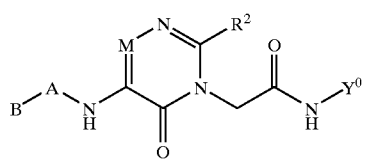

Formula (I)

or a pharmaceutically acceptable salt thereof, wherein;

B is:

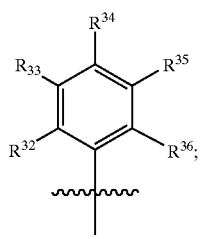

$R^{32}$, $R^{33}$, $R^{34}$, $R^{35}$, and $R^{36}$ are independently selected from the group consisting of hydrogen, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}—(W^7)_{rr}$ wherein rr is an integer selected from 0 through 1, pa is an integer selected from 0 through 3, and $W^7$ is $N(R^7)$;

$R^7$ is selected from the group consisting of hydrogen and alkyl;

$R^{15}$ is selected from the group consisting of hydrogen, halo, alkyl, and haloalkyl;

M is N;

R;

$R^2$ is $Z^0$—Q;

$Z^0$ is a covalent single bond;

Q is selected from the group consisting of aryl and 5- or 6-membered heteroaryl wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrogen, hydroxy, amino, amidino, guanidino, lower alkylamino, alkylthio, alkoxy, alkylsulfinyl, alkylsulfonyl, amidosulfonyl, monoalkylamidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrogen, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyamido, carboxyalkyl, and cyano;

$Y^0$ is formula (IV):

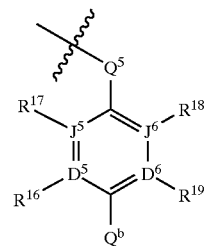

wherein $D^5$, $D^6$, $J^5$, and $J^6$ are independently selected from the group consisting of C, N, O, S and a covalent bond with the provisos that no more than one is a covalent bond, no more than one of $D^5$, $D^6$, $J^5$, and $J^6$ is O, no more than one of $D^5$, $D^6$, $J^5$, an $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrogen, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$Q^b$ is selected from the group consisting of $NR^{20}R^{21}$, hydrogen, and $C(NR^{25})NR^{23}R^{24}$;

$R^{20}$, $R^{21}$, $R^{23}$, $R^{24}$, and $R^{25}$ are independently selected from the group consisting of hydrogen and alkyl; and $Q^s$ is $CH_2$.

2. The compound as recited in claim 1 or a pharmaceutically acceptable salt thereof, wherein;

$R^{32}$, $R^{33}$, $R^{34}$, $R^{35}$, and $R^{36}$ are independently selected from the group consisting of hydrogen, amidino, guanidino, methyl, ethyl, methoxy, ethoxy, hydroxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, N(CH$_3$), CH$_2$, CH$_3$CH, and CH$_2$CH$_2$;

M is N;

$R^2$ is selected from the group consisting of phenyl and 2-thienyl, 2-furyl, 2-pyrrolyl, 2-imidazolyl, 2-thiazolyl, 3-isoxazolyl, 2-pyridyl, and 3-pyridyl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrogen, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrogen, amidino, amidocarbonyl, N-methylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, amidosulfonyl, N-methylamidosulfonyl, N,N-dimethylamidosulfonyl, methoxycarbonyl, fluoro, chloro, bromo, and cyano;

$Y^0$ is selected from the group consisting of:

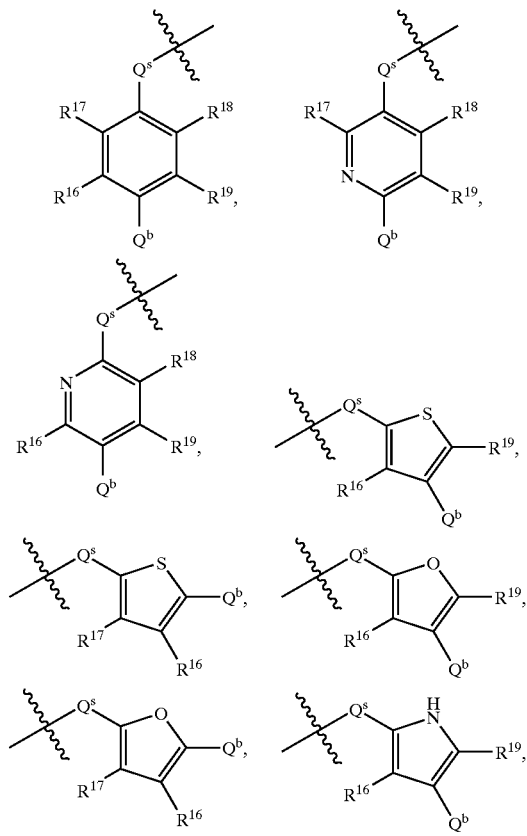

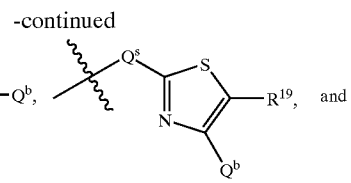

-continued

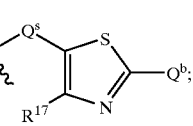

$R^{16}$, $R^{17}$, $R^{18}$, and $R^{19}$ are independently selected from the group consisting of hydrogen, methyl, ethyl, amidino, guanidino, methoxy, hydroxy, amino, aminomethyl, 1-aminoethyl, 2-aminoethyl, N-methylamino, dimethylamino, methylthio, ethylthio, trfluoromethylthio, methylsulfinyl, methylsulfonyl, trifluoromethyl, pentafluoroethyl, 2,2,2-trifluoroethyl, trifluoromethoxy, fluoro, chloro, amidosulfonyl, N-methylamidosulfonyl, hydroxymethyl, carboxo, and cyano.

$Q^b$ is selected from the group consisting of $NR^{20}R^{21}$ and $C(NR^{25})NR^{23}R^{24}$;

$R^{20}$, $R^{21}$, $R^{23}$, $R^{24}$, and $R^{25}$ are independently selected from the group consisting of hydrogen, methyl, and ethyl; and $Q^s$ is $CH_2$.

3. The compound as recited in claim 2 or a pharmaceutically acceptable salt thereof, wherein;

B is selected from the group consisting of 2-aminophenyl, 3-aminophenyl, 3-amidinophenyl, 4-amidinophenyl, 3-carboxyphenyl, 3-carboxy-5-hydroxyphenyl, 3-chlorophenyl, 4chlorophenyl, 3,4-dichlorophenyl, 2-fluorophenyl, 3-fluorophenyl, 3,4-difluorophenyl, 3-hydroxyphenyl, 4-hydroxyphenyl, 3-methoxyaminophenyl, 3-methoxyphenyl, 4-methoxyphenyl, 3-methylphenyl, 4-methylphenyl, and phenyl;

A is selected from the group consisting of $CH_2$, $CH_3CH$, $CF_3CH$, $NHC(O)$, $CH_2CH_2$, and $CH_2CH_2CH_2$;

M is N;

$R^2$ is selected from the group consisting of 5-amino-3-amidocarbonylphenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, benzyl, 3-carboxyphenyl, 3-carboxy-5-aminophenyl, 3-carboxy-5-hydroxyphenyl, 3-carboxymethyl-5-aminophenyl, 3-carboxymethyl-5-hydroxyphenyl, 3-carboxymethylphenyl, 3-chlorophenyl, 2-chlorophenyl, 3-cyanophenyl, 3-dimethylaminophenyl, 2-fluorophenyl, 3-fluorophenyl, 2,5-difluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl;

111

$Y^0$ is selected from the group consisting of:

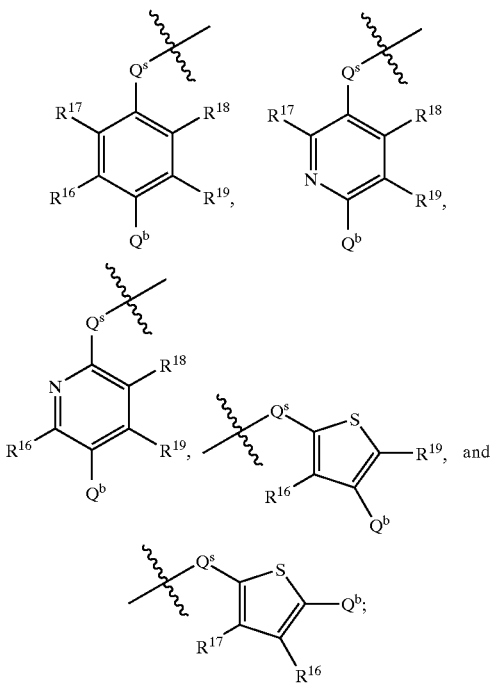

$R^{16}$ and $R^{19}$ are independently selected from the group consisting of hydrogen, amidino, amino, aminomethyl, methoxy, methylamino, hydroxy, hydroxymethyl, fluoro, chloro, and cyano;

$R^{17}$ and $R^{18}$ are independently selected from the group consisting of hydrogen, fluoro, chloro, hydroxy, hydroxymethyl, amino, carboxy, and cyano;

$Q^b$ is selected from the group consisting of hydrogen and $C(NR^{25})NR^{23}R^{24}$;

$R^{23}$, $R^{24}$, and $R^{25}$ are independently selected from the group consisting of hydrogen and methyl; and $Q^s$ is $CH_2$.

4. The compound as recited in claim 3 or a pharmaceutically acceptable salt thereof, wherein;

B is selected from the group consisting of 3-aminophenyl, 3-amidinophenyl, 4-amidinophenyl, 3-chlorophenyl, 4-chlorophenyl, 3,4-dichlorophenyl, 2-fluorophenyl, 4-methylphenyl, and phenyl;

A is selected from the group consisting of $CH_2$, NHC(O), $CH_2CH_2$, and $CH_2CH_2CH_2$;

M is N;

$R^2$ is selected from the group consisting of 3-aminophenyl, benzyl, 3-chlorophenyl, 3-dimethylaminophenyl, 3-hydroxyphenyl, 3-methanesulfonylaminophenyl, 3-methylaminophenyl, 2-methylphenyl, 3-methylphenyl, phenyl, 3-trifluoroacetamidophenyl, 3-bromo2-thienyl, 2-thienyl, and 3-thienyl; and $Y^0$ is selected from the group consisting of 5-amidino-2-thienylmethyl, 4-amidinobenzyl, 2-fluoro-4-amidinobenzyl, and 3-fluoro-4-amdinobenzyl.

5. A compound of claim 1, or a pharmaceutically acceptable salt thereof, wherein:

$R^2$ is 3-aminophenyl, B is 3-chlorophenyl, A is $CH_2CH_2$, $Y^0$ is 4-amidinobenzyl, and M is N;

$R^2$ is 3-aminophenyl, B is phenyl, A is $CH_2$, $Y^0$ is 4-amidinobenzyl, and M is N;

112

$R^2$ is phenyl, B is 3-chlorophenyl, A is $CH_2CH_2$, $Y^0$ is 4-amidinobenzyl, and M is N;

$R^2$ is 3-dimethylaminophenyl, B is phenyl, A is $CH_2CH_2$, $Y^0$ is 4-amidinobenzyl, and M is N;

$R^2$ is 2-methylphenyl, B is phenyl, A is $CH_2CH_2$, $Y^0$ is 4-amidinobenzyl, and M is N;

$R^2$ is phenyl, B is 3-aminophenyl, A is C(O)NH, $Y^0$ is 4-amidinobenzyl, and M is N;

$R^2$ is phenyl, B is 3-amidinophenyl, A is $CH_2$, $Y^0$ is 4-amidinobenzyl, and M is N;

$R^2$ is 3-(N-methylamino)phenyl, B is phenyl, A is $CH_2CH_2$, $Y^0$ is 4-amidinobenzyl, and M is N;

$R^2$ is 3-methylsulfonamidophenyl, B is phenyl, A is $CH_2CH_2$, $Y^0$ is 4-amidinobenzyl, and M is N;

$R^2$ is phenyl, B is 4-amidinophenyl, A is $CH_2$, $Y^0$ is 4-amidinobenzyl, and M is N;

$R^2$ is 3-methylaminophenyl, B is phenyl, A is $CH_2CH_2$, $Y^0$ is 4-amidinobenzyl, and M is N;

$R^2$ is phenyl, B is phenyl, A is $CH_2$, $Y^0$ is 4-amidinobenzyl, and M is N; or $R^2$ is 3-methylphenyl, B is 4-phenyl, A is $CH_2CH_2$, $Y^0$ is 4-amidinobenzyl, and M is N.

6. A compound having the Formula:

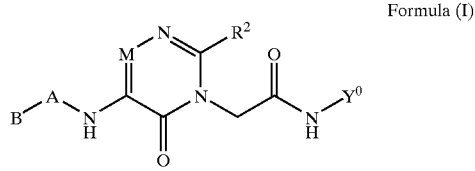

Formula (I)

or a pharmaceutically acceptable salt thereof, wherein;

B is selected from the group consisting of hydrogen, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrogen, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrogen and alkyl;

$R^{15}$ is selected from the group consisting of hydrogen, halo, alkyl, and haloalkyl;

M is N;

$R^2$ is $Z^0$—Q;

$Z^0$ is a covalent single bond;

Q is selected from the group consisting of aryl and heteroaryl wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrogen, hydroxy, amino, amidino, guanidino, lower alkylamino, alkylthio, alkoxy, alkylsulfinyl, alkylsulfonyl, amidosulfonyl, monoalkylamidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrogen, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyamido, carboxyalkyl, and cyano;

$Y^0$ is formula (IV):

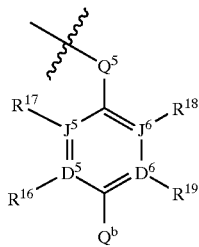

wherein $D^5$, $D^6$, $J^5$, and $J^6$ are independenty selected from the group consisting of C, N, O, S and a covalent bond with the provisos that no more than one is a covalent bond, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrogen, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalky, and cyano;

$Q^b$ is selected from the group consisting of $NR^{20}R^{21}$, hydrogen, $N(R^{26})C(NR^{25})N(R^{23})(R^{24})$, and $C(NR^{25})NR^{23}R^{24}$;

$R^{20}$, $R^{21}$, $R^{23}$, $R^{24}$, $R^{25}$, and $R^{26}$ are independently selected from the group consisting of hydrogen and alkyl; and $Q^s$ is $CH_2$.

7. The compound as recited in claim 6 or a pharmaceutically acceptable salt thereof, wherein;

B is selected from the group consisting of hydrogen, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl4-hexenyl, 1-methyl-2-hexynyl, 1-methyl-3-hexynyl, 1-methyl4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrogen, amidino, guanidino, methyl, ethyl, methoxy, ethoxy, hydroxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of:
  (i) single covalent bond, NH, $N(CH_3)$, $CH_2$, $CH_3CH$, and $CH_2CH_2$; and
  (ii) $CH_2N(CH_3)$, $CH_2N(CH_2CH_3)$, $CH_2CH_2N(CH_3)$, and $CH_2CH_2N(CH_2CH_3)$ with the proviso that B is hydrogen;

M is N;

$R^2$ is selected from the group consisting of phenyl and 2-thienyl, 2-furyl, 2-pyrrolyl, 2-imidazolyl, 2-thiazolyl, 3-isoxazolyl, 2-pyridyl, and 3-pyridyl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrogen, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrogen, amidino, amidocarbonyl, N-methylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, amidosulfonyl, N-methylamidosulfonyl, N,N-dimethylamidosulfonyl, methoxycarbonyl, fluoro, chloro, bromo, and cyano;

$Y^o$ is selected from the group consisting of:

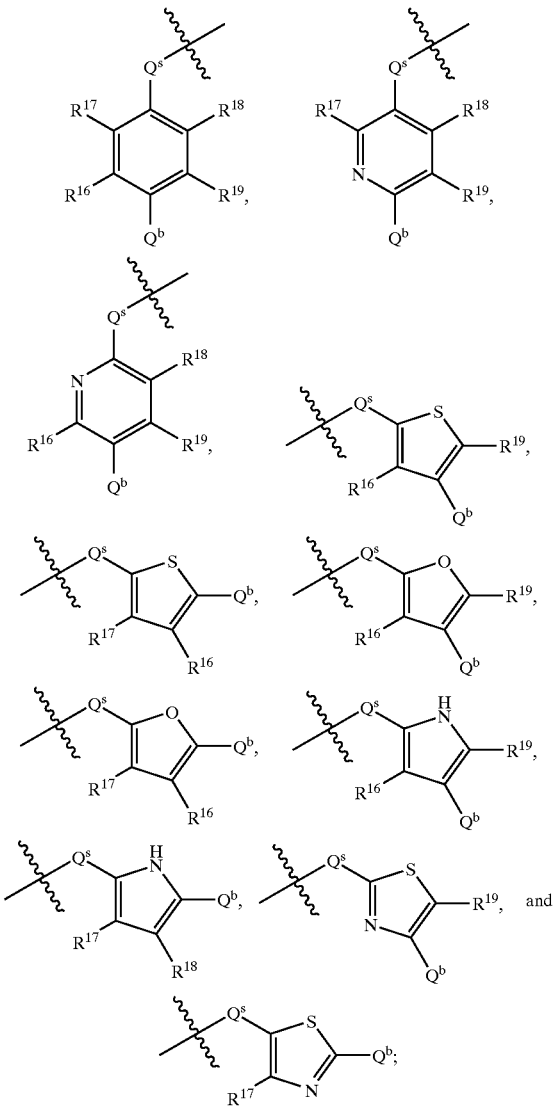

$R^{16}$, $R^{17}$, $R^{18}$, and $R^{19}$ are indenpendently selected from the group consisting of hydrogen, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, amidosulfonyl, N-methylamidosulfonyl, hydroxymethyl, carboxy, and cyano.

$Q^b$ is selected from the group consisting of $NR^{20}R^{21}$, $C(NR^{25})NR^{23}R^{24}$, and $N(R^{26})C(NR^{25})N(R^{23})(R^{24})$;

$R^{20}$, $R^{21}$, $R^{23}$, $R^{24}$, $R^{25}$, and $R^{26}$ are independenuy selected from the group consisting of hydrogen, methyl, and ethyl; and $Q^s$ is $CH_2$.

8. The compound as recited in claim 7 or a pharmaceutically acceptable salt thereof, wherein;

B is selected from the group consisting of hydrogen, ethyl, 2-propenyl, 2-propynyl, propyl, isopropyl, butyl, 2-butyl, (R)-2-butyl,(S)-2-butyl, tert-butyl, isobutyl, 1-pentyl, 3-pentyl, 2-methylbutyl, 2,2,2-trifluoroethyl, 6-amidocarbonylhexyl, 4-methyl-2-pentyl, 3-hydroxypropyl, 3-methoxy-2-propyl, 2-methoxyethyl, 2-methyl-2-butyl, 3-methyl-2-butyl, 2-dimethylaminopropyl, 2-cyanoethyl, 6-hydroxyhexyl, 2-hydroxyethyl, 2-amidinoethyl, 2-guanidinoethyl, 3-guanidinopropyl, 4-guanidinobutyl, 3-hydroxypropyl, 4-hydroxybutyl, 6-cyanohexyl, 2-dimethylaminoethyl, 3-methylbutyl, 2-methylbutyl, (S)-2-methylbutyl, 3-aminopropyl, 2-hexyl, and 4-aminobutyl;

A is selected from the group consisting of single covalent bond, $CH_2$, $CH_3CH$, and $CH_2CH_2$;

M is N;

$R^2$ is selected from the group consisting of 5-amino-3-amidocarbonylphenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, benzyl, 3-carboxyphenyl, 3-carboxy-5-aminophenyl, 3-carboxy-5-hydroxyphenyl, 3-carboxymethyl-5-aminophenyl, 3-carboxymethyl-5-hydroxyphenyl, 3-carboxymethylphenyl, 3-chlorophenyl, 2-chlorophenyl, 2,6-dichlorophenyl, 3-cyanophenyl, 3-dimethylaminophenyl, 2-fluorophenyl, 3-fluorophenyl, 2,5-difluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5amino-2-thienyl, 5-amino-3-thienyl, 3-bromo-2-thienyl, 3-pyridyl, 4-pyridyl, 2-thienyl, and 3-thienyl;

$Y^o$ is selected from the group consisting of:

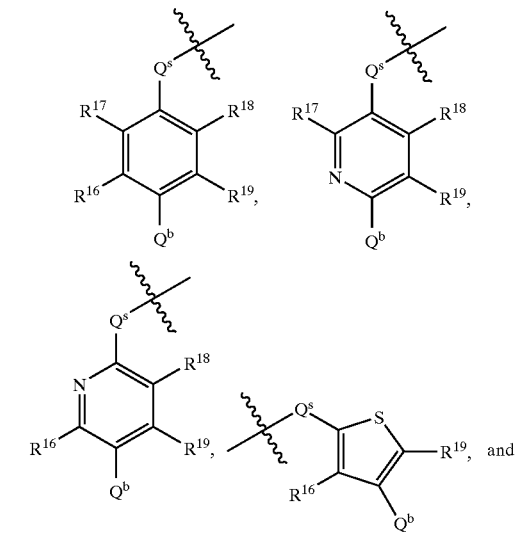

117

-continued

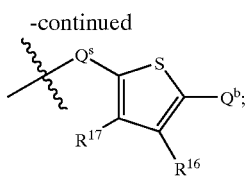

$R^{16}$ and $R^{19}$ are independently selected from the group consisting of hydrogen, amidino, amino, aminomethyl, methoxy, methylamino, hydroxy, hydroxymethyl, fluoro, chloro, and cyano;

$R^{17}$ and $R^{18}$ are independently selected from the group consisting of hydrogen, fluoro, chloro, hydroxy, hydroxymethyl, amino, carboxy, and cyano;

$Q^b$ is selected from the group consisting of hydrogen and $C(NR^{25})NR^{23}R^{24}$;

$R^{23}$, $R^{24}$, and $R^{25}$ are independently selected from the group consisting of hydrogen and methyl; and $Q^s$ is $CH_2$.

9. The compound as recited in claim 8 or a pharmaceutically acceptable salt thereof, wherein;

B is selected from the group consisting of hydrogen, ethyl, 2-propenyl, 2-propynyl, propyl, isopropyl, butyl, 2-butyl, (R)-2-butyl,(S)-2-butyl, tert-butyl, isobutyl, 1-pentyl, 3-pentyl, 2-methylbutyl, 2,2,2-trifluoroethyl, 6-amidocarbonylhexyl, 4-methyl-2-pentyl, 3-hydroxypropyl, 3-methoxy-2-propyl, 2-methoxyethyl, 2-methyl-2-butyl, 3-methyl-2-butyl, 2-dimethylaminopropyl, 2-cyanoethyl, 6-hydroxyhexyl, 2-hydroxyethyl, 2-amidinoethyl, 2-guanidinoethyl, 3-guanidinopropyl, 4guanidinobutyl, 3-hydroxypropyl, 4-hydroxybutyl, 6-cyanohexyl, 2-dimethylaminoethyl, 3-methylbutyl, 2-methylbutyl, (S)-2-methylbutyl, 3-aminopropyl, 2-hexyl, and 4-aminobutyl;

A is selected from the group consisting of single covalent bond, $CH_2$, $CH_3CH$, and $CH_2CH_2$;

M is N;

$R^2$ is selected from the group consisting of 5-amino-2-fluorophenyl, 3-amino-2-methylphenyl, 5-amino-2-methylthiophenyl, 3-aminophenyl, 3carboxyphenyl, 3-cyanophenyl, 3-methoxycarbonylphenyl, phenyl, and 3-pyridyl; and $Y^0$ is selected from the group consisting of 5-amidino-2-thienylmethyl, 4-amidinobenzyl, 2-fluoro4-amidinobenzyl, and 3-fluoro-4-amidinobenzyl.

10. A compound of claim 6, or a pharmaceutically acceptable salt thereof, wherein:

$R^2$ is 3-aminophenyl, B is 2,2,2-trifluoroethyl, A is single bond, $Y^0$ is 4-amidinobenzyl, and M is N;

$R^2$ is 3-aminophenyl, B is (S)-2-butyl, A is single bond, $Y^0$ is 4-amidinobenzyl, and M is N;

$R^2$ is 5-amino-2-fluorophenyl, B is isopropyl, A is single bond, $Y^0$ is 4-amidinobenzyl, and M is N;

$R^2$ is 2-methyl-3-aminophenyl, B is isopropyl, A is single bond, $Y^0$ is 4-amidinobenzyl, and M is N;

$R^2$ is 3-aminophenyl, B is ethyl, A is single bond, $Y^0$ is 4-amidinobenzyl, and M is N;

$R^2$ is 3-aminophenyl, B is ethyl, A is single bond, $Y^0$ is 4-amidino-2-fluorobenzyl, and M is N;

$R^2$ is 3-aminophenyl, B is 2-propenyl, A is single bond, $Y^0$ is 4-amidinobenzyl, and M is N;

$R^2$ is 3-aminophenyl, B is isopropyl, A is single bond, $Y^0$ is 4-amidino-2-fluorobenzyl, and M is N;

118

$R^2$ is 3-aminophenyl, B is isopropyl, A is single bond, $Y^0$ is 4-amidinobenzyl, and M is N;

$R^2$ is 3-aminophenyl, B is 2-butyl, A is single bond, $Y^0$ is 4-amidinobenzyl, and M is N;

$R^2$ is 3-aminophenyl, B is (R)-2-butyl, A is single bond, $Y^0$ is 4-amidinobenzyl, and M is N;

$R^2$ is 3-aminophenyl, B is 2-propynyl, A is single bond, $Y^0$ is 4-amidinobenzyl, and M is N;

$R^2$ is 3-aminophenyl, B is 3-pentyl, A is single bond, $Y^0$ is 4-amidinobenzyl, and M is N;

$R^2$ is 3-aminophenyl, B is hydrido, A is $CH_2$, $Y^0$ is 4-amidinobenzyl, and M is N;

$R^2$ is 3-aminophenyl, B is ethyl, A is $CH_2$, $Y^0$ is 4-amidinobenzyl, and M is N;

$R^2$ is 3-aminophenyl, B is 2-methypropyl, A is single bond, $Y^0$ is 4-amidinobenzyl, and M is N;

$R^2$ is 3-aminophenyl, B is 2-propyl, A is $CH_3CH$, $Y^0$ is 4-amidinobenzyl, and M is N;

$R^2$ is 3-aminophenyl, B is propyl, A is single bond, $Y^0$ is 4-amidino-2-fluorobenzyl, and M is N;

$R^2$ is 3-aminophenyl, B is 6-amidocarbonylhexyl, A is single bond, $Y^0$ is 4-amidinobenzyl, and M is N;

$R^2$ is 3-aminophenyl, B is tert-butyl, A is single bond, $Y^0$ is 4-amidinobenzyl, and M is N;

$R^2$ is 3-aminophenyl, B is tert-butyl, A is single bond, $Y^0$ is 4-amidinobenzyl, and M is N;

$R^2$ is 3-aminophenyl, B is 3-hydroxypropyl, A is single bond, $Y^0$ is 4-amidinobenzyl, and M is N;

$R^2$ is 3-aminophenyl, B is 2-methylpropyl, A is single bond, $Y^0$ is 4-amidino-2-fluorobenzyl, and M is N;

$R^2$ is 3-aminophenyl, B is butyl, A is single bond, $Y^0$ is 4-amidinobenzyl, and M is N;

$R^2$ is 3-aminophenyl, B is 3-methoxy-2-propyl, A is single bond, $Y^0$ is 4-amidinobenzyl, and M is N;

$R^2$ is 3-aminophenyl, B is 3-methoxy-2-propyl, A is single bond, $Y^0$ is 4-amidinobenzyl, and M is N;

$R^2$ is 3-aminophenyl, B is 2-methoxy-2-ethyl, A is single bond, $Y^0$ is 4-amidinobenzyl, and M is N;

$R^2$ is 3-aminophenyl, B is 2-propyl, A is single bond, $Y^0$ is 5-amidino-2-thienylmethyl, and M is N;

$R^2$ is 3-aminophenyl, B is 2-propyl, A is single bond, $Y^0$ is 4-amidino-3-fluorobenzyl, and M is N; or $R^2$ is 3-carboxyphenyl, B is 2-propyl, A is single bond, $Y^0$ is 4-amidinobenzyl, and M is N.

11. A compound having the Formula:

Formula (I)

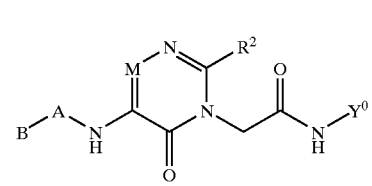

B is selected from the group consisting of C3–C7 cycloalkyl and C4 saturated heterocyclyl, wherein (a) each ring carbon is optionally substituted with $R^{33}$, (b) a ring carbon, other than the ring carbon at the point of attachment, is optionally substituted with oxo provided that no more than one ring carbon is substituted by oxo at the same time, (c) a ring carbon or nitrogen in a first alpha position relative to the ring carbon at the point of attachment is optionally substituted by $R^9$, (d) a ring carbon or nitrogen in a second alpha position relative to the ring carbon at the point of attachment is optionally substituted by $R^{13}$, (e) a ring carbon or nitrogen, if present, in a first beta position relative to the ring carbon at the point of attachment and in an alpha position relative to the ring atom optionally substituted by $R^9$, is optionally substituted by $R^{10}$, (f) a ring carbon or nitrogen, if present, in a second beta position relative to the ring carbon at the point of attachment and in an alpha position relative to the ring atom optionally substituted by $R^{13}$, is optionally substituted by $R^{12}$, (g) a ring carbon or nitrogen, if present, in a first gamma position relative to the ring carbon at the point of attachment and in an alpha position relative to the ring atom optionally substituted by $R^{10}$, is optionally substituted by $R^{11}$, and (h) a ring carbon or nitrogen, if present, in a second gamma position relative to the carbon at the point of attachment and in an alpha position relative to the ring atom optionally substituted by $R^{12}$, is optionally substituted by $R^{33}$;

$R^9$, $R^{11}$, and $R^{13}$ are independently selected from the group consisting of hydrogen, hydroxy, amino, amidino, guanidino, lower alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrogen, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxamido, and cyano;

$R^{33}$ and $R^{34}$ are independently selected from the group consisting of hydrogen, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, and cyano;

$R^{33}$ is optionally $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

M is N;

$R^2$ is $Z^0$—Q;

$Z^0$ is a covalent single bond;

Q is selected from the group consisting of aryl and heteroaryl wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrogen, hydroxy, amino, amidino, guanidino, lower alkylamino, alkylthio, alkoxy, alkylsulfinyl, alkylsulfonyl, amidosulfonyl, monoalkylamidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrogen, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyamido, carboxyalkyl, and cyano;

$Y^0$ is formula (IV):

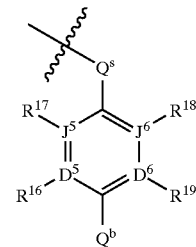

(IV)

wherein $D^5$, $D^6$, $J^5$, and $J^6$ are independently selected from the group consisting of C, N, O, S and a covalent bond with the provisos that no more than one is a covalent bond, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrogen, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently selected from the group consisting of hydrido and alkyl; and $Q^s$ is $CH_2$.

12. The compound as recited in claim 11 or a pharmaceutically acceptable salt thereof, wherein;

B is selected from the group consisting of cyclopropyl, cyclobutyl, cyclopentyl, cyclohexyl, cycloheptyl, 2-(2R)bicyclo[2.2.1]-heptyl, oxetan-3-yl, azetidin-1-yl, azetidin-2-yl, azetidin-3-yl, and bicyclo[3.1.0]hexan-6-yl, wherein (a) each ring carbon is optionally substituted with $R^{33}$, (b) a ring carbon or nitrogen in a first alpha position relative to the ring carbon at the point of attachment is optionally substituted by $R^9$, (c) a ring carbon or nitrogen in a second alpha position relative to the ring carbon at the point of attachment is optionally substituted by $R^{13}$, (d) a ring carbon or nitrogen, if present, in a first beta position relative to the ring carbon at the point of attachment and in an alpha position relative to the ring atom optionally substituted by $R^9$, is optionally substituted by $R^{10}$, and (e) a ring carbon or nitrogen, if present, in a second beta position relative to the ring carbon at the point of attachment and in an alpha position relative to the ring atom optionally substituted by $R^{13}$, is optionally substituted by $R^{12}$;

$R^9$, $R^{11}$, and $R^{13}$ are independently selected from the group consisting of hydrogen, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrogen, amidino, amidocarbonyl, N-methylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, amidosulfonyl, N-methylamidosulfonyl, N,N-dimethylamidosulfonyl, methoxycarbonyl, fluoro, chloro, bromo, and cyano;

$R^{33}$ are independently selected from the group consisting of hydrogen, amidino, guanidino, methyl, ethyl, methoxy, ethoxy, hydroxy, carboxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, cyano, and $Q^b$;

A is selected from the group consisting of single covalent bond, NH, N(CH$_3$), CH$_2$, CH$_3$CH, CH$_2$CH$_2$, and CH$_2$CH$_2$CH$_2$;

M is N;

$R^2$ is selected from the group consisting of phenyl and 2-thienyl, 2-furyl, 2-pyrrolyl, 2-imidazolyl, 2-thiazolyl, 3-isoxazolyl, 2-pyridyl, and 3-pyridyl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$Y^0$ is selected from the group consisting of:

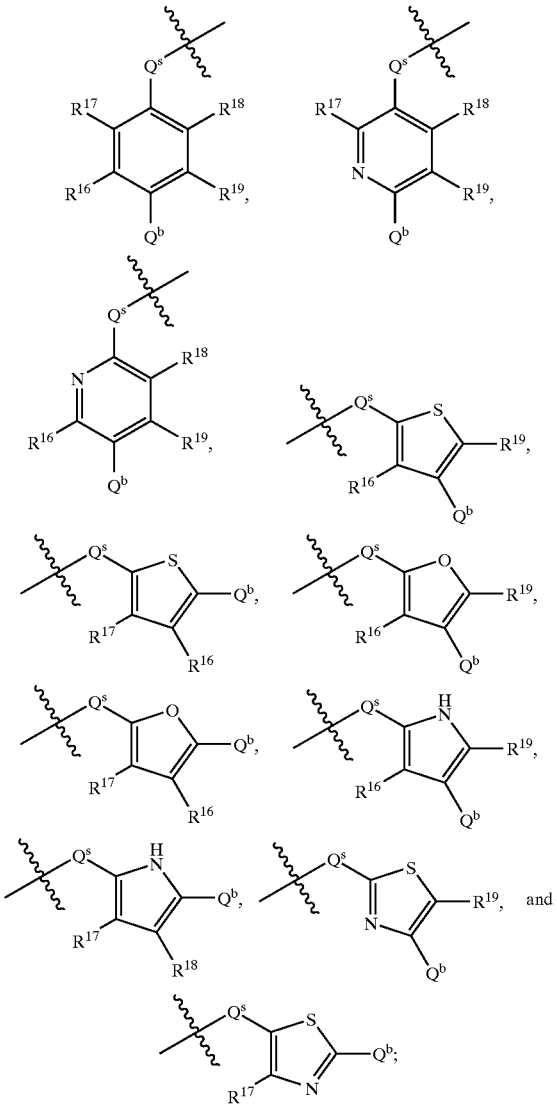

$R^{16}$, $R^{17}$, $R^{18}$, and $R^{19}$ are independently selected from the group consisting of hydrogen, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, amidosulfonyl, N-methylamidosulfonyl, hydroxymethyl, carboxy, and cyano.

$Q^b$ is selected from the group consisting of $NR^{20}R^{21}$ and $C(NR^{25})NR^{23}R^{24}$;

$R^{20}$, $R^{21}$, $R^{23}$, $R^{24}$, and $R^{25}$ are independently selected from the group consisting of hydrido, methyl, and ethyl; and $Q^s$ is CH$_2$.

13. The compound as recited in claim 12 or a pharmaceutically acceptable salt thereof, wherein;

B is selected from the group consisting of cyclopropyl, cyclobutyl, cyclopentyl, cyclohexyl, 2-(2R)-bicyclo[2.2.1]-heptyl, oxetan-3-yl, azetidin-1-yl, azetidin-2-yl, and azetidin-3-yl;

A is selected from the group consisting of a single covalent bond, CH$_2$, NHC(O), CH$_2$CH$_2$ and CH$_2$CH$_2$CH$_2$;

M is N;

R$^2$ is selected from the group consisting of 3-aminophenyl, 2,6-dichlorophenyl, 2-hydroxyphenyl, 5-amino-2-thienyl, and 3-thienyl;

Y$^0$ is selected from the group consisting of:

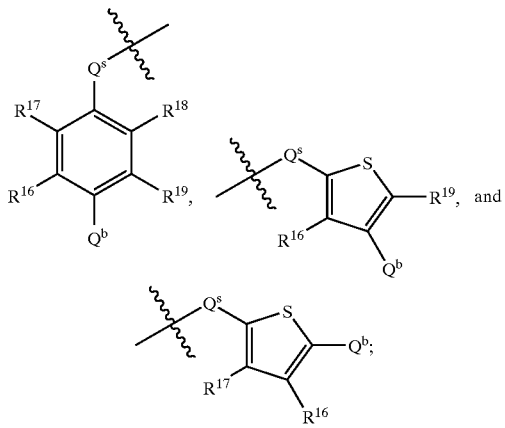

R$^{16}$ and R$^{19}$ are independently selected from the group consisting of hydrogen, amidino, amino, aminomethyl, methoxy, methylamino, hydroxy, hydroxymethyl, fluoro, chloro, and cyano;

R$^{17}$ and R$^{18}$ are independenty selected from the group consisting of hydrogen, fluoro, chloro, hydroxy, hydroxymethyl, amino, carboxy, and cyano;

Q$^b$ is selected from the group consisting of hydrogen and C(NR$^{25}$)NR$^{23}$R$^{24}$;

R$^{23}$, R$^{24}$, and R$^{25}$ are independently selected from the group consisting of hydrogen and methyl; and Q$^s$ is CH$_2$.

14. The compound as recited in claim 13 or a pharmaceutically acceptable salt thereof, wherein;

B is selected from the group consisting of cyclopropyl, cyclobutyl, cyclopentyl, cyclohexyl, 2-(2R)-bicyclo[2.2.1]-heptyl, oxetan-3-yl, azetidin-1-yl, azetidin-2-yl, and azetidin-3-yl;

A is selected from the group consisting of a single covalent bond, CH$_2$, CH$_2$CH$_2$ and CH$_2$CH$_2$CH$_2$;

M is N;

R$^2$ is selected from the group consisting of 3-aminophenyl, 2,6-dichlorophenyl, 2-hydroxyhenyl, phenyl, 5-amino-2-thienyl, and 3-thienyl; and Y$^0$ is selected from the group consisting of 5-amidino-2-thienylmethyl, 4-amidinobenzyl, 2-fluoro-4-amidinobenzyl, and 3-fluoro-4-amdinobenzyl.

15. A compound of claim 11, or a pharmaceutically acceptable salt thereof, wherein:

R$^2$ is 3-aminophenyl, B is cycylopropyl, A is single bond, Y$^0$ is 4-amidinobenzyl, and M is N;

R$^2$ is 3-aminophenyl, B is cyclobutyl, A is single bond, Y$^0$ is 4-amidino-2-fluorobenzyl, and M is N;

R$^2$ is 3-aminophenyl, B is cyclobutyl, A is single bond, Y$^0$ is 4-amidinobenzyl, and M is N;

R$^2$ is 3-aminophenyl, B is cyclopropyl, A is single bond, Y$^0$ is 4-amidino-2-fluorobenzyl, and M is N;

R$^2$ is 3-aminophenyl, B is cyclobutyl, A is single bond, Y$^0$ is 4-amidinobenzyl, and M is N;

R$^2$ is 3-aminophenyl, B is cyclobutyl, A is single bond, Y$^0$ is 4-amidino-3-fluorobenzyl, and M is N;

R$^2$ is 3-aminophenyl, B is cyclopentyl, A is single bond, Y$^0$ is 4-amidinobenzyl, and M is N;

R$^2$ is 5-amino-2-thienyl, B is cyclobutyl, A is single bond, Y$^0$ is 4-amidinobenzyl, and M is N;

R$^2$ is 3-aminophenyl, B is cyclopropyl, A is CH$_2$, Y$^0$ is 4-amidinobenzyl, and M is N;

R$^2$ is 3-aminophenyl, B is 2-(2R)-bicyclo[2.2.1]-heptyl, A is single bond, Y$^0$ is 4-amidinobenzyl, and M is N;

R$^2$ is 3-aminophenyl, B is cyclopentyl, A is single bond, Y$^0$ is 4-amidino-2-fluorobenzyl, and M is N;

R$^2$ is 3-aminophenyl, B is cyclohexyl, A is CH$_2$CH$_2$, Y$^0$ is 4-amidinobenzyl, and M is N;

R$^2$ is 2-hydroxyphenyl, B is cyclobutyl, A is single bond, Y$^0$ is 4-amidinobenzyl, and M is N;

R$^2$ is phenyl, B is cyclobutyl, A is single bond, Y$^0$ is 4-amidinobenzyl, and M is N;

R$^2$ is 3-thienyl, B is cyclobutyl, A is single bond, Y$^0$ is 4-amidinobenzyl, and M is N; or R$^2$ is 2,6-dichlorophenyl, B is cyclobutyl, A is single bond, Y$^0$ is 4-amidinobenzyl, and M is N.

* * * * *